United States Patent [19]

Fischer et al.

[11] Patent Number: 5,006,148

[45] Date of Patent: Apr. 9, 1991

[54] N-ARYL-SUBSTITUTED NITROGEN-CONTAINING HETEROCYCLES, AND THEIR USE AS HERBICIDES AND PLANT GROWTH REGULATORS

[75] Inventors: Reiner Fischer, Monheim; Uta Jensen-Korte, Duesseldorf; Franz Kunisch, Odenthal-Gloebusch; Albrecht Marhold, Leverkusen; Pieter Ooms, Krefeld; Otto Schallner, Monheim; Hans-Joachim Santel, Leverkusen; Robert R. Schmidt, Bergisch-Gladbach; Birgit Krauskopf, Bergisch-Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 435,898

[22] Filed: Nov. 13, 1989

[30] Foreign Application Priority Data

Nov. 23, 1988 [DE] Fed. Rep. of Germany ....... 3839480

[51] Int. Cl.$^5$ .................... A01N 43/56; C07D 231/22
[52] U.S. Cl. ........................................ 71/72; 71/74; 71/92; 548/375
[58] Field of Search ...................... 548/375; 71/72, 74, 71/92

[56] References Cited

U.S. PATENT DOCUMENTS 4,758,673  7/1988  Gehring et al. ..................... 548/375
4,826,867  5/1989  Jensen-Korte et al. ............. 548/375

FOREIGN PATENT DOCUMENTS 347382  12/1989  European Pat. Off. .

*Primary Examiner*—Robert W. Ramsuer
*Attorney, Agent, or Firm*—Spring Horn Kramer & Woods

[57] ABSTRACT

The invention relates to novel N-aryl-substituted nitrogen-containing heterocycles, several processes and novel intermediates for their preparation, and their use as herbicides and plant growth regulators.

7 Claims, No Drawings

N-ARYL-SUBSTITUTED NITROGEN-CONTAINING HETEROCYCLES, AND THEIR USE AS HERBICIDES AND PLANT GROWTH REGULATORS

The invention relates to novel N-aryl-substituted nitrogen-containing heterocycles, several processes and novel intermediates for their preparation, and their use as herbicides and plant growth regulators.

It is known that certain N-aryl-substituted nitrogen-containing heterocycles, such as, for example, the compound 1-(2-chloro-4-trifluoromethylphenyl)-5-methyl-4-nitropyrazole, possess herbicidal properties (cf., for example, European Patent 200,872).

However, the herbicidal activity of these previously known compounds against problem weeds, as well as their tolerance by important crop plants, are not entirely satisfactory in all fields of application.

Nothing has been known to date about a plant growth-regulating effect of the previously known compounds.

Novel N-aryl-substituted nitrogen-containing heterocycles of the general formula (I)

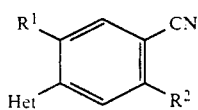

in which
Het represents a heterocycle of the formula

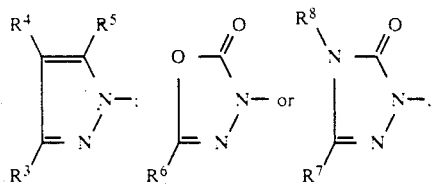

$R^1$ represents hydrogen or halogen and
$R^2$ represents halogen or a radical $-X-R^9$,
where
  $R^3$ represents hydrogen, alkyl or halogenoalkyl and
  $R^4$ represents hydrogen, halogen, alkyl or halogenoalkyl, or
  $R^3$ and $R^4$ together represent double-linked alkanediyl,
  $R^5$ represents hydrogen, halogen, alkyl or halogenoalkyl,
  $R^6$ represents hydrogen, alkyl, alkoxyalkyl, halogenoalkyl, alkenyl, halogenoalkenyl, alkinyl, halogenoalkinyl, or represents optionally substituted cycloalkyl,
  $R^7$ represents hydrogen, alkyl, alkoxyalkyl, halogenoalkyl, alkenyl, halogenoalkenyl, alkinyl, halogenoalkinyl, or represents optionally substituted cycloalkyl and
  $R^8$ represents hydrogen, alkyl, halogenoalkyl, alkenyl, halogenoalkenyl, alkinyl or halogenoalkinyl, or
  $R^7$ and $R^8$ together represent double-linked alkanediyl,
  $R^9$ represents in each case optionally substituted alkyl, alkenyl, alkinyl or cycloalkyl and
X represents oxygen or sulphur,
have been found.

Furthermore, it has been found that the novel N-aryl-substituted nitrogen-containing heterocycles of the general formula (I)

in which
Het represents a heterocycle of the formula

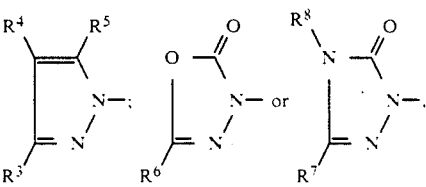

$R^1$ represents hydrogen or halogen and
$R^2$ represents halogen or a radical $-X-R^9$,
where
  $R^3$ represents hydrogen, alkyl or halogenoalkyl and
  $R^4$ represents hydrogen, halogen, alkyl or halogenoalkyl, or
  $R^3$ and $R^4$ together represent double-linked alkanediyl,
  $R^5$ represents hydrogen, halogen, alkyl or halogenoalkyl,
  $R^6$ represents hydrogen, alkyl, alkoxyalkyl, halogenoalkyl, alkenyl, halogenoalkenyl, alkinyl, halogenoalkinyl, or represents optionally substituted cycloalkyl,
  $R^7$ represents hydrogen, alkyl, alkoxyalkyl, halogenoalkyl, alkenyl, halogenoalkenyl, alkinyl, halogenoalkinyl, or represents optionally substituted cycloalkyl and
  $R^8$ represents hydrogen, alkyl, halogenoalkyl, alkenyl, halogenoalkenyl, alkinyl or halogenoalkinyl, or
  $R^7$ and $R^8$ together represent double-linked alkanediyl,
  $R^9$ represents in each case optionally substituted alkyl, alkenyl, alkinyl or cycloalkyl and
X represents oxygen or sulphur,
are obtained by one of the processes described below:
(a) N-aryl-substituted nitrogen-containing heterocycles of the formula (Ia)

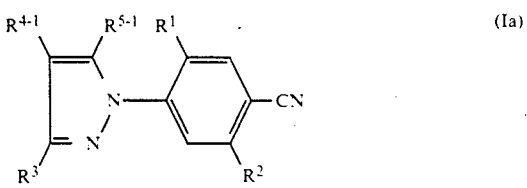

in which
$R^{4-1}$ represents hydrogen, alkyl or halogenoalkyl or together with $R^3$ represents a double-linked alkanediyl radical,
$R^{5-1}$ represents hydrogen, alkyl or halogenoalkyl and
$R^1$, $R^2$ and $R^3$ have the abovementioned meaning.
are obtained when 4-cyanophenylhydrazines of the formula (II)

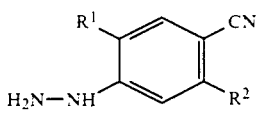

in which
R¹ and R² have the abovementioned meaning,
are reacted with 1,3-diketones of the formula (III)

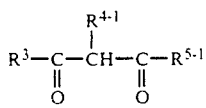

in which
R³, R⁴⁻¹ and R⁵⁻¹ have the abovementioned meaning,
or with derivatives of these diketones, such as, for example, enol ethers, enol esters, ketals, enol ether ketals, enamines or β-halogenovinyl ketones, if appropriate in the presence of a diluent and if appropriate in the presence of a reaction auxiliary;

(b) N-aryl-substituted nitrogen-containing heterocycles of the formula (Ib)

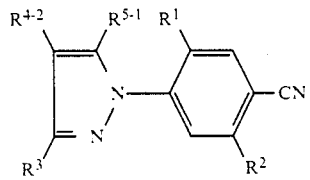

in which
$R^{4-2}$ represents halogen,
$R^{5-1}$ represents hydrogen, alkyl or halogenoalkyl and
$R^1$, $R^2$ and $R^3$ have the abovementioned meaning,
are obtained N-aryl-substituted nitrogen-containing heterocycles of the formula (Ij)

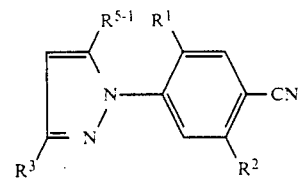

in which
$R^1$, $R^2$, $R^3$ and $R^{5-1}$ have the abovementioned meaning,
are reacted with a halogenating agent, if appropriate in the presence of a diluent;

(c) N-aryl-substituted nitrogen-containing heterocycles of the formula (Ic)

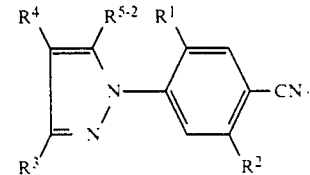

in which
$R^{5-2}$ represents halogen and
$R^1$, $R^2$, $R^3$ and $R^4$ have the abovementioned meaning.

are obtained when N-aryl-pyrazolinones of the formula (IV)

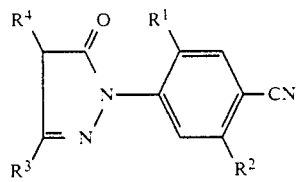

in which
$R^1$, $R^2$, $R^3$ and $R^4$ have the abovementioned meaning,
are reacted with a halogenating agent, if appropriate in the presence of a diluent and if appropriate in the presence of a reaction auxiliary;

(d) N-aryl-substituted nitrogen-containing heterocycles of the formula (Id)

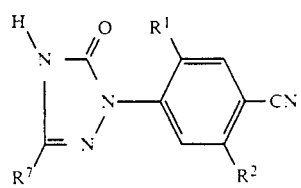

in which
$R^1$, $R^2$ and $R^7$ have the abovementioned meaning,
are obtained when 4-cyanophenylhydrazines of the formula (II)

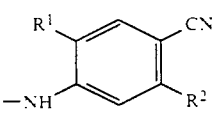

in which
$R^1$ and $R^2$ have the abovementioned meaning,
are reacted with iminocarboxylic acid esters of the formula (V)

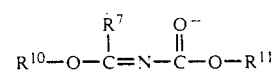

in which
$R^{10}$ and $R^{11}$ independently of one another each represent alkyl and
$R^7$ has the abovementioned meaning,
if appropriate in the presence of a diluent;

(e) N-aryl-substituted nitrogen-containing heterocycles of the formula (Ie)

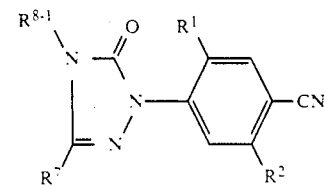

in which
$R^{8-1}$ represents alkyl, halogenoalkyl, alkenyl, halogenoalkenyl, alkinyl or halogenoalkinyl and
$R^1$, $R^2$ and $R^3$ have the abovementioned meaning,
are obtained when N-aryl-substituted nitrogen-con

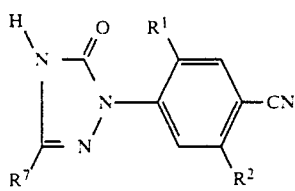

in which

R¹, R² and R⁷ have the abovementioned meaning,
are reacted with alkylating agents of the formula (VI)

$$R^{8-1}-E^1 \quad \text{(VI)}$$

in which $R^{8-1}$ has the abovementioned meaning and
$E^1$ represents an electron-withdrawing leaving group,
if appropriate in the presence of a diluent and if appropriate in the presence of a reaction auxiliary;

(f) N-aryl-substituted nitrogen-containing heterocycles of the formula (If)

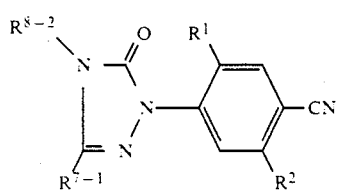

in which $R^{7-1}$ and $R^{8-2}$ together represent a double-linked alkanediyl radical
are obtained when amidrazones of the formula (VII)

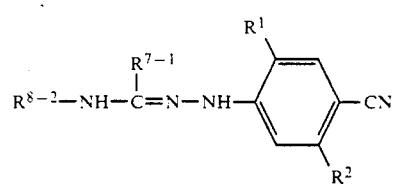

in which $R^{7-1}$ and $R^{8-2}$ have the abovementioned meaning,
are reacted with phosgene, if appropriate in the presence of a diluent and if appropriate in the presence of a reaction auxiliary;

(g) N-aryl-substituted nitrogen-containing heterocycles of the formula (Ig)

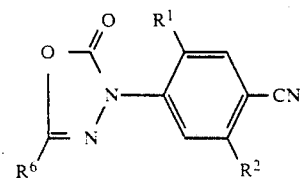

in which

R¹, R² and R⁶ have the abovementioned meaning,
are obtained when phenylhydrazides of the formula (VIII)

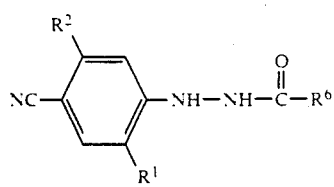

in which

R¹, R² and R⁶ have the abovementioned meaning,
are reacted with phosgene, if appropriate in the presence of a diluent and if appropriate in the presence of a reaction auxiliary;

(h) N-aryl-substituted nitrogen-containing heterocycles of the formula (Ih)

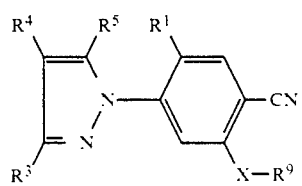

in which

R¹, R³, R⁴, R⁵, R⁹ and X have the abovementioned meaning,
are alternatively also obtained when (α) N-aryl-substituted nitrogen-containing hetero cycles of the formula (Ik)

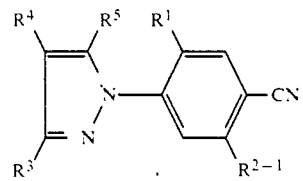

in which $R^{2-1}$ represents halogen and
R¹, R³, R⁴ and R⁵ have the abovementioned meaning,
are reacted with alcohols or thiols of the formula (IX)

$$R^9-XH \quad \text{(IX)}$$

in which

R⁹ and X have the abovementioned meaning,
if appropriate in the presence of a diluent and if appropriate in the presence of a reaction auxiliary, or when (β) (thio)phenol derivatives of the formula (X)

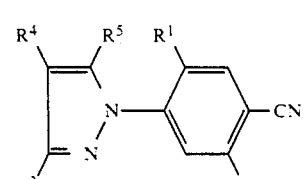

in which

R¹, R³, R⁴, R⁵ and X have the abovementioned meaning,
reacted with alkylating or acylating agents of the formula (XI)

R⁹—E² (XI)

in which
R⁹ has the abovementioned meaning and
E² represents an electron-withdrawing leaving group,
if appropriate in the presence of a diluent and if appropriate in the presence of a reaction auxiliary;
(i) N-aryl-substituted nitrogen-containing heterocycles of the formula (Ii)

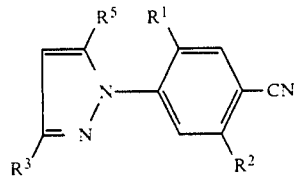

in which
R¹, R², R³ and R⁵ have the abovementioned meaning, are alternatively also obtained when 1-arylpyrazolyl-4-carboxylic acid esters of the formula (XII)

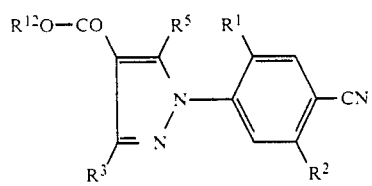

in which
R¹² represents alkyl and
R¹, R², R³ and R⁵ have the abovementioned meaning, are hydrolyzed in the presence of an acid or basic catalyst and, if appropriate, in the presence of a diluent, and the product is subsequently thermally decarboxylated.

Finally, it has been found that the novel N-aryl-substituted nitrogen-containing heterocycles of the general formula (I) possess herbicidal and plant growth-regulating properties.

Surprisingly, the N-aryl-substituted nitrogen-containing heterocycles of the general formula (I) according to the invention show a markedly better herbicidal activity towards important problem weeds when compared with the N-aryl-substituted nitrogen-containing heterocycles known from the prior art, such as, for example, the compound 1-(2-chloro-4-trifluoromethylphenyl)-5-methyl-4-nitropyrazole, which are chemically similar compounds of a similar type of action, while having a comparatively good or better selectivity towards crop plants.

Moreover, the compounds of the formula (I) according to the invention unexpectedly show an additional, plant growth-regulating effect.

Formula (I) provides a general definition of the N-aryl-substituted nitrogen-containing heterocycles according to the invention. Preferred compounds of the formula (I) are those in which
Het represents a heterocycle of the formula

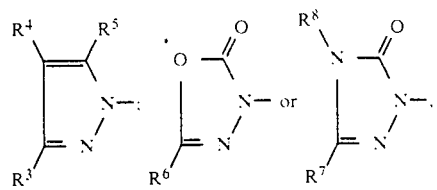

$R^1$ represents hydrogen, fluorine, chlorine or bromine and
$R^2$ represents fluorine, chlorine or bromine, or represents a radical —X—R⁹,
where
$R^3$ represents hydrogen, represents straight-chain or branched alkyl having 1 to 6 carbon atoms or represents straight-chain or branched halogenoalkyl having 1 to 4 carbon atoms and 1 to 9 identical or different halogen atoms and
$R^4$ represents hydrogen, fluorine, chlorine, bromine, iodine, represents straight-chain or branched alkyl having 1 to 6 carbon atoms or represents straight-chain or branched halogenoalkyl having 1 to 4 carbon atoms and 1 to 9 identical or different halogen atoms, or
$R^3$ and $R^4$ together represent a double-linked alkanediyl radical having 2 to 6 carbon atoms,
$R^5$ represents hydrogen, fluorine, chlorine, bromine, iodine, represents straight-chain or branched alkyl having 1 to 6 carbon atoms or represents straight-chain or branched halogenoalkyl having 1 to 4 carbon atoms and 1 to 9 identical or different halogen atoms,
$R^6$ represents hydrogen, represents in each case straight-chain or branched alkyl having 1 to 6 carbon atoms, alkenyl having 3 to 6 carbon atoms, alkinyl having 3 to 6 carbon atoms, halogenoalkyl having 1 to 4 carbon atoms and 1 to 9 identical or different halogen atoms, halogenoalkenyl having 3 to 6 carbon atoms and 1 to 5 identical or different halogen atoms, halogenoalkinyl having 3 to 6 carbon atoms and 1 to 5 identical or different halogen atoms or alkoxyalkyl having in each case 1 to 4 carbon atoms in the individual straight-chain or branched alkyl moieties or represents cycloalkyl which has 3 to 7 carbon atoms and which is optionally monosubstituted or polysubstituted by identical or different substituents, suitable substituents being: halogen, and in each case straight-chain or branched alkyl or alkoxy, each having 1 to 4 carbon atoms,
$R^7$ represents hydrogen, represents in each case straight-chain or branched alkyl having 1 to 6 carbon atoms, alkenyl having 3 to 6 carbon atoms, alkinyl having 3 to 6 carbon atoms, halogenoalkyl having 1 to 4 carbon atoms and 1 to 9 identical or different halogen atoms, halogenoalkenyl having 3 to 6 carbon atoms and 1 to 5 identical or different halogen atoms, halogenoalkinyl having 3 to 6 carbon atoms and 1 to 5 identical or different halogen atoms or alkoxyalkyl having in each case 1 to 4 carbon atoms in the individual straight-chain or branched alkyl moieties or represents cycloalkyl which has 3 to 7 carbon atoms and which is optionally monosubstituted or polysubstituted by identical or different substituents, suitable substituents being: halogen, and in each case straight-chain or branched alkyl or alkoxy, having in each case 1 to 4 carbon atoms, and R$^8$ represents hydrogen or represents in each case straight-chain or branched alkyl having 1 to 6 carbon atoms, alkenyl having 3 to 6 carbon atoms, alkinyl having 3 to 6 carbon atoms, halogenoalkyl having 1 to 4 carbon atoms and 1 to 9 identical or different halogen atoms, halogenoalkenyl having 3 to 6 carbon atoms and 1 to 5 identical or different halogen atoms or halogenoalkinyl having 3 to 6 carbon atoms and 1 to 5 identical or different halogen atoms, or R$^7$ and R$^8$ together represent a double-linked alkanediyl radical having 2 to 6 carbon atoms, R$^9$ represents in each case straight-chain or branched alkyl having 1 to 8 carbon atoms, alkenyl having 2 to 8 carbon atoms, alkinyl having 3 to 8 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, halogenoalkinyl having 3 to 8 carbon atoms and 1 to 13 identical or different halogen atoms, represents cyanoalkyl, alkoxyalkyl, alkylthioalkyl, halogenoalkoxyalkyl, alkoxyalkoxyalkyl, (bis-alkoxy)alkyl, (bis-alkylthio)alkyl, alkylcarbonylalkyl, alkoxycarbonylalkyl or alkoxyalkoxycarbonylalkyl, each having 1 to 8 carbon atoms in the individual alkyl moieties and if appropriate 1 to 9 identical or different halogen atoms, represents cycloalkyl, cycloalkyloxycarbonylalkyl or cycloalkylalkyl, each of which has 3 to 7 carbon atoms in the cycloalkyl moiety and if appropriate 1 to 4 carbon atoms in the straight-chain or branched alkyl moiety and each of which is optionally monosubstituted or polysubstituted by identical or different substituents, suitable substituents in each case being: halogen and in each case straight-chain or branched alkyl or alkoxy, each having 1 to 4 carbon atoms, R$^9$ furthermore represents oxetanylalkyl, tetrahydrofuranylalkyl, tetrahydrofuranylalkyloxycarbonylalkyl or tetrahydropyranylalkyl, each of which has 1 to 3 carbon atoms in the respective alkyl moieties and each of which is optionally substituted by alkyl having 1 to 4 carbon atoms or R$^9$ represents aralkyl which has 6 to 10 carbon atoms in the aryl moiety and 1 to 4 carbon atoms in the straight-chain or branched alkyl moiety and which is optionally monosubstituted or polysubstituted by identical or different substituents, suitable aryl substituents being: halogen, cyano, nitro, in each case straight-chain or branched alkyl, alkoxy, alkylthio or alkoxycarbonyl, each having 1 to 4 carbon atoms, or in each case straight-chain or branched halogenoalkyl, halogenoalkoxy or halogenoalkylthio, each having 1 to 4 carbon atoms and 1 to 9 identical or different halogen atoms, and X represents oxygen or sulphur.

Particularly preferred compounds of the formula (I) are those in which

Het represents a heterocycle of the formula

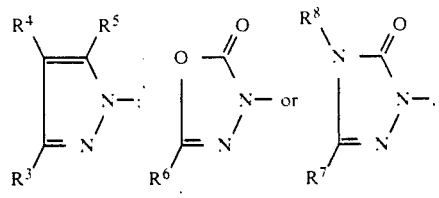

R$^1$ represents hydrogen, fluorine or chlorine and

R$^2$ represents fluorine, chlorine or represents a radical —X—R$^9$, where

R$^3$ represents hydrogen, methyl, ethyl, n- or i-propyl, n-, i-, s- or t-butyl, represents fluoromethyl, difluoromethyl, trifluoromethyl, chloromethyl, dichloromethyl, trichloromethyl, difluorochloromethyl or dichlorofluoromethyl and R$^4$ represents hydrogen, fluorine, chlorine, bromine, represents methyl, ethyl, n- or i-propyl, n-, i-, s- or t-butyl, represents fluoromethyl, difluoromethyl, trifluoromethyl, chloromethyl, dichloromethyl, trichloromethyl, difluorochloromethyl or dichlorofluoromethyl, or R$^3$ and R$^4$ together represent a 1,3-propanediyl radical, a 1,4-butanediyl radical or a 1,5-pentanediyl radical, R$^5$ represents hydrogen, fluorine, chlorine, bromine, represents methyl, ethyl, n- or i-propyl, n-, i-, s- or t-butyl, represents fluoromethyl, difluoromethyl, trifluoromethyl, chloromethyl, dichloromethyl, trichloromethyl, difluorochloromethyl or dichlorofluoromethyl, R$^6$ represents hydrogen, represents methyl, ethyl, n- or i-propyl, n-, i-, s- or t-butyl, represents methyl, ethyl or t-butyl, each of which is monosubstituted, disubstituted or trisubstituted by fluorine and/or chlorine, represents allyl, represents n- or i-butenyl, represents chloroallyl, represents dichloroallyl, represents propargyl, represents chloropropargyl, represents methoxymethyl or represents cyclopropyl, cyclopentyl or cyclohexyl, each of which is optionally monosubstituted to pentasubstituted by identical or different substituents from the series comprising fluorine, chlorine, methyl and/or methoxy, R$^7$ represents hydrogen, represents methyl, ethyl, n- or i-propyl, n-, i-, s- or t-butyl, represents methyl, ethyl or t-butyl, each of which is optionally monosubstituted, disubstituted or trisubstituted by fluorine and/or chlorine, represents allyl, represents n- or i-butenyl, represents chloroallyl, represents dichloroallyl, represents propargyl, represents chloropropargyl, represents methoxymethyl or represents cyclopropyl, cyclopentyl or cyclohexyl, each of which is optionally monosubstituted to pentasubstituted by identical or different substituents from the series comprising fluorine, chlorine, methyl and/or methoxy and R$^8$ represents hydrogen, represents methyl, ethyl, n- or i-propyl, n-, i-, s- or t-butyl, represents methyl, ethyl or t-butyl, each of which is optionally monosubstituted, disubstituted or trisubstituted by fluorine and/or chlorine, represents allyl, represents n- or i-butenyl, represents chloroallyl, represents dichloroallyl, represents propargyl or represents chloropropargyl, or R$^7$ and R$^8$ together represent a 1,3-propanediyl radical, a 1,4-butanediyl radical or a 1,5-pentanediyl radical, R$^9$ represents methyl, ethyl, n- or i-propyl, n-, i-, s- or t-butyl, represents allyl, propargyl, represents in each case straight-chain or branched pentyl, hexyl, butenyl, pentenyl, hexenyl, butinyl, pentinyl or hexinyl, moreover represents in each case straight-chain or branched halogenoalkyl having 1 to 4 carbon atoms, halogenoalkinyl or halogenoalkenyl having in each case 3 to 5 carbon atoms and in each case 1 to 8 identical or different halogen atoms, in particular fluorine, chlorine or bromine, represents i each case straight-chain or branched cyanoalkyl, alkoxyalkyl, alkylthioalkyl, halogenoalkoxyalkyl, alkoxyalkoxyalkyl, alkylcarbonylalkyl, alkoxycarbonylalkyl or alkoxyalkoxycarbonylalkyl, each having 1 to 5 carbon atoms in the individual alkyl moieties, moreover represents cyclopropylmethyl, cyclopentylmethyl, cyclohexylmethyl, cyclopropyloxycarbonylmethyl, cyclopentyloxycarbonylmethyl, cyclohexyloxycarbonylmethyl, cyclopropyl, cyclopentyl or cyclohexyl, each of which is optionally monosubstituted to trisubstituted by identical or different substituents from the series comprising methyl, methoxy, fluorine or chlorine, represents oxetanylmethyl, oxetanylethyl, tetrahydrofuranylmethyl, tetrahydrofuranylethyl, tetrahydrofuranylmethyloxycarbonylmethyl, tetrahydropyranylmethyl or tetrahydropyranylethyl, each of which is optionally substituted by methyl or ethyl, or represents benzyl or phenylethyl, each of which is optionally monosubstituted to trisubstituted by identical or different substituents, suitable substituents in each case being: fluorine, chlorine, bromine, cyano, nitro, methyl, ethyl, n- or i-propyl, n-, i-, s- or t-butyl, methoxy, ethoxy, n- or i-propxy, methylthio, ethylthio, methoxycarbonyl, ethoxycarbonyl, trifluoromethyl, trifluoromethoxy or trifluoromethylthio and X represents oxygen or sulphur.

Very particularly preferred compounds of the formula (I) are those in which

Het represents a heterocycle of the formula

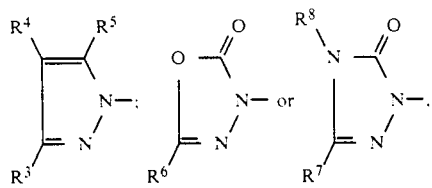

$R^1$ represents hydrogen or fluorine and
$R^2$ represents fluorine or represents a radical —X—$R^9$, where
$R^3$ represents hydrogen, methyl, ethyl, n- or i-propyl, n-, i-, s- or t-butyl, represents fluoromethyl, difluoromethyl or trifluoromethyl and
$R^4$ represents hydrogen, chlorine, bromine, methyl or trifluoromethyl, or
$R^3$ and $R^4$ together represent a 1,3-propanediyl radical or represent a 1,4-butanediyl radical,
$R^5$ represents hydrogen, chlorine, bromine, methyl, ethyl, t-butyl or trifluoromethyl, $R^6$ represents methyl, ethyl, n- or i-propyl, n-, i-, s- or t-butyl, represents trifluoromethyl, represents fluoro-1,1-dimethylethyl or represents cyclopropyl which is optionally monosubstituted to pentasubstituted by identical or different substituents from the series comprising fluorine, chlorine or methyl,
$R^7$ represents methyl and
$R^8$ represents hydrogen, methyl, ethyl, allyl, propargyl, fluoromethyl, difluoromethyl or trifluoromethyl, or
$R^7$ and $R^8$ together represent a 1,3-propanediyl radical or represent a 1,4-butanediyl radical,
$R^9$ represents methyl, ethyl, n- or i-propyl, n-, i-, s- or t-butyl, represents allyl, propargyl, represents in each case straight-chain or branched pentyl, hexyl, butenyl, pentenyl, hexenyl, butinyl, pentinyl or hexinyl, moreover represents in each case straight-chain or branched halogenoalkyl having 1 to 4 carbon atoms or halogenoalkenyl having 3 to 5 carbon atoms and in each case 1 to 5 identical or different halogen atoms, in particular fluorine, chlorine or bromine, represents in each case straight-chain or branched cyanoalkyl, alkoxyalkyl, alkoxyalkoxyalkyl or alkoxycarbonylalkyl having in each case 1 to 5 carbon atoms in the individual alkyl moieties, moreover represents cyclopropylmethyl, cyclopentylmethyl, cyclohexylmethyl, cyclopropyloxycarbonylmethyl, cyclopentyloxycarbonylmethyl, cyclohexyloxycarbonylmethyl, cyclopropyl, cyclopentyl, cyclohexyl, each of which is optionally monosubstituted to trisubstituted by identical or different substituents from the series comprising methyl, methoxy, fluorine or chlorine, represents oxetanylmethyl, oxetanylethyl, tetrahydrofuranylmethyl, tetrahydrofuranylmethyloxycarbonylmethyl or tetrahydropyranylmethyl, each of which is optionally substituted by methyl or ethyl, or represents benzyl or phenylethyl, each of which is optionally monosubstituted to trisubstituted by identical or different substituents, suitable substituents in each case being: fluorine, chlorine, bromine, cyano, nitro, methyl, ethyl, n- or i-propyl, n-, i-, s- or t-butyl, methoxy, ethoxy, n- or i-propoxy, methylthio, ethylthio, methoxycarbonyl, ethoxycarbonyl, trifluoromethyl, trifluoromethoxy or trifluoromethylthio, and X represents oxygen or sulphur.

The following N-aryl-substituted nitrogen-containing heterocycles of the general formula (I) may be mentioned individually in addition to the compounds mentioned in the Preparation Examples:

| Het | $R^1$ | $R^2$ |
| --- | --- | --- |

-continued
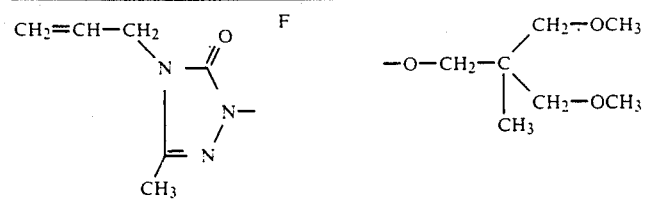 F 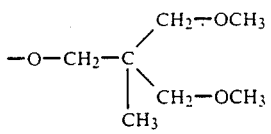
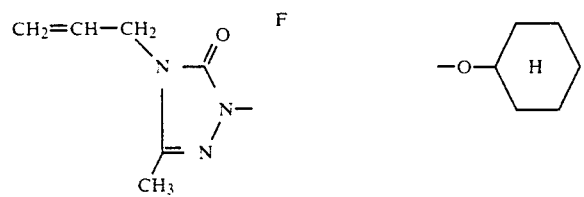 F 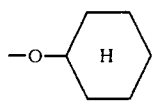
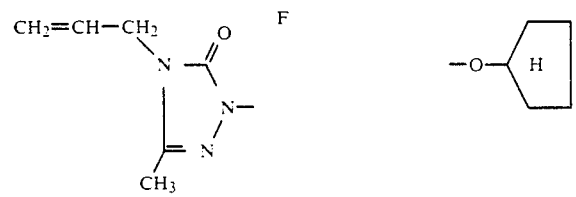 F 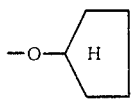
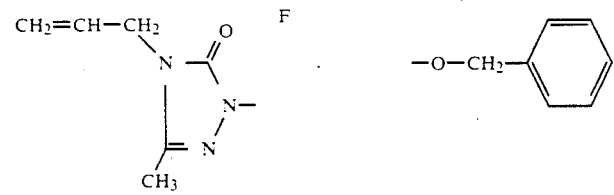 F 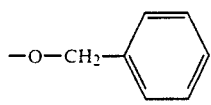
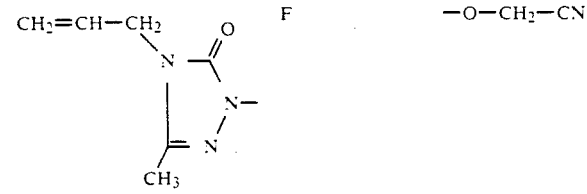 F —O—CH$_2$—CN
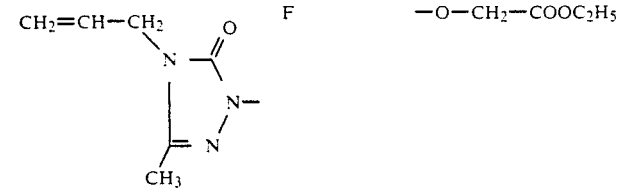 F —O—CH$_2$—COOC$_2$H$_5$
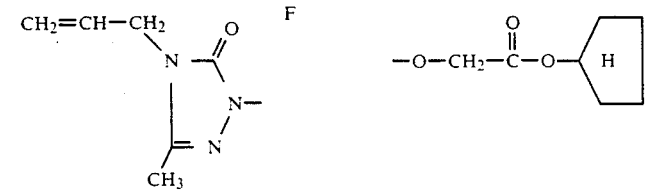 F 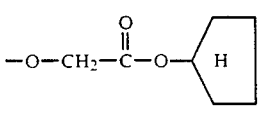
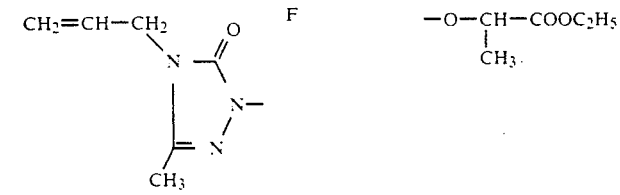 F 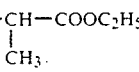

-continued
| | | |
|---|---|---|
| 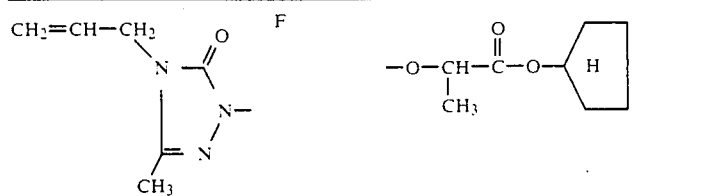 | F | −O−CH(CH₃)−C(=O)−O−cyclopentyl |
| 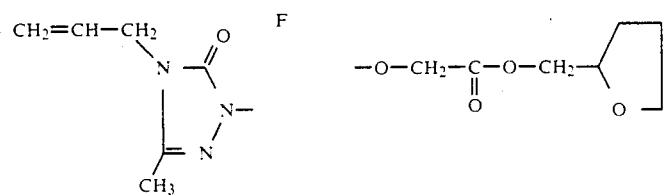 | F | −O−CH₂−C(=O)−O−CH₂−(tetrahydrofuran-2-yl) |
| 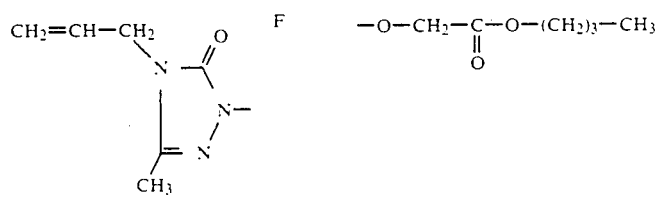 | F | −O−CH₂−C(=O)−O−(CH₂)₃−CH₃ |
| 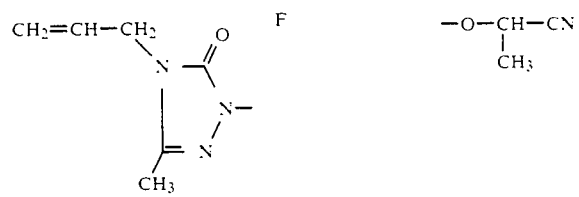 | F | −O−CH(CH₃)−CN |
| 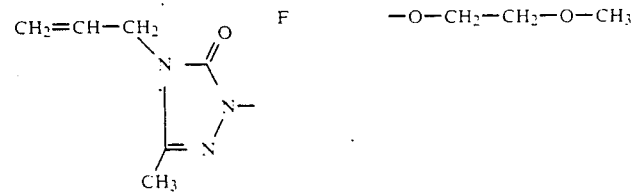 | F | −O−CH₂−CH₂−O−CH₃ |
| 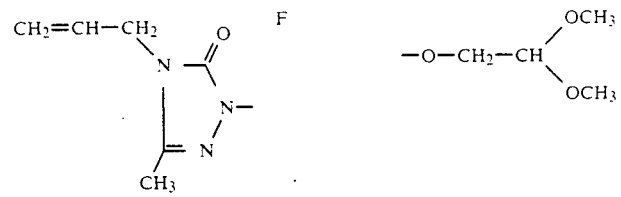 | F | −O−CH₂−CH(OCH₃)₂ |
| 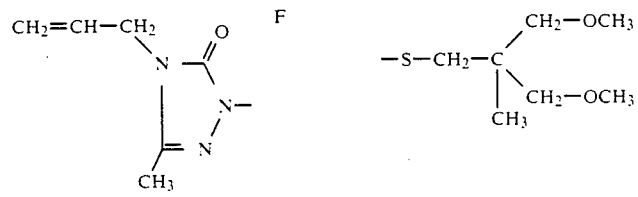 | F | −S−CH₂−C(CH₃)(CH₂OCH₃)₂ |
| 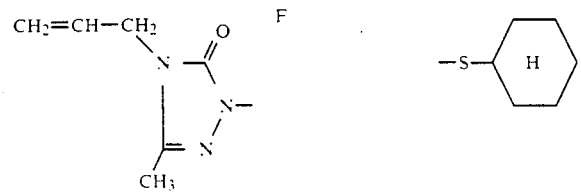 | F | −S−cyclohexyl |

-continued
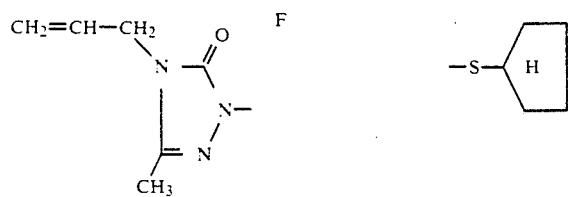 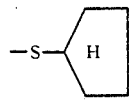
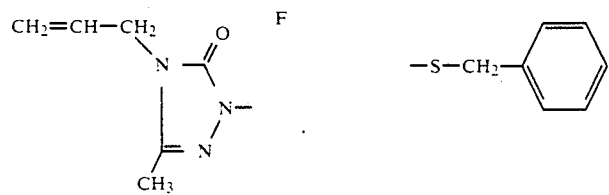 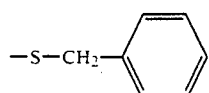
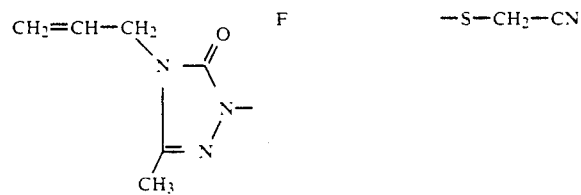 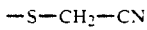
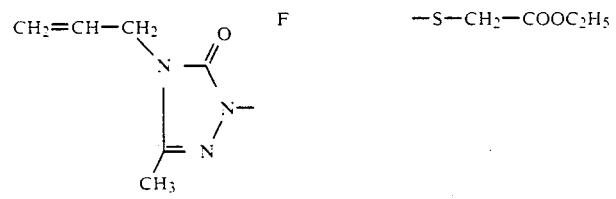 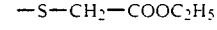
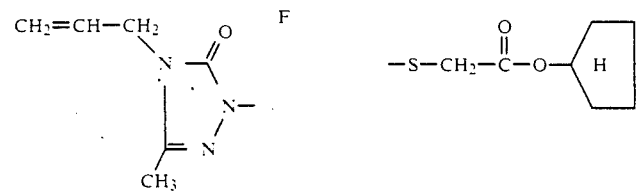 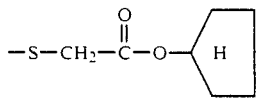
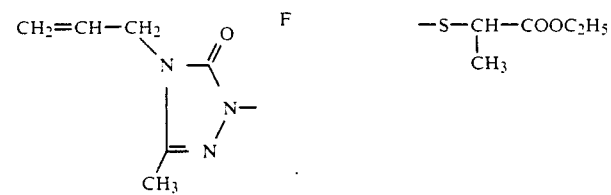 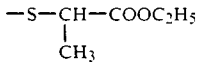
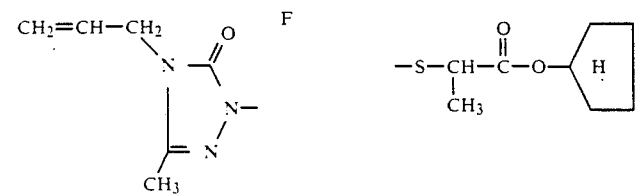 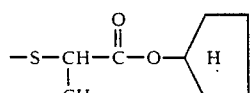
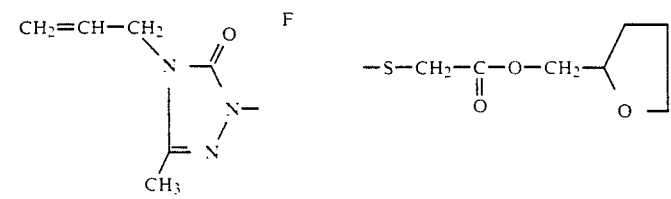 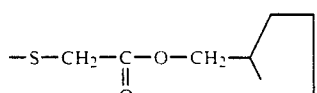

-continued
| | | |
|---|---|---|
| 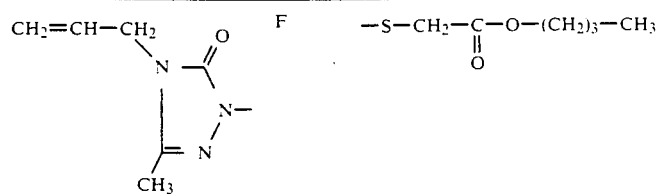 | F | —S—CH₂—C(=O)—O—(CH₂)₃—CH₃ |
| 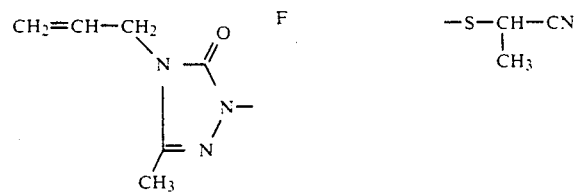 | F | —S—CH(CH₃)—CN |
| 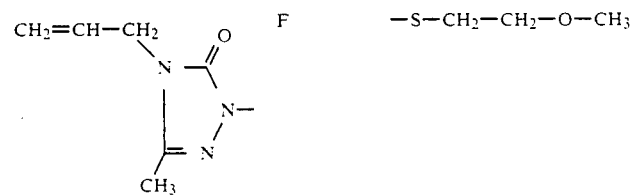 | F | —S—CH₂—CH₂—O—CH₃ |
| 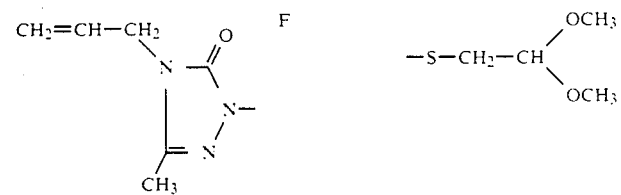 | F | —S—CH₂—CH(OCH₃)₂ |
| 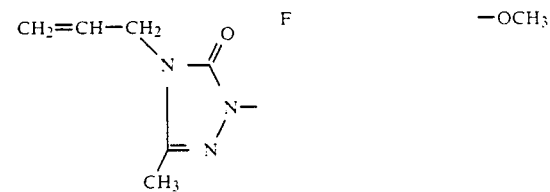 | F | —OCH₃ |
| 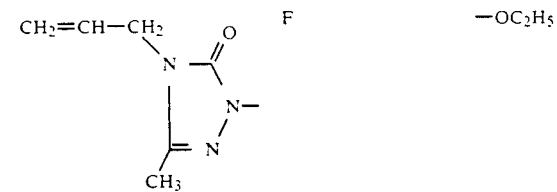 | F | —OC₂H₅ |
| 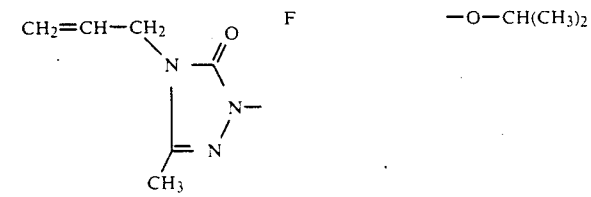 | F | —O—CH(CH₃)₂ |
| 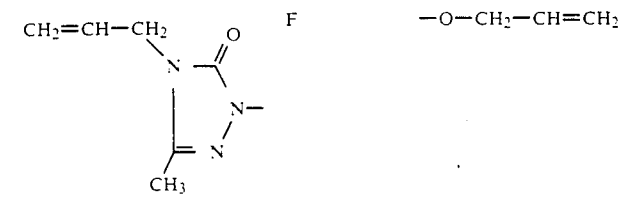 | F | —O—CH₂—CH=CH₂ |

-continued

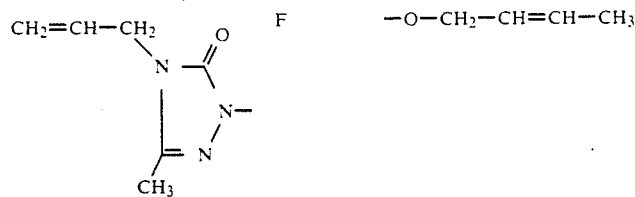 F —O—CH$_2$—CH=CH—CH$_3$

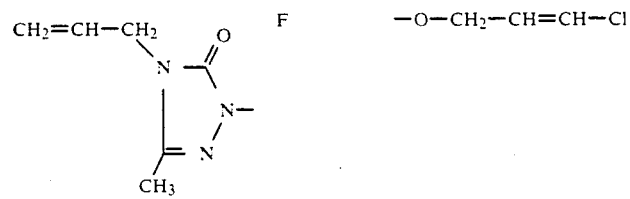 F —O—CH$_2$—CH=CH—Cl

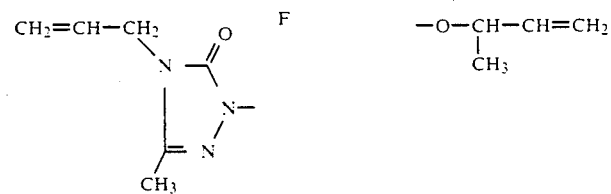 F —O—CH—CH=CH$_2$
$\quad\quad\quad\quad\quad\quad$ |
$\quad\quad\quad\quad\quad\quad$ CH$_3$

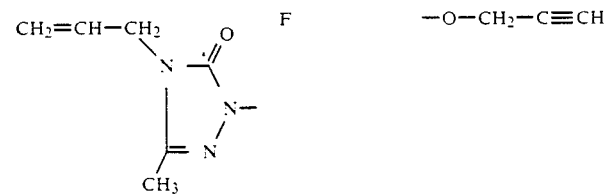 F —O—CH$_2$—C≡CH

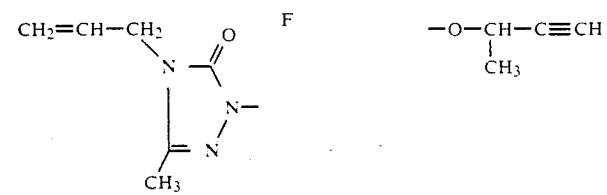 F —O—CH—C≡CH
$\quad\quad\quad\quad\quad\quad$ |
$\quad\quad\quad\quad\quad\quad$ CH$_3$

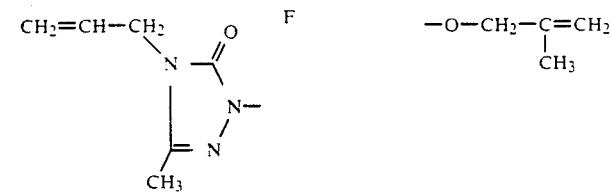 F —O—CH$_2$—C=CH$_2$
$\quad\quad\quad\quad\quad\quad\quad\quad$ |
$\quad\quad\quad\quad\quad\quad\quad\quad$ CH$_3$

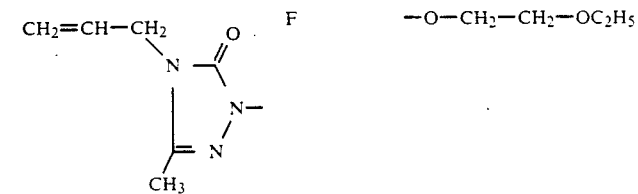 F —O—CH$_2$—CH$_2$—OC$_2$H$_5$

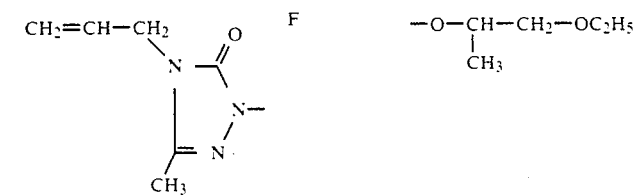 F —O—CH—CH$_2$—OC$_2$H$_5$
$\quad\quad\quad\quad\quad\quad$ |
$\quad\quad\quad\quad\quad\quad$ CH$_3$ -continued
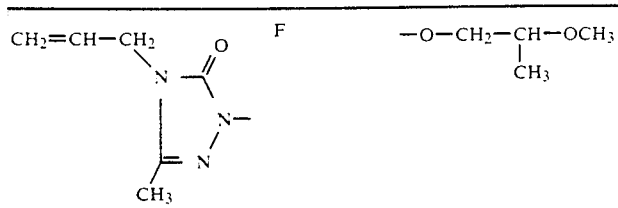 F    $-O-CH_2-CH-OCH_3$
                                                           |
                                                            $CH_3$
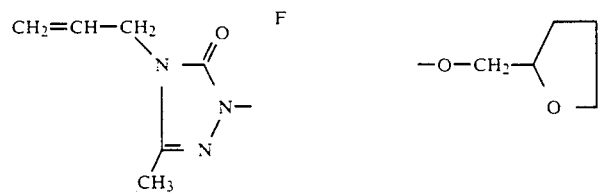 F    $-O-CH_2\text{-}\langle\text{tetrahydrofuran-2-yl}\rangle$
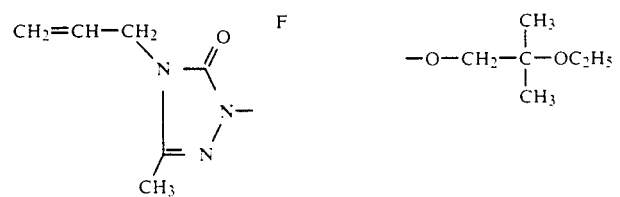 F    $-O-CH_2-\underset{CH_3}{\overset{CH_3}{C}}-OC_2H_5$
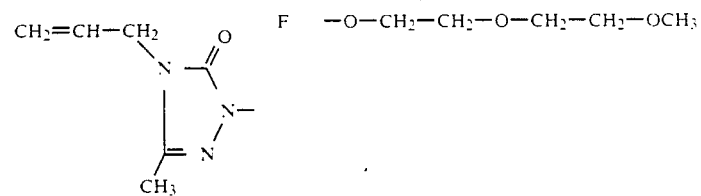 F    $-O-CH_2-CH_2-O-CH_2-CH_2-OCH_3$
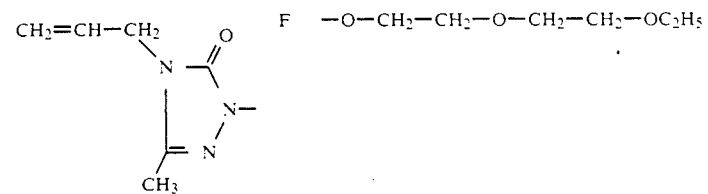 F    $-O-CH_2-CH_2-O-CH_2-CH_2-OC_2H_5$
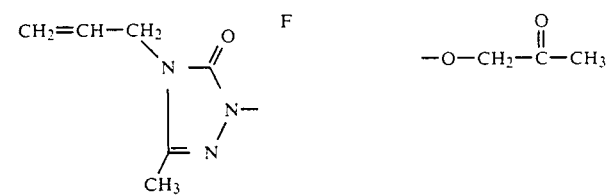 F    $-O-CH_2-\overset{O}{\overset{\|}{C}}-CH_3$
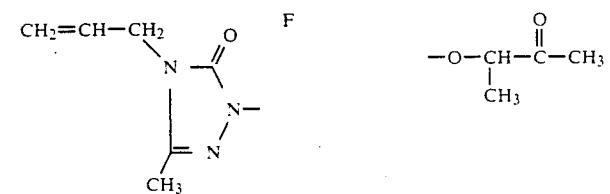 F    $-O-\underset{CH_3}{CH}-\overset{O}{\overset{\|}{C}}-CH_3$
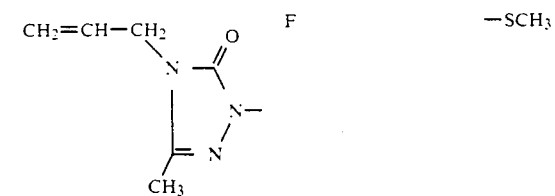 F    $-SCH_3$ -continued
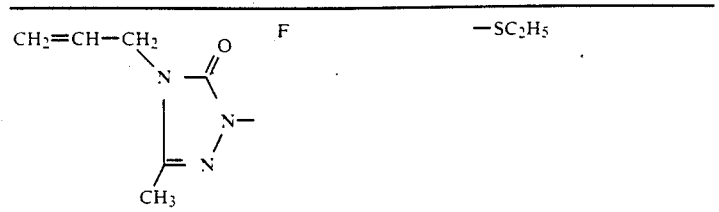 F  $-SC_2H_5$
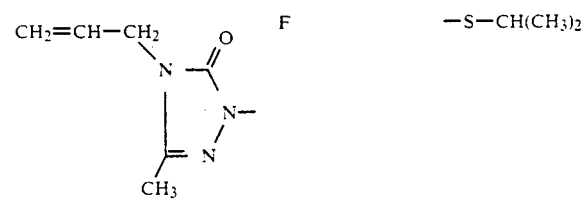 F  $-S-CH(CH_3)_2$
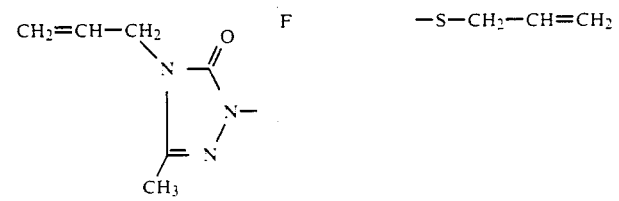 F  $-S-CH_2-CH=CH_2$
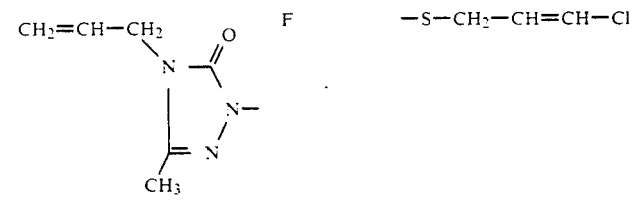 F  $-S-CH_2-CH=CH-Cl$
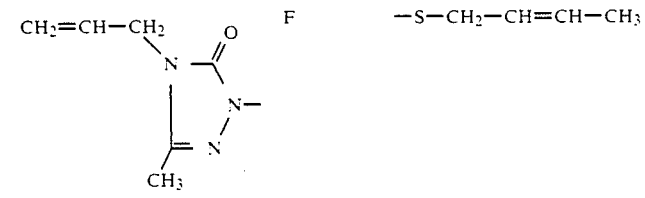 F  $-S-CH_2-CH=CH-CH_3$
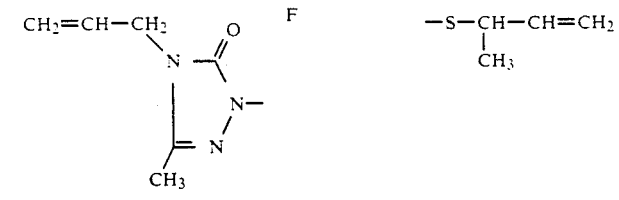 F  $-S-CH-CH=CH_2$
                            $\phantom{-S-}|$
                            $\phantom{-S-}CH_3$
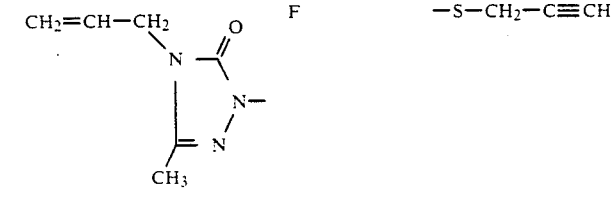 F  $-S-CH_2-C\equiv CH$
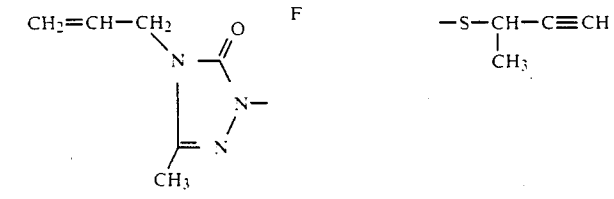 F  $-S-CH-C\equiv CH$
                            $\phantom{-S-}|$
                            $\phantom{-S-}CH_3$ -continued
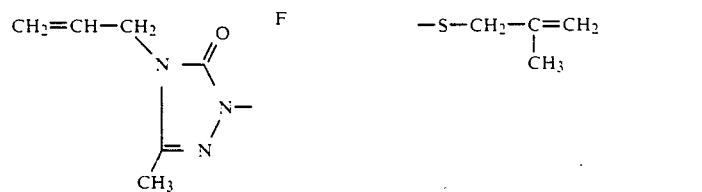 F —S—CH$_2$—C=CH$_2$
                         |
                         CH$_3$
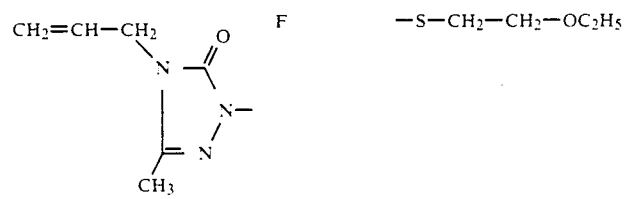 F —S—CH$_2$—CH$_2$—OC$_2$H$_5$
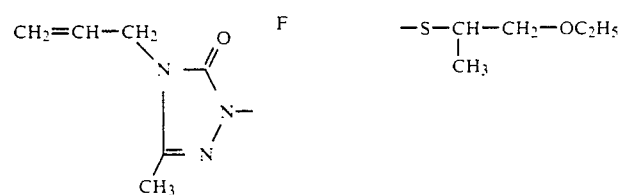 F —S—CH—CH$_2$—OC$_2$H$_5$
                        |
                        CH$_3$
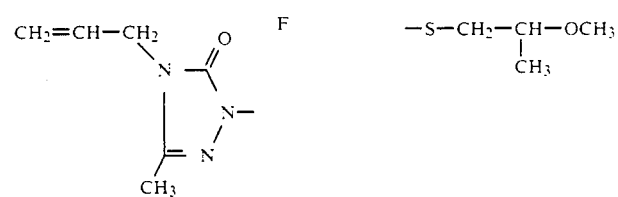 F —S—CH$_2$—CH—OCH$_3$
                               |
                               CH$_3$
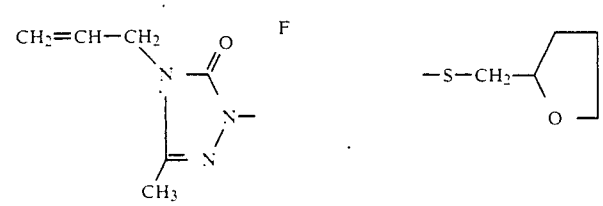 F —S—CH$_2$—⟨tetrahydrofuran-2-yl⟩
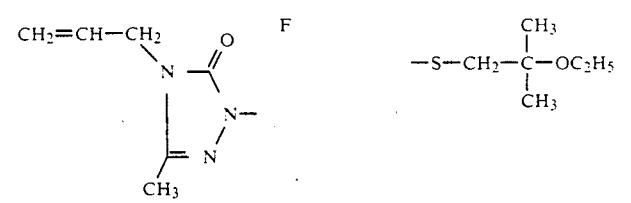 F   CH$_3$
                         |
                    —S—CH$_2$—C—OC$_2$H$_5$
                         |
                         CH$_3$
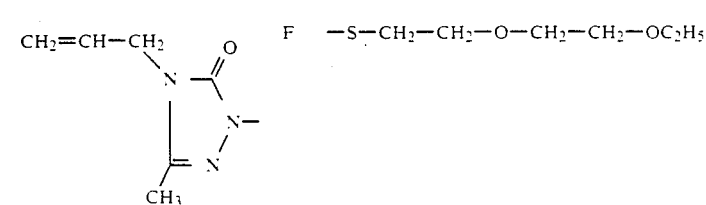 F —S—CH$_2$—CH$_2$—O—CH$_2$—CH$_2$—OCH$_3$
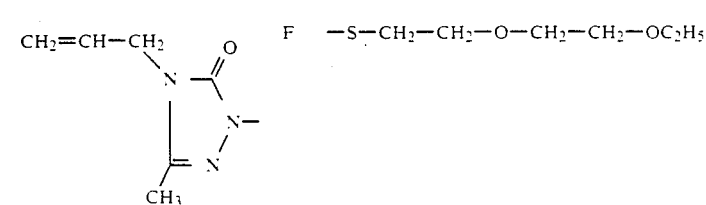 F —S—CH$_2$—CH$_2$—O—CH$_2$—CH$_2$—OC$_2$H$_5$ -continued
| | | |
|---|---|---|
| 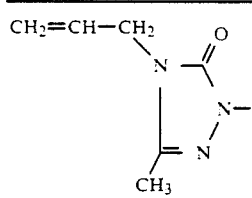 | F | 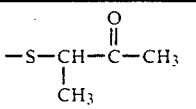 |
| 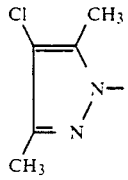 | F | 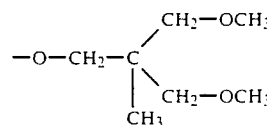 |
| 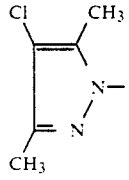 | F | 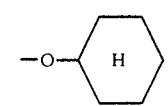 |
| 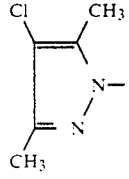 | F | 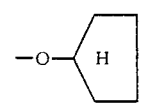 |
| 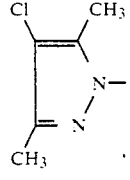 | F | 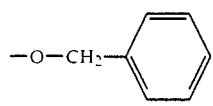 |
| 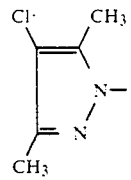 | F | —O—CH$_2$—CN |
| 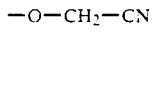 | F | —O—CH$_2$—COOC$_2$H$_5$ |
| 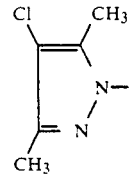 | F | 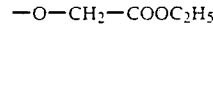 |
| 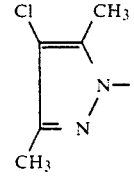 | F | 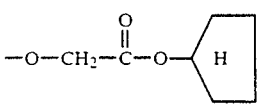 |

-continued
| | | |
|---|---|---|
| 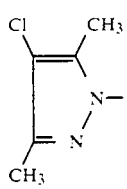 | F | 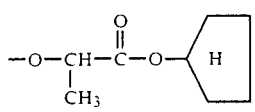 |
| 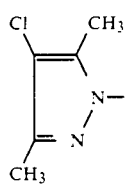 | F | 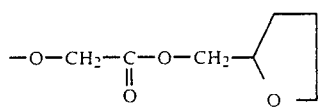 |
| 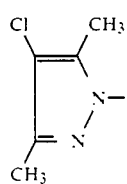 | F | 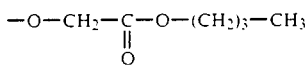 |
| 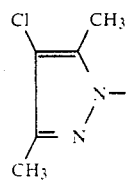 | F | 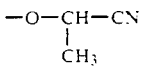 |
| 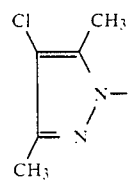 | F | 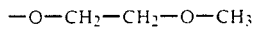 |
| 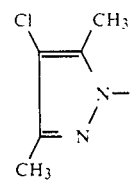 | F | 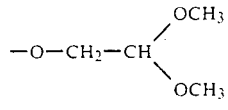 |
| 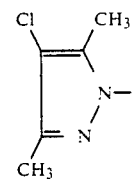 | F | 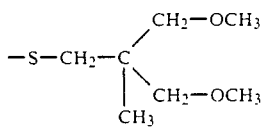 |
| 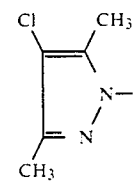 | F | 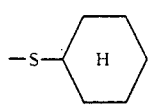 |
| 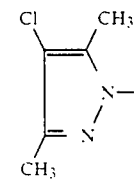 | F | 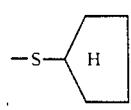 |

-continued
| | | |
|---|---|---|
| 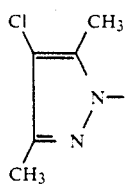 | F | 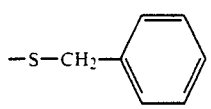 |
| 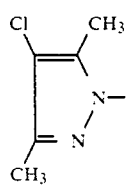 | F | —S—CH$_2$—CN |
| 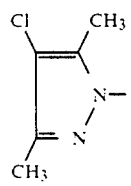 | F | —S—CH$_2$—COOC$_2$H$_5$ |
| 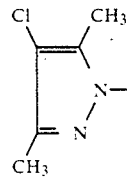 | F | 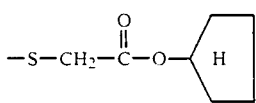 |
| 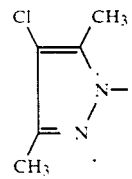 | F | 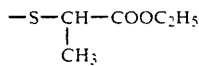 |
|  | F | 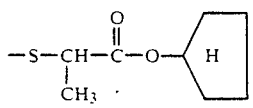 |
|  | F | 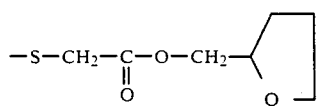 |
|  | F | 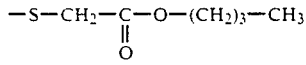 |
|  | F | 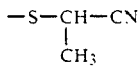 |

-continued
| | | |
|---|---|---|
| 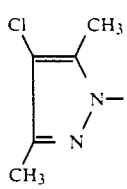 | F | —S—CH$_2$—CH$_2$—O—CH$_3$ |
| 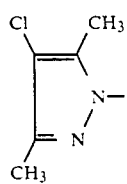 | F | 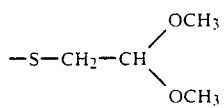 |
| 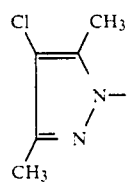 | F | —OCH$_3$ |
| 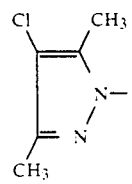 | F | —OC$_2$H$_5$ |
| 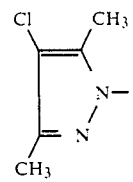 | F | —O—CH(CH$_3$)$_2$ |
| 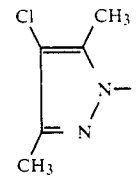 | F | —O—CH$_2$—CH=CH$_2$ |
| 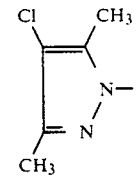 | F | —O—CH$_2$—CH=CH—CH$_3$ |
| 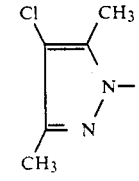 | F | —O—CH$_2$—CH=CH—Cl |
| 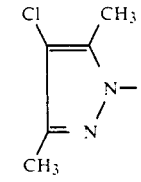 | F | 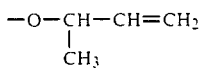 |

| Pyrazole (Cl, CH₃, CH₃) | F | —O—CH₂—C≡CH |
| Pyrazole (Cl, CH₃, CH₃) | F | —O—CH(CH₃)—C≡CH |
| Pyrazole (Cl, CH₃, CH₃) | F | —O—CH₂—C(CH₃)=CH₂ |
| Pyrazole (Cl, CH₃, CH₃) | F | —O—CH₂—CH₂—OC₂H₅ |
| Pyrazole (Cl, CH₃, CH₃) | F | —O—CH(CH₃)—CH₂—OC₂H₅ |
| Pyrazole (Cl, CH₃, CH₃) | F | —O—CH₂—CH(CH₃)—OCH₃ |
| Pyrazole (Cl, CH₃, CH₃) | F | —O—CH₂-(tetrahydrofuran-2-yl) |
| Pyrazole (Cl, CH₃, CH₃) | F | —O—CH₂—C(CH₃)₂—OC₂H₅ |
| Pyrazole (Cl, CH₃, CH₃) | F | —O—CH₂—CH₂—O—CH₂—CH₂—OCH₃ |

-continued
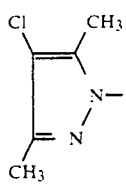 F —O—CH₂—CH₂—O—CH₂—CH₂—OC₂H₅
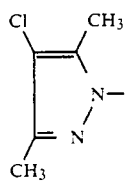 F 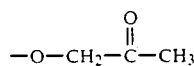
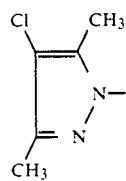 F 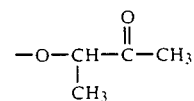
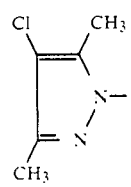 F —SCH₃
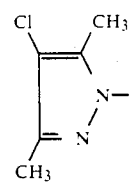 F —SC₂H₅
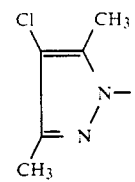 F —S—CH(CH₃)₂
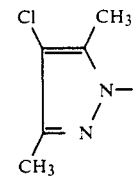 F —S—CH₂—CH=CH₂
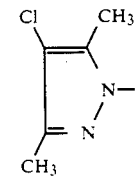 F —S—CH₂—CH=CH—Cl
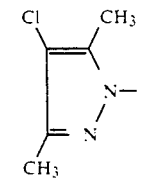 F —S—CH₂—CH=CH—CH₃

-continued
| | | |
|---|---|---|
| 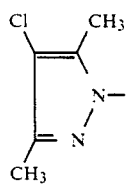 | F | —S—CH—CH=CH$_2$<br>　　　｜<br>　　　CH$_3$ |
| 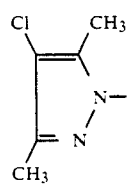 | F | —S—CH$_2$—C≡CH |
| 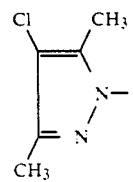 | F | —S—CH—C≡CH<br>　　　｜<br>　　　CH$_3$ |
| 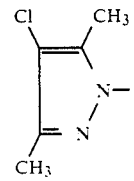 | F | —S—CH$_2$—C=CH$_2$<br>　　　　　　｜<br>　　　　　　CH$_3$ |
| 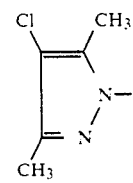 | F | —S—CH$_2$—CH$_2$—OC$_2$H$_5$ |
| 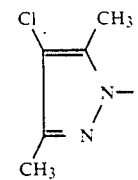 | F | —S—CH—CH$_2$—OC$_2$H$_5$<br>　　　｜<br>　　　CH$_3$ |
| 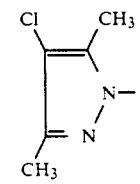 | F | —S—CH$_2$—CH—OCH$_3$<br>　　　　　　｜<br>　　　　　　CH$_3$ |
| 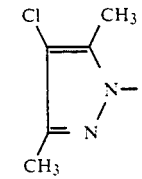 | F | 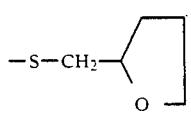 |
| 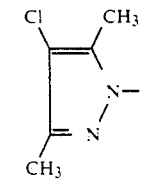 | F | 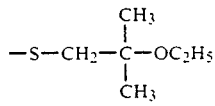 |

-continued
| | | |
|---|---|---|
| 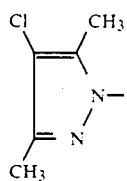 | F | —S—CH$_2$—CH$_2$—O—CH$_2$—CH$_2$—OCH$_3$ |
| 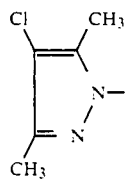 | F | —S—CH$_2$—CH$_2$—O—CH$_2$—CH$_2$—OC$_2$H$_5$ |
| 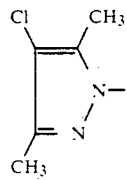 | F | 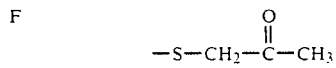 |
| 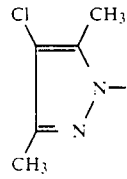 | F | 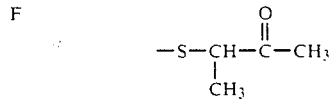 |
| 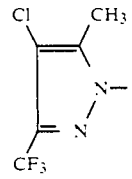 | F | 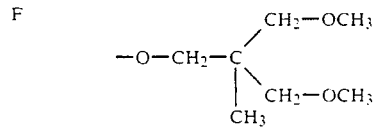 |
| 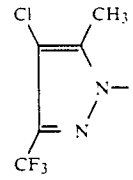 | F | 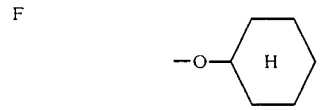 |
| 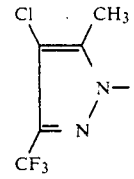 | F |  |
| 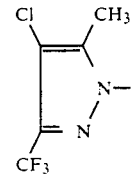 | F | 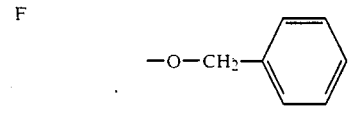 |
| 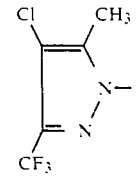 | F | —O—CH$_2$—CN |

-continued
| | | |
|---|---|---|
| 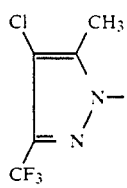 | F | —O—CH₂—COOC₂H₅ |
| 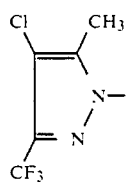 | F | 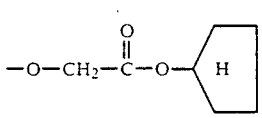 |
| 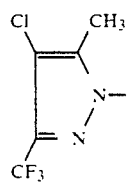 | F | 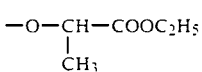 |
| 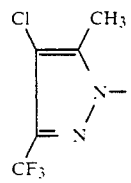 | F | 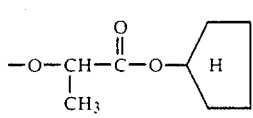 |
| 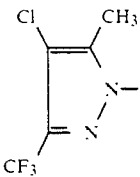 | F | 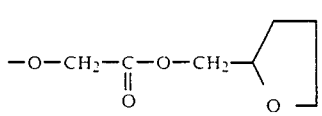 |
| 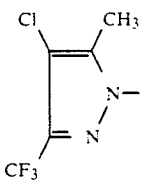 | F | 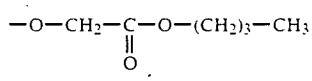 |
| 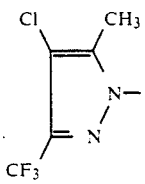 | F | 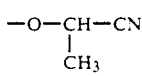 |
| 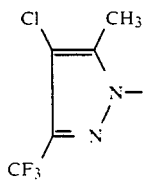 | F | —O—CH₂—CH₂—O—CH₃ |

-continued
| | | |
|---|---|---|
| 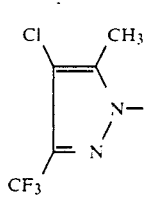 | F | 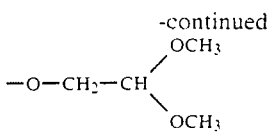 |
| 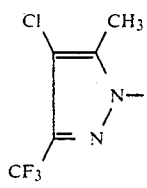 | F | 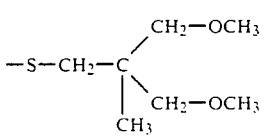 |
| 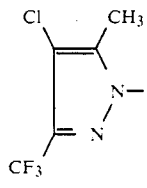 | F | 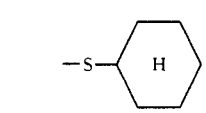 |
| 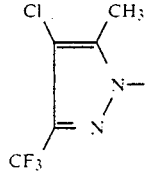 | F | 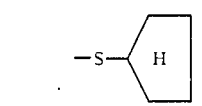 |
| 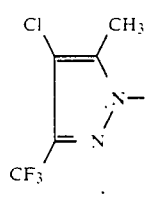 | F | 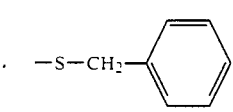 |
| 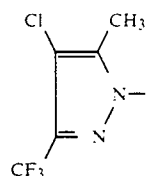 | F | —S—CH$_2$—CN |
| 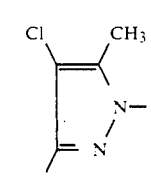 | F | —S—CH$_2$—COOC$_2$H$_5$ |
| 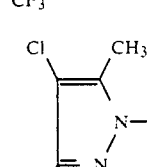 | F | 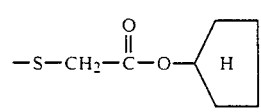 |
| 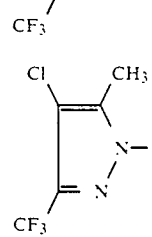 | F | 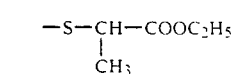 |

-continued
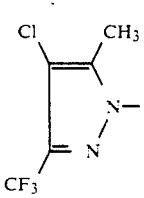 F 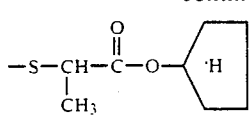
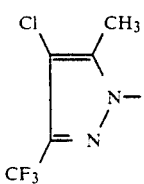 F 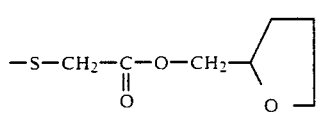
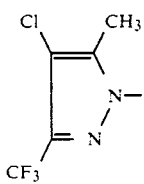 F 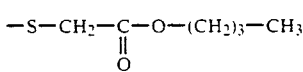
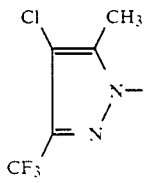 F 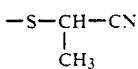
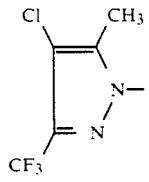 F 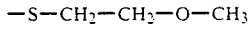
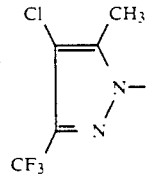 F 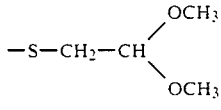
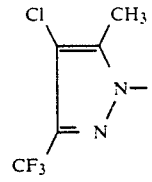 F 
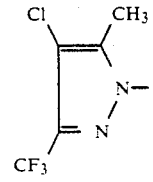 F 
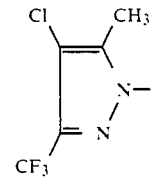 F 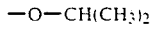

-continued
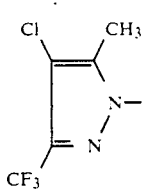   F   —O—CH$_2$—CH=CH$_2$
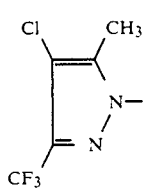   F   —O—CH$_2$—CH=CH—CH$_3$
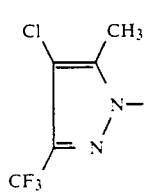   F   —O—CH$_2$—CH=CH—Cl
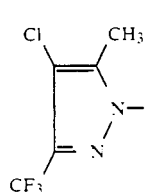   F   —O—CH—CH=CH$_2$
                             |
                             CH$_3$
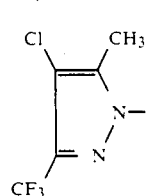   F   —O—CH$_2$—C≡CH
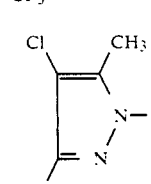   F   —O—CH—C≡CH
                             |
                             CH$_3$
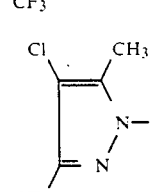   F   —O—CH$_2$—C=CH$_2$
                                     |
                                     CH$_3$
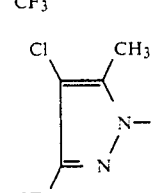   F   —O—CH$_2$—CH$_2$—OC$_2$H$_5$
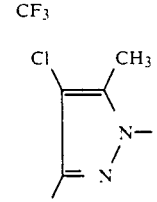   F   —O—CH—CH$_2$—OC$_2$H$_5$
                             |
                             CH$_3$ -continued
| | | |
|---|---|---|
| 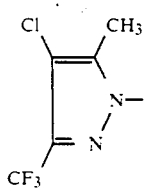 | F | —O—CH₂—CH—OCH₃<br>　　　　　\|<br>　　　　　CH₃ |
| 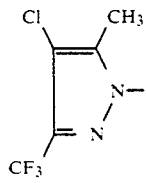 | F | 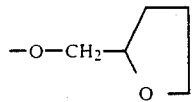 |
| 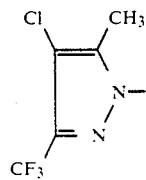 | F | 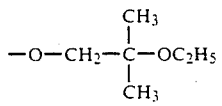 |
| 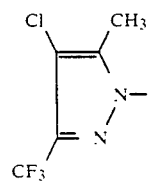 | F | —O—CH₂—CH₂—O—CH₂—CH₂—OCH₃ |
| 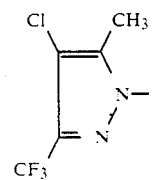 | F | —O—CH₂—CH₂—O—CH₂—CH₂—OC₂H₅ |
| 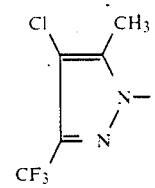 | F | 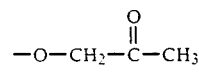 |
| 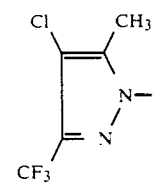 | F | 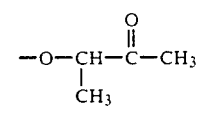 |
| 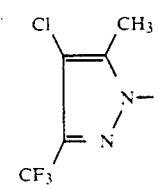 | F | —SCH₃ |
| 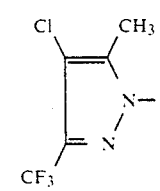 | F | —SC₂H₅ |

-continued
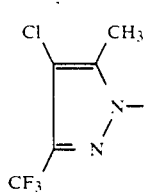 F —S—CH(CH₃)₂
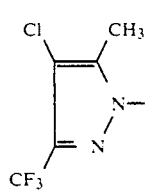 F —S—CH₂—CH=CH₂
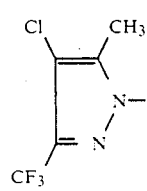 F —S—CH₂—CH=CH—Cl
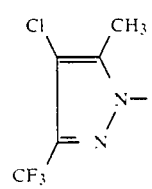 F —S—CH₂—CH=CH—CH₃
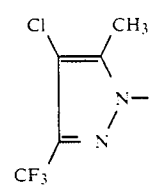 F —S—CH—CH=CH₂
         |
         CH₃
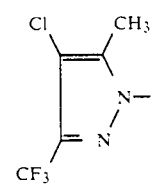 F —S—CH₂—C≡CH
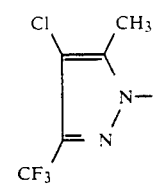 F —S—CH—C≡CH
         |
         CH₃
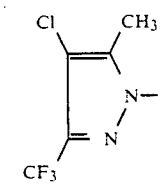 F —S—CH₂—C=CH₂
              |
              CH₃
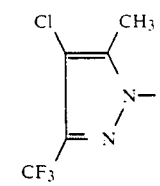 F —S—CH₂—CH₂—OC₂H₅

-continued
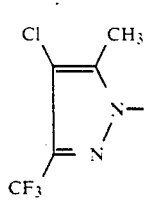 F 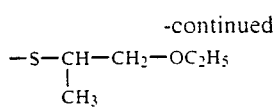
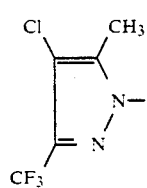 F 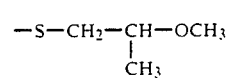
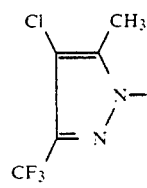 F 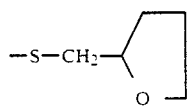
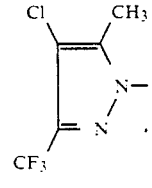 F 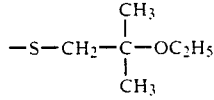
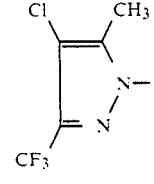 F 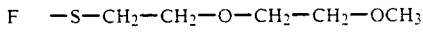
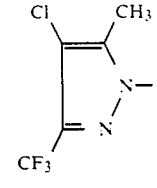 F 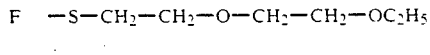
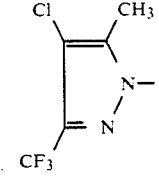 F 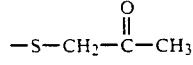
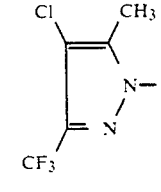 F 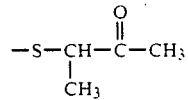
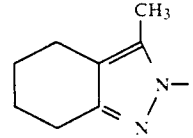 F 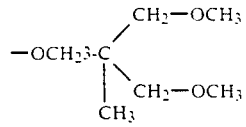

-continued
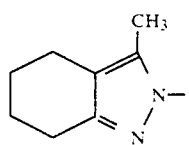 F 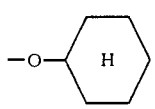
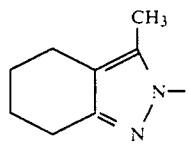 F 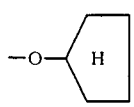
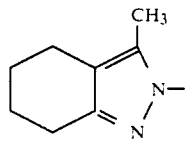 F 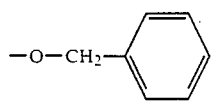
 F —O—CH₂—CN
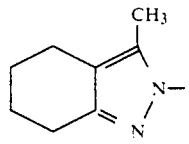 F —O—CH₂—COOC₂H₅
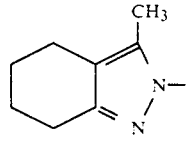 F 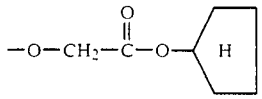
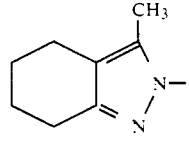 F —O—CH—COOC₂H₅
                        |
                        CH₃
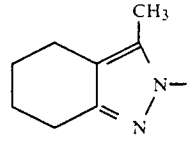 F 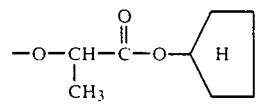
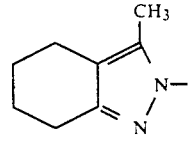 F 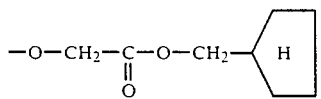
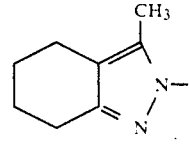 F —O—CH₂—C—O—(CH₂)₃—CH₃
                           ‖
                           O
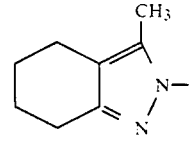 F —O—CH—CN
                         |
                         CH₃

-continued
| | | |
|---|---|---|
| 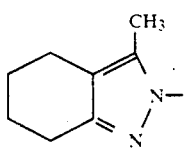 | F | —O—CH$_2$—CH$_2$—O—CH$_3$ |
| 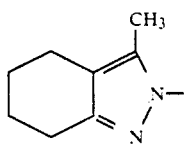 | F | 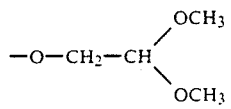 |
| 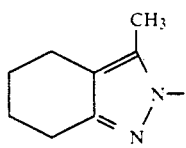 | F | 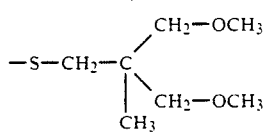 |
| 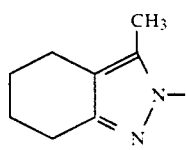 | F | 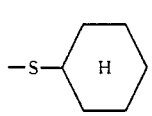 |
| 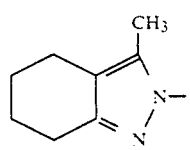 | F | 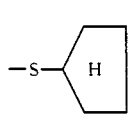 |
| 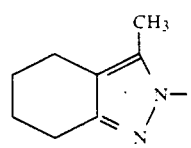 | F | —S—CH$_2$—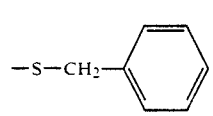 |
| 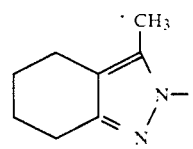 | F | —S—CH$_2$—CN |
| 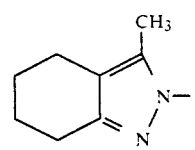 | F | —S—CH$_2$—COOC$_2$H$_5$ |
| 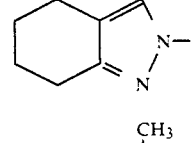 | F | 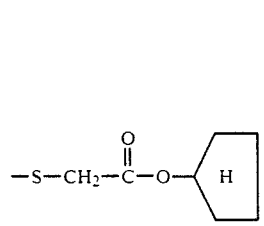 |
| 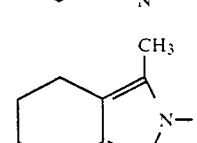 | F | 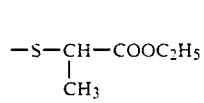 |
| 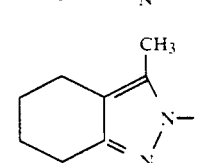 | F | 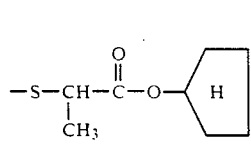 |

-continued
| | | |
|---|---|---|
| 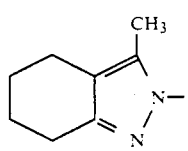 | F | 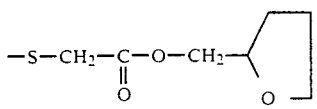 |
| 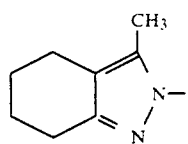 | F | −S−CH$_2$−C(=O)−O−(CH$_2$)$_3$−CH$_3$ |
| 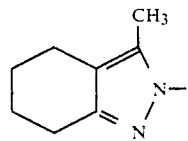 | F | −S−CH(CH$_3$)−CN |
| 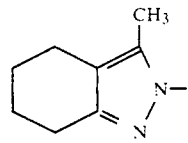 | F | −S−CH$_2$−CH$_2$−O−CH$_3$ |
| 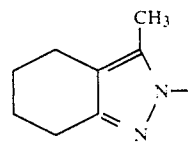 | F | −S−CH$_2$−CH(OCH$_3$)$_2$ |
| 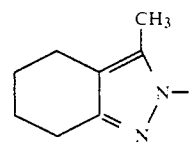 | F | −OCH$_3$ |
| 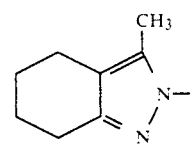 | F | −OC$_2$H$_5$ |
| 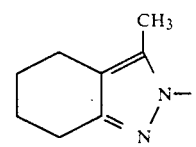 | F | −O−CH(CH$_3$)$_2$ |
| 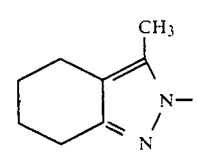 | F | −O−CH$_2$−CH≡CH$_2$ |
| 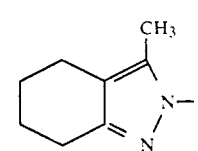 | F | −O−CH$_2$−CH=CH−CH$_3$ |
| 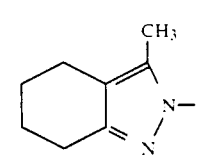 | F | −O−CH$_2$−CH=CH−Cl |

-continued
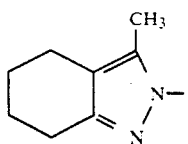 F 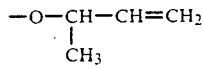
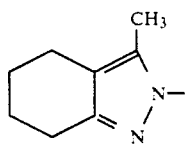 F 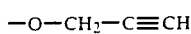
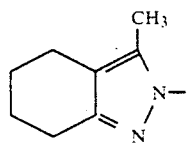 F 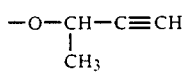
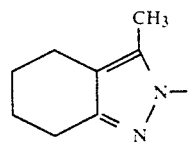 F 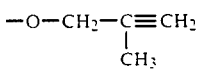
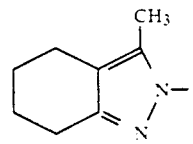 F 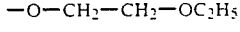
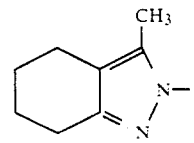 F 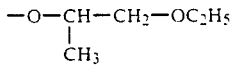
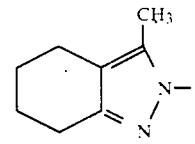 F 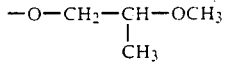
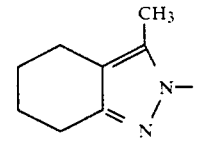 F 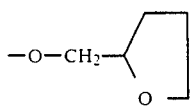
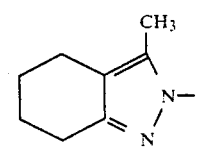 F 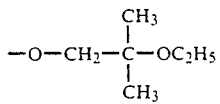
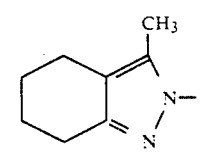 F 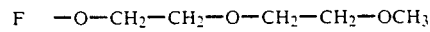
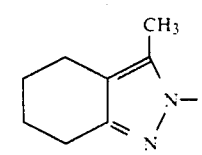 F 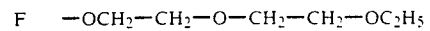

-continued
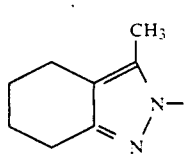 F $-O-CH_2-\overset{\overset{O}{\|}}{C}-CH_3$
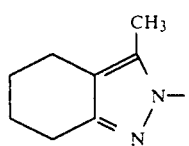 F $-O-\underset{\underset{CH_3}{|}}{CH}-\overset{\overset{O}{\|}}{C}-CH_3$
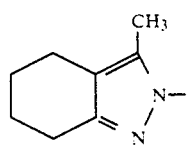 F $-SCH_3$
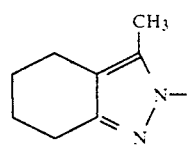 F $-SC_2H_5$
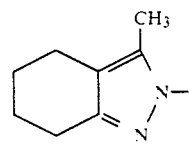 F $-S-CH(CH_3)_2$
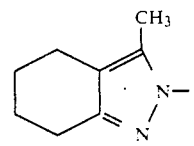 F $-S-CH_2-CH=CH_2$
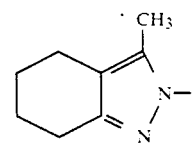 F $-S-CH_2-CH=CH-Cl$
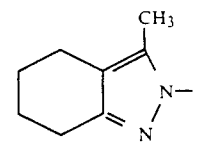 F $-S-CH_2-CH=CH-CH_3$
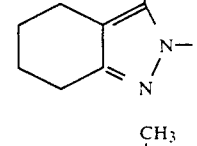 F $-S-\underset{\underset{CH_3}{|}}{CH}-CH=CH_2$
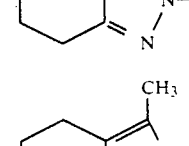 F $-S-CH_2-C\equiv CH$
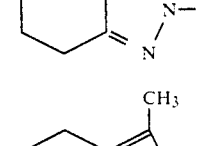 F $-S-\underset{\underset{CH_3}{|}}{CH}-C\equiv CH$ -continued
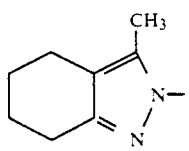 F 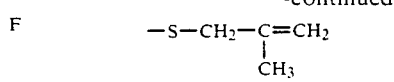
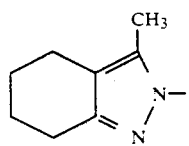 F —S—CH₂—CH₂—OC₂H₅
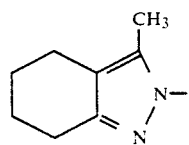 F 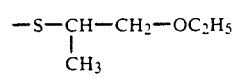
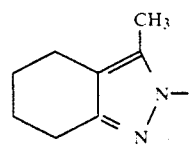 F 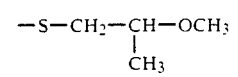
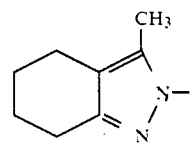 F 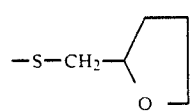
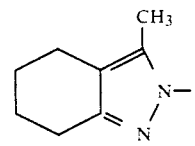 F —S—CH₂—CH₂—O—CH₂—CH₂—OCH₃
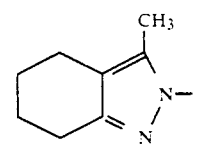 F —S—CH₂—CH₂—O—CH₂—CH₂—OC₂H₅
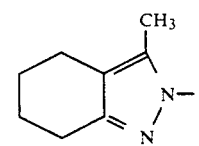 F 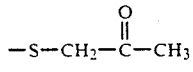
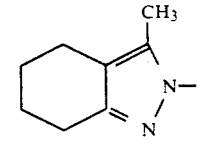 F 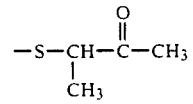
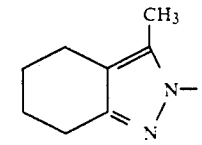 F 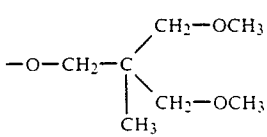

-continued
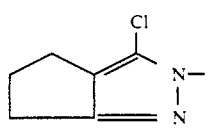 F 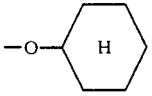
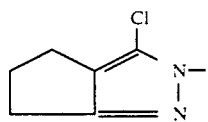 F 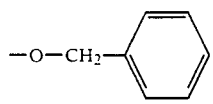
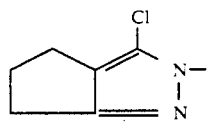 F 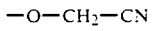
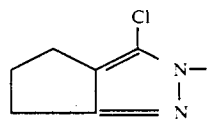 F —O—CH₂—CN
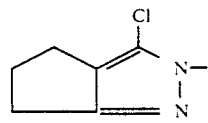 F —O—CH₂—COOCH₃
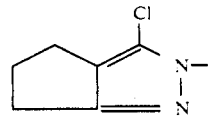 F —O—CH₂—COOC₂H₅
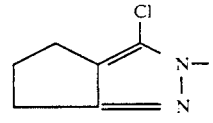 F 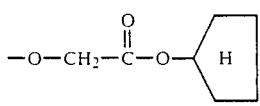
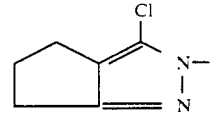 F —O—CH—COOC₂H₅
$\quad\quad\quad\quad\quad$ |
$\quad\quad\quad\quad\quad$ CH₃
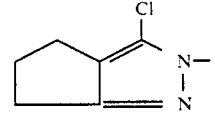 F 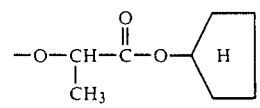
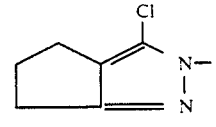 F 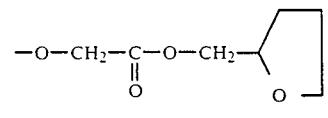
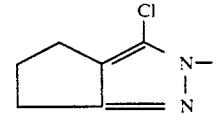 F —O—CH₂—C(=O)—O—(CH₂)₃—CH₃
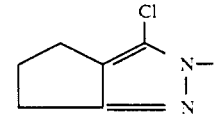 F —O—CH—CN
$\quad\quad\quad\quad$ |
$\quad\quad\quad\quad$ CH₃

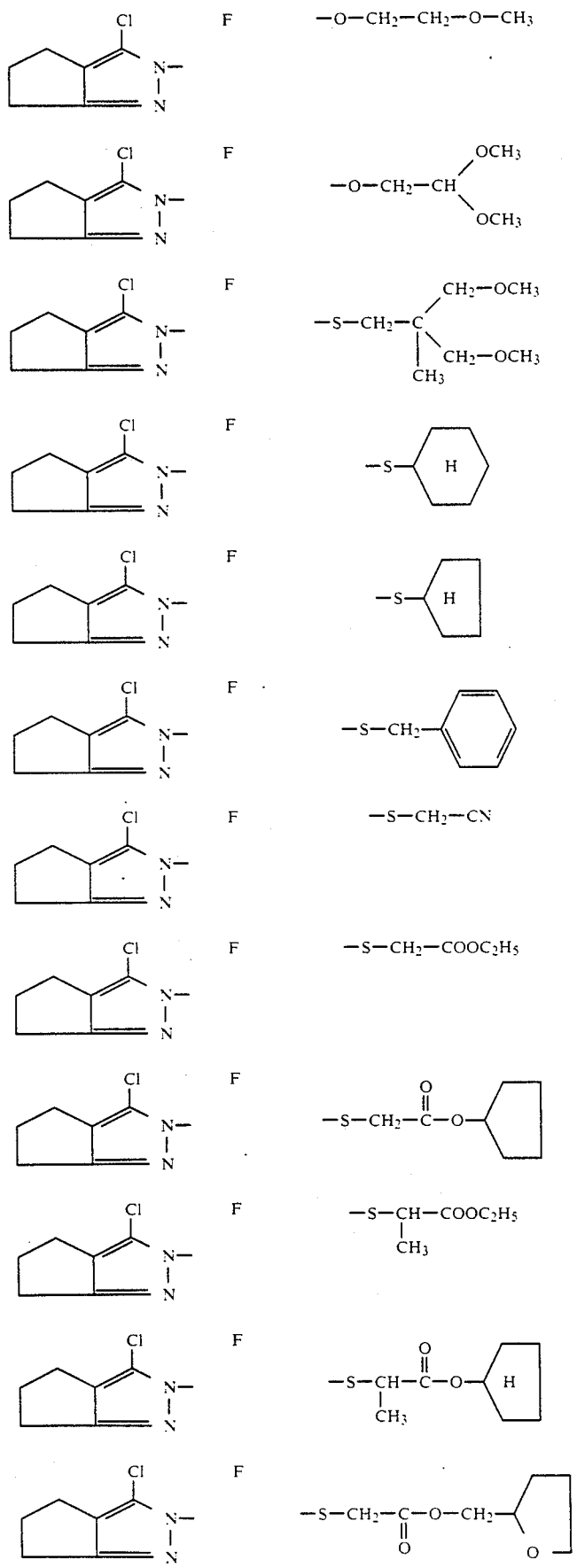

-continued
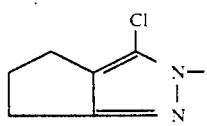 F 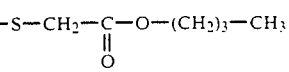
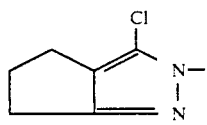 F 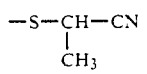
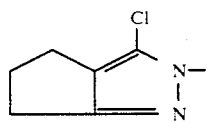 F —S—CH$_2$—CH$_2$—O—CH$_3$
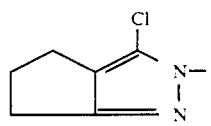 F 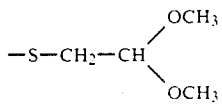
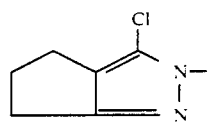 F —OCH$_3$
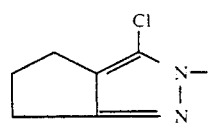 F —OC$_2$H$_5$
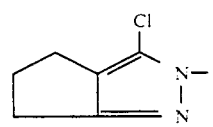 F —OCH(CH$_3$)$_2$
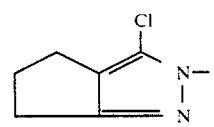 F —O—CH$_2$—CH=CH$_2$
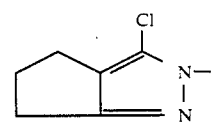 F —O—CH$_2$—CH=CH—CH$_3$
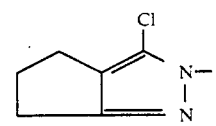 F —O—CH$_2$—CH=CH—Cl
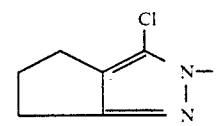 F 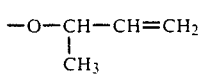
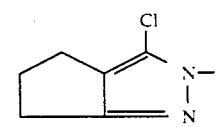 F —O—CH$_2$—C≡CH -continued
| | | |
|---|---|---|
| 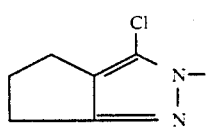 | F | 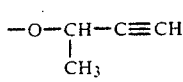 |
| 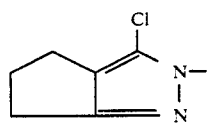 | F | 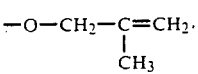 |
| 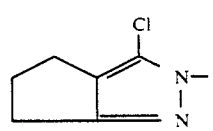 | F | —OCH₂—CH₂—OC₂H₅ |
| 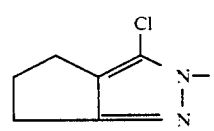 | F | 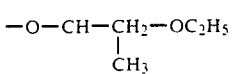 |
| 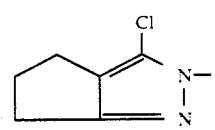 | F | 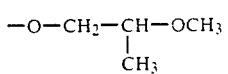 |
| 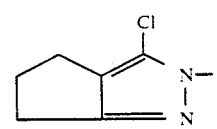 | F | 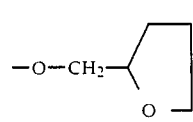 |
| 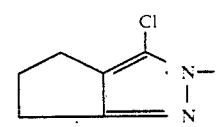 | F | 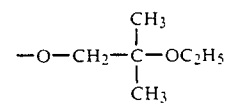 |
| 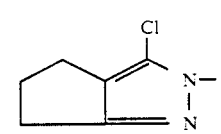 | F | —O—CH₂—CH₂—O—CH₂—CH₂—OCH₃ |
| 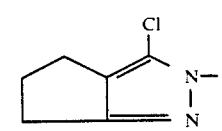 | F | —O—CH₂—CH₂—O—CH₂—CH₂—OC₂H₅ |
| 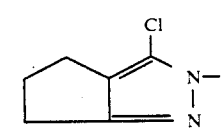 | F | 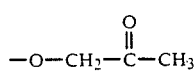 |
| 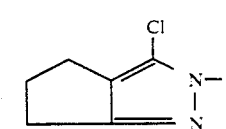 | F | 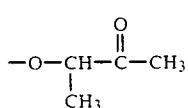 |
| 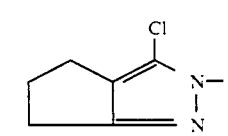 | F | —SCH₃ |

| Structure | | |
|---|---|---|
| cyclopentane-C(Cl)=N-N=CH- (fused pyrazole) | F | —SC₂H₅ |
| " | F | —S—CH(CH₃)₂ |
| " | F | —S—CH₂—CH=CH₂ |
| " | F | —S—CH₂—CH=CH—Cl |
| " | F | —S—CH₂—CH=CH—CH₃ |
| " | F | —S—CH(CH₃)—CH=CH₂ |
| " | F | —S—CH₂—C≡CH |
| " | F | —S—CH(CH₃)—C≡CH |
| " | F | —S—CH₂—C(CH₃)=CH₂ |
| " | F | —S—CH₂—CH₂—OC₂H₅ |
| " | F | —S—CH(CH₃)—CH₂—OC₂H₅ |
| " | F | —S—CH₂—CH(CH₃)—OCH₃ |

-continued
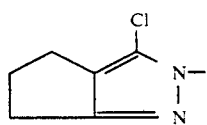 F 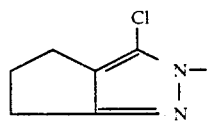
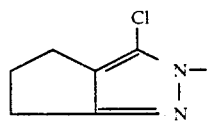 F 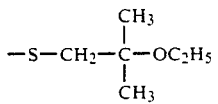
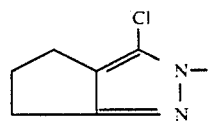 F —S—CH₂—CH₂—O—CH₂—CH₂—OCH₃
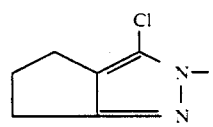 F —S—CH₂—CH₂—O—CH₂—CH₂—OC₂H₅
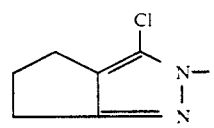 F 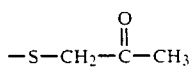
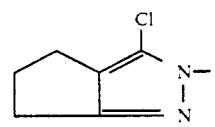 F 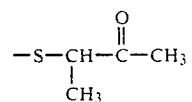
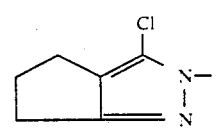 H 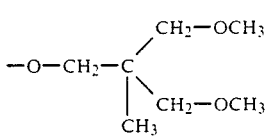
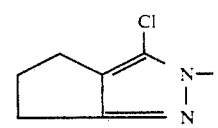 H 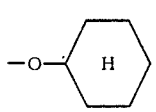
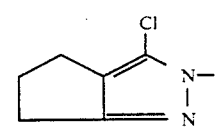 H 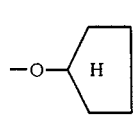
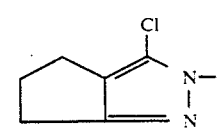 H 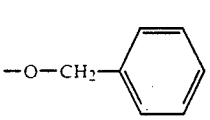
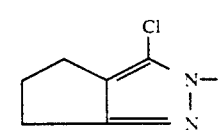 H —O—CH₂—CN
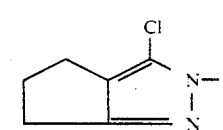 H —O—CH₂—COOC₂H₅

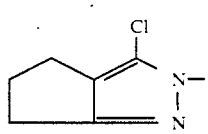 H 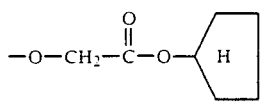
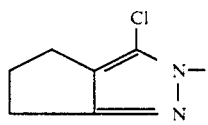 H 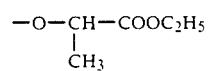
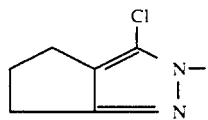 H 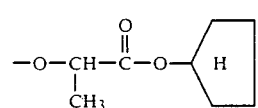
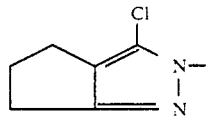 H 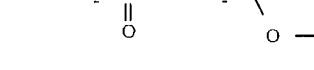
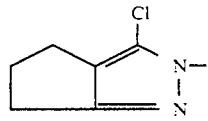 H 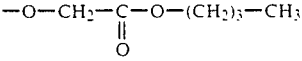
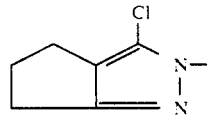 H 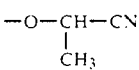
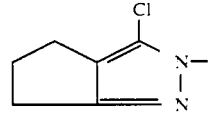 H —O—CH$_2$—CH$_2$—O—CH$_3$
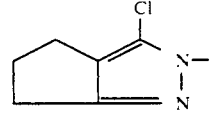 H 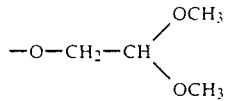
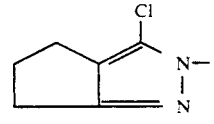 H 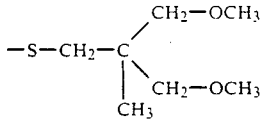
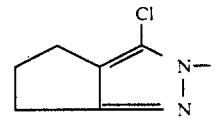 H 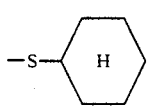
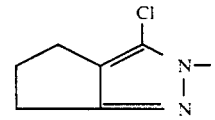 H 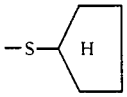
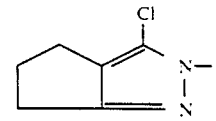 H 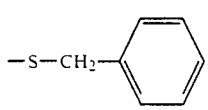

-continued
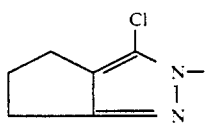 H 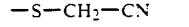
—S—CH₂—CN
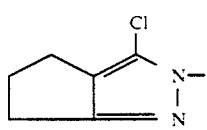 H 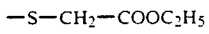
—S—CH₂—COOC₂H₅
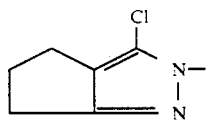 H 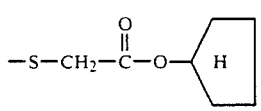
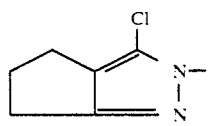 H 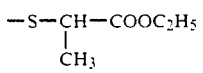
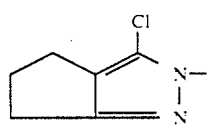 H 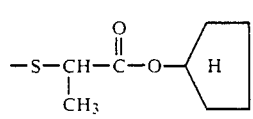
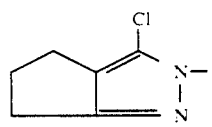 H 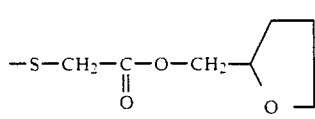
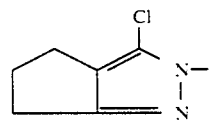 H 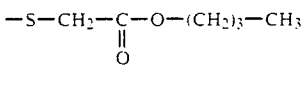
—S—CH₂—C(=O)—O—(CH₂)₃—CH₃
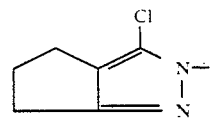 H 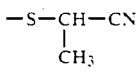
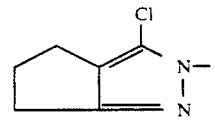 H 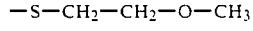
—S—CH₂—CH₂—O—CH₃
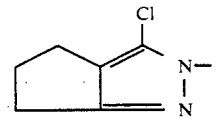 H 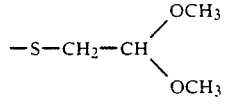
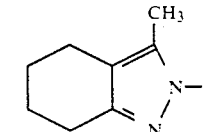 H 
—OCH₃
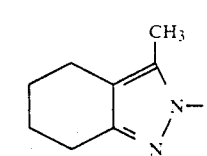 H 
—OC₂H₅

-continued
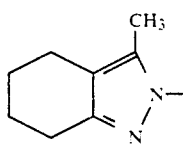 H —O—CH(CH₃)₂
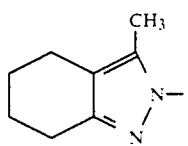 H —O—CH₂—CH=CH₂
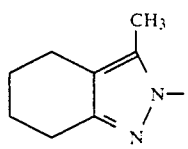 H —O—CH₂—CH=CH—CH₃
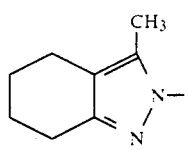 H —O—CH₂—CH=CH—Cl
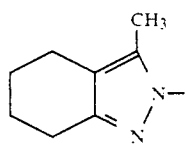 H —O—CH—CH=CH₂
                      |
                      CH₃
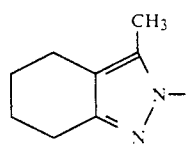 H —O—CH₂—C≡CH
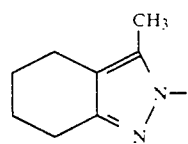 H —O—CH—C≡CH
                      |
                      CH₃
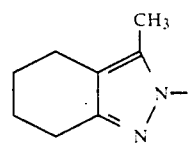 H —O—CH₂—C=CH₂
                      |
                      CH₃
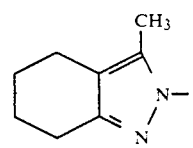 H —O—CH₂—CH₂—OC₂H₅
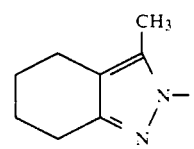 H   CH₃
                         |
                    —O—CH—CH₂—OC₂H₅
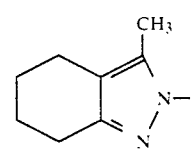 H —O—CH₂—CH—OCH₃
                              |
                              CH₃

-continued
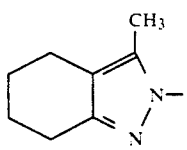 H 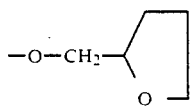
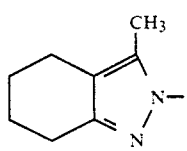 H 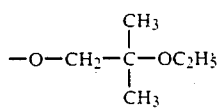
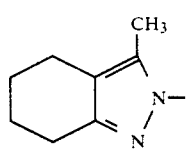 H —O—CH$_2$—CH$_2$—O—CH$_2$—CH$_2$—OCH$_3$
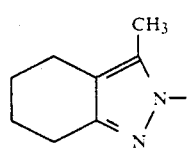 H —O—CH$_2$—CH$_2$—O—CH$_2$—CH$_2$—OC$_2$H$_5$
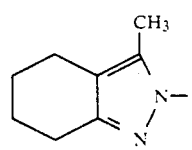 H 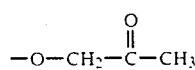
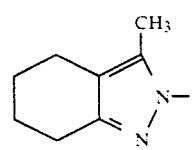 H 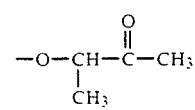
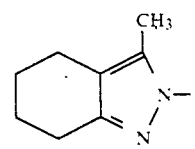 H —SCH$_3$
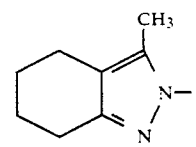 H —SC$_2$H$_5$
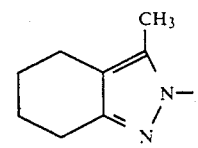 H —S—CH(CH$_3$)$_2$
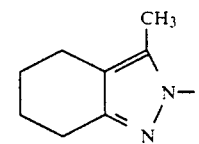 H —S—CH$_2$—CH=CH$_2$
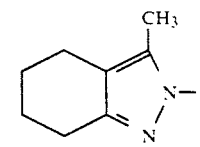 H —S—CH$_2$—CH=CH—Cl -continued
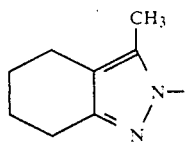 H 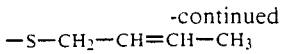
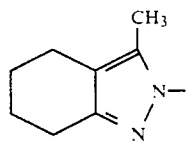 H 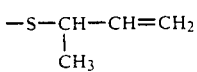
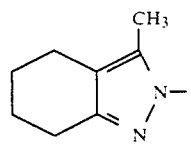 H —S—CH$_2$—C≡CH
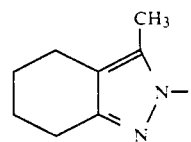 H 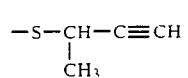
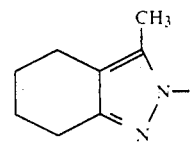 H 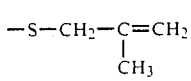
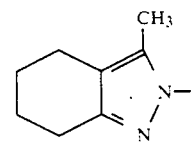 H —S—CH$_2$—CH$_2$—OC$_2$H$_5$
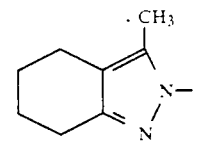 H 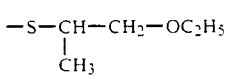
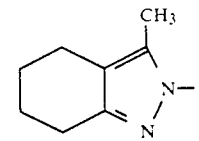 H 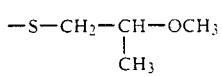
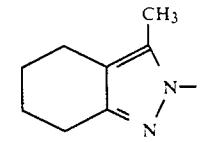 H 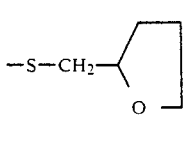
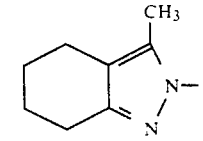 H 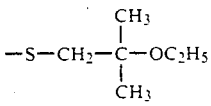
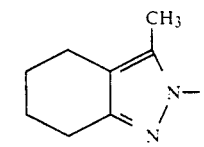 H —S—CH$_2$—CH$_2$—O—CH$_2$—CH$_2$—OCH$_3$ -continued
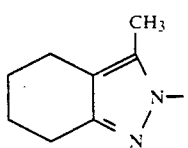 H 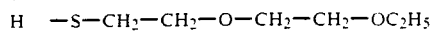
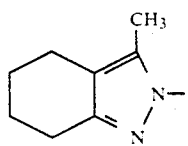 H 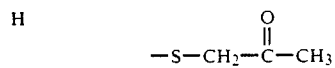
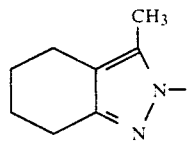 H 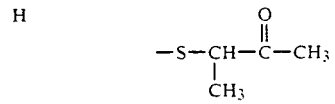
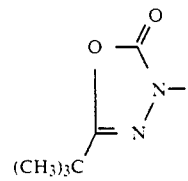 F 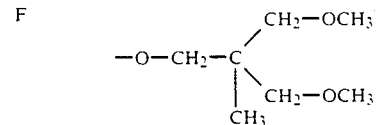
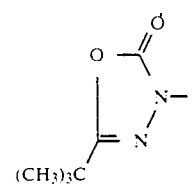 F 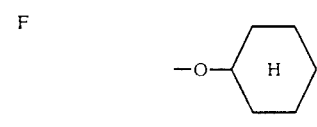
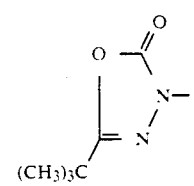 F 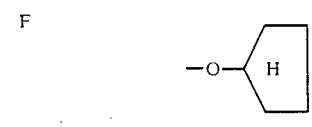
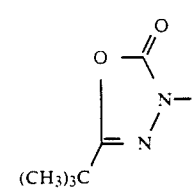 F 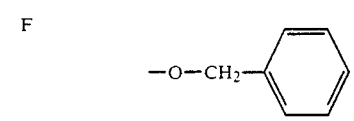
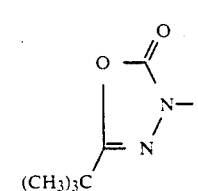 F 
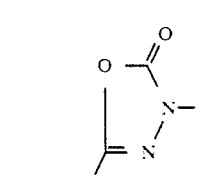 F 

-continued
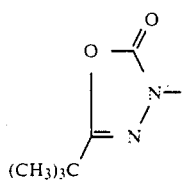 F 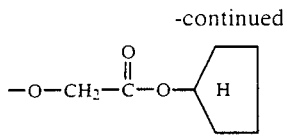
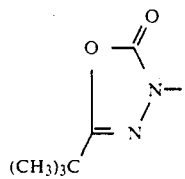 F 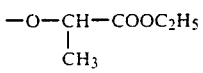
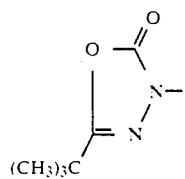 F 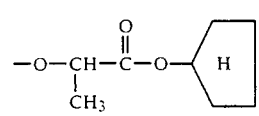
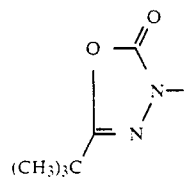 F 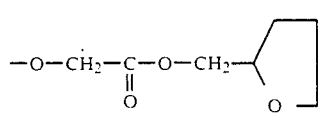
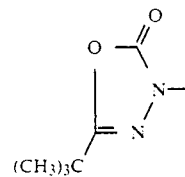 F 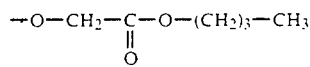
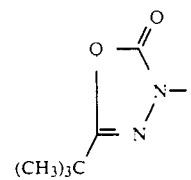 F 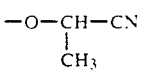
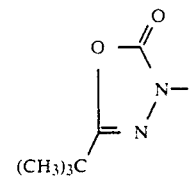 F 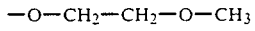
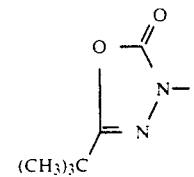 F 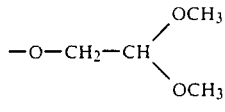

-continued
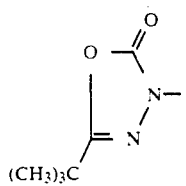 F 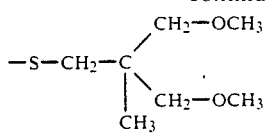
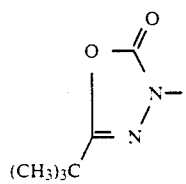 F 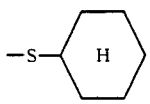
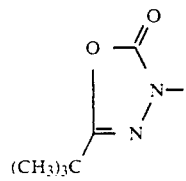 F 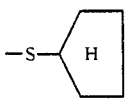
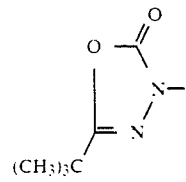 F 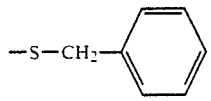
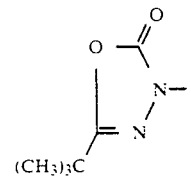 F 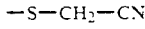
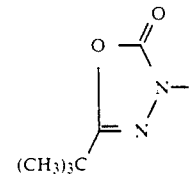 F 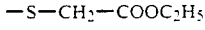
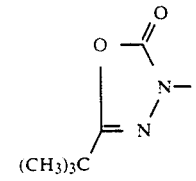 F 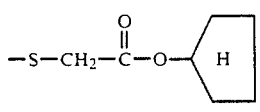
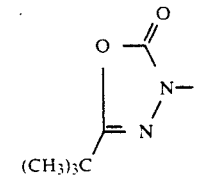 F 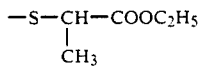
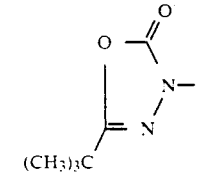 F 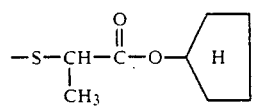

-continued
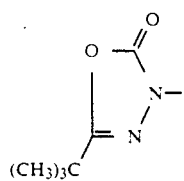 F 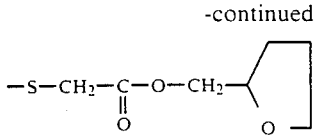
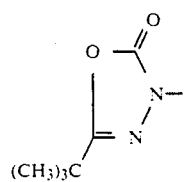 F 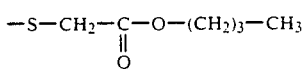
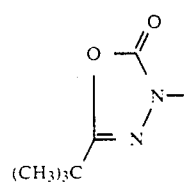 F 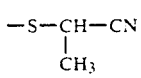
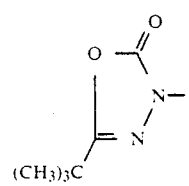 F —S—CH$_2$—CH$_2$—O—CH$_3$
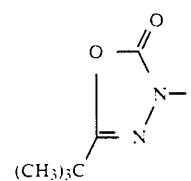 F 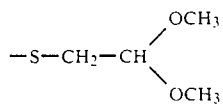
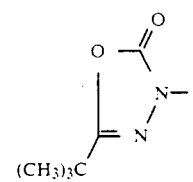 F —OCH$_3$
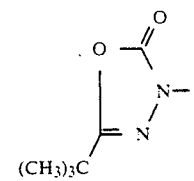 F —OC$_2$H$_5$
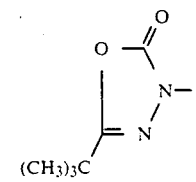 F —O—CH(CH$_3$)$_2$
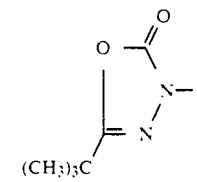 F —O—CH$_2$—CH=CH$_2$ -continued
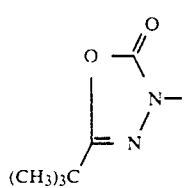 F —O—CH₂—CH=CH—CH₃
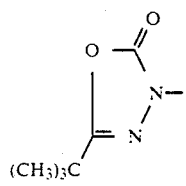 F —O—CH₂—CH=CH—Cl
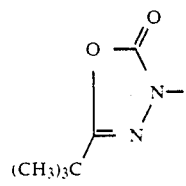 F —O—CH—CH=CH₂
                          |
                          CH₃
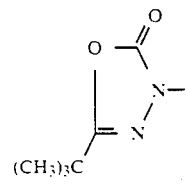 F —O—CH₂—C≡CH
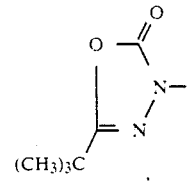 F —O—CH—C≡CH
                          |
                          CH₃
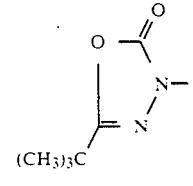 F —O—CH₂—C=CH₂
                           |
                           CH₃
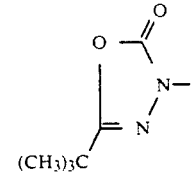 F —O—CH₂—CH₂—OC₂H₅
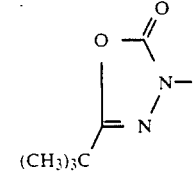 F —O—CH—CH₂—OC₂H₅
                           |
                           CH₃
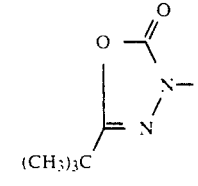 F —O—CH₂—CH—OCH₃
                                |
                                CH₃

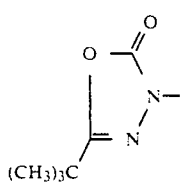 F 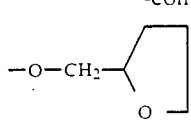
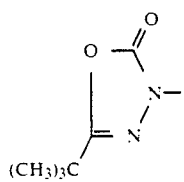 F 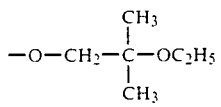
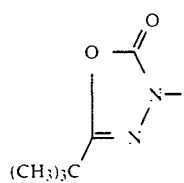 F —O—CH$_2$—CH$_2$—O—CH$_2$—CH$_2$—OCH$_3$
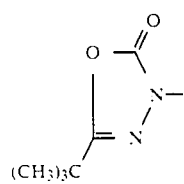 F —O—CH$_2$—CH$_2$—O—CH$_2$—CH$_2$—OC$_2$H$_5$
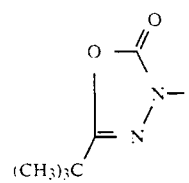 F 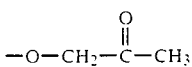
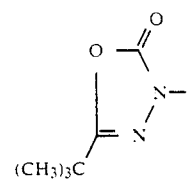 F 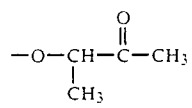
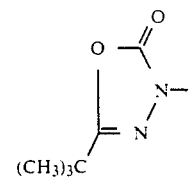 F —SCH$_3$
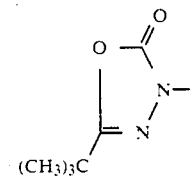 F —SC$_2$H$_5$
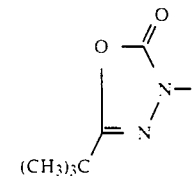 F —S—CH(CH$_3$)$_2$ -continued
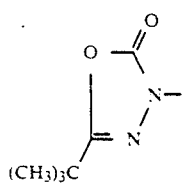 F  —S—CH₂—CH=CH₂
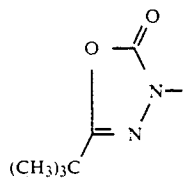 F  —S—CH₂—CH=CH—Cl
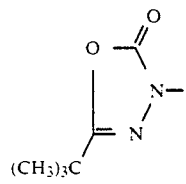 F  —S—CH₂—CH=CH—CH₃
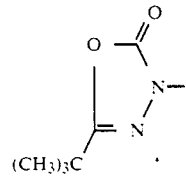 F  —S—CH—CH=CH₂
                              |
                              CH₃
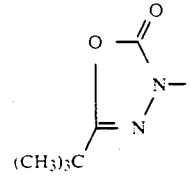 F  —S—CH₂—C≡CH
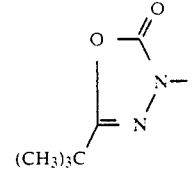 F  —S—CH—C≡CH
                              |
                              CH₃
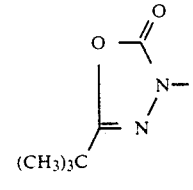 F  —S—CH₂—C=CH₂
                                |
                                CH₃
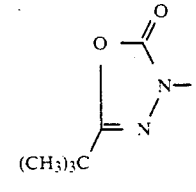 F  —S—CH₂—CH₂—OC₂H₅
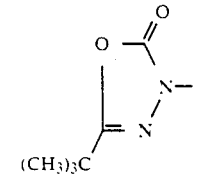 F  —S—CH—CH₂—OC₂H₅
                              |
                              CH₃

-continued
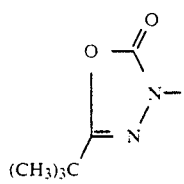 F 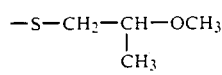
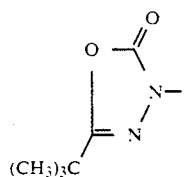 F 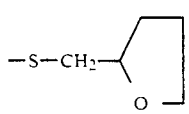
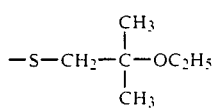 F 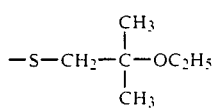
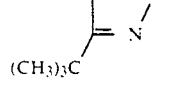 F —S—CH$_2$—CH$_2$—O—CH$_2$—CH$_2$—OCH$_3$
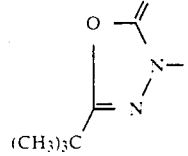 F —S—CH$_2$—CH$_2$—O—CH$_2$—CH$_2$—OC$_2$H$_5$
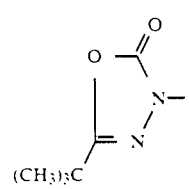 F 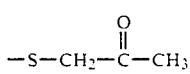
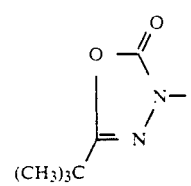 F 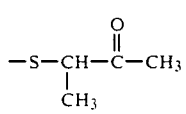
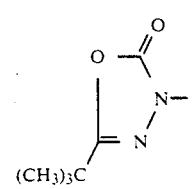 F 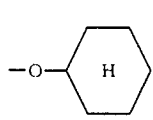

-continued
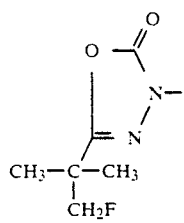 F 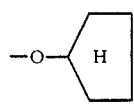
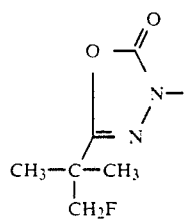 F 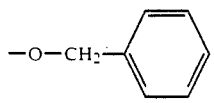
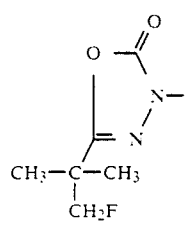 F —O—CH₂—CN
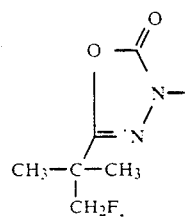 F —O—CH₂—COOC₂H₅
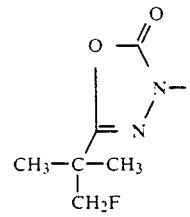 F 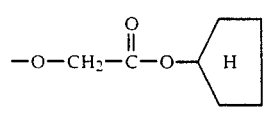
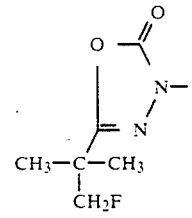 F 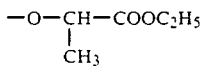
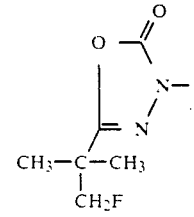 F 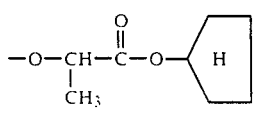

-continued
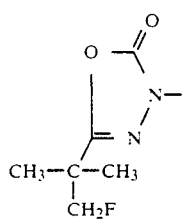 F 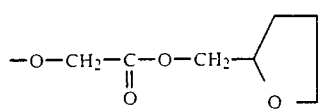
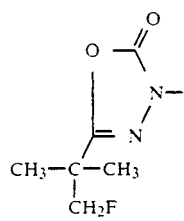 F 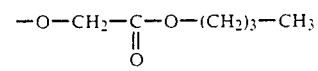
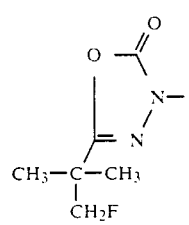 F 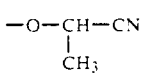
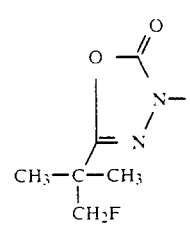 F 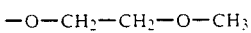
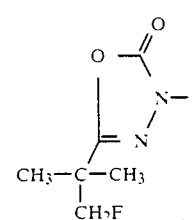 F 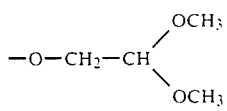
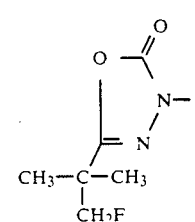 F 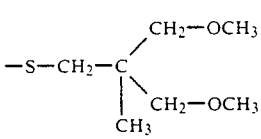
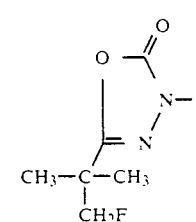 F 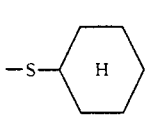

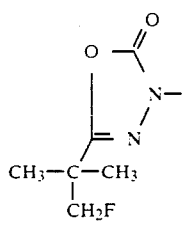 F 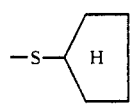
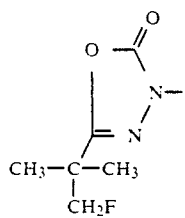 F 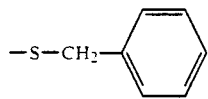
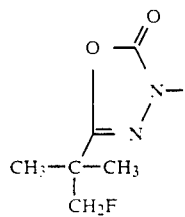 F —S—CH$_2$—CN
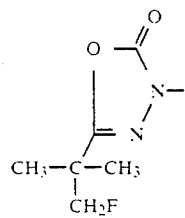 F —S—CH$_2$—COOC$_2$H$_5$
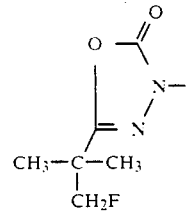 F 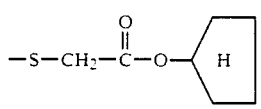
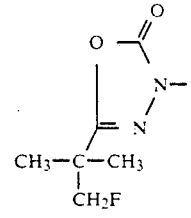 F 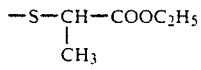
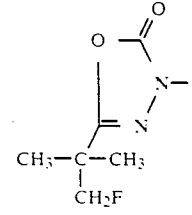 F 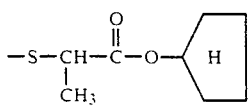

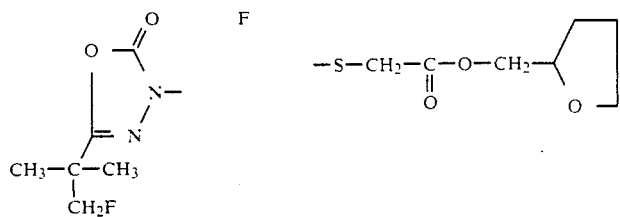 F —S—CH₂—C—O—CH₂—[tetrahydrofuran]
                        ‖
                        O
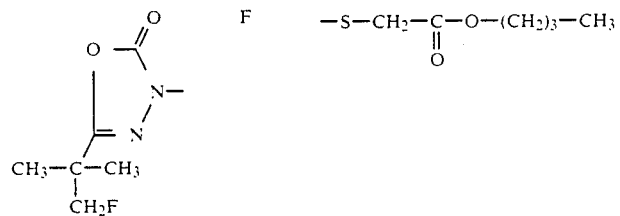 F —S—CH₂—C—O—(CH₂)₃—CH₃
                        ‖
                        O
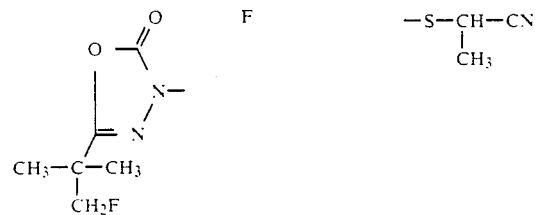 F —S—CH—CN
                        |
                        CH₃
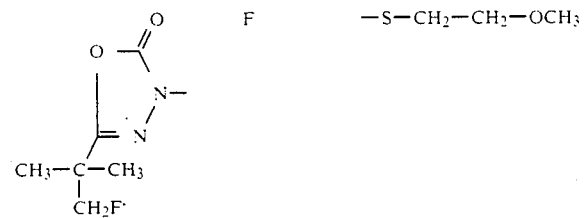 F —S—CH₂—CH₂—OCH₃
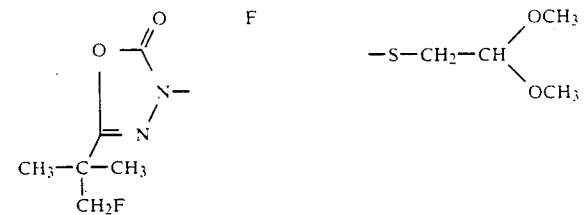 F —S—CH₂—CH(OCH₃)₂
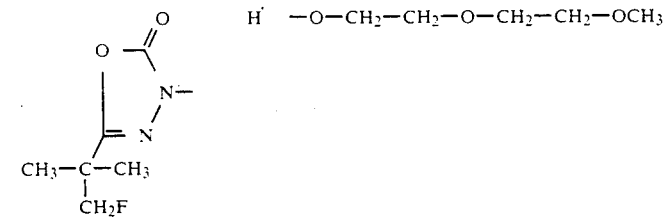 H —O—CH₂—CH₂—O—CH₂—CH₂—OCH₃
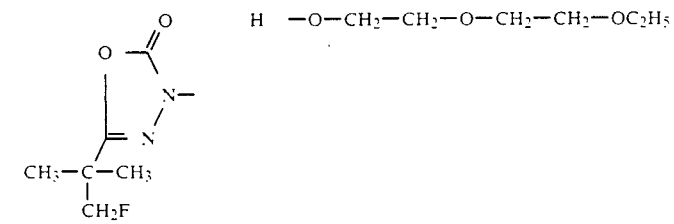 H —O—CH₂—CH₂—O—CH₂—CH₂—OC₂H₅

-continued
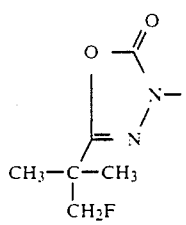 H 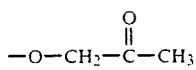
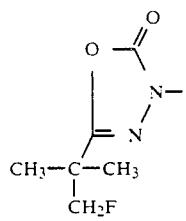 H 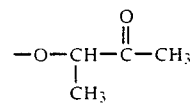
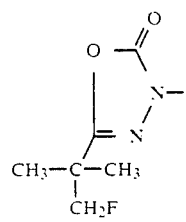 H —SCH₃
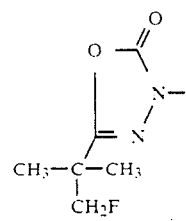 H —SC₂H₅
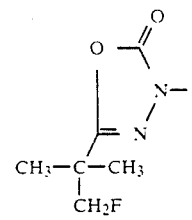 H —S—CH(CH₃)₂
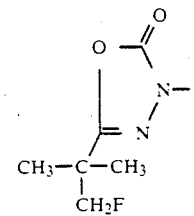 H —S—CH₂—CH=CH₂
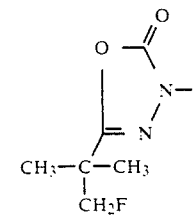 H —S—CH₂—CH=CH—Cl -continued
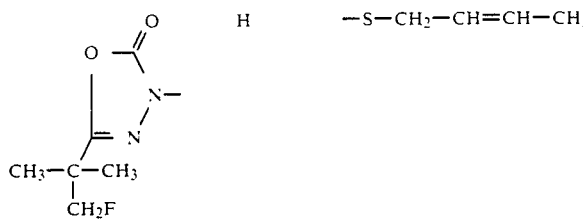 H —S—CH₂—CH=CH—CH₃
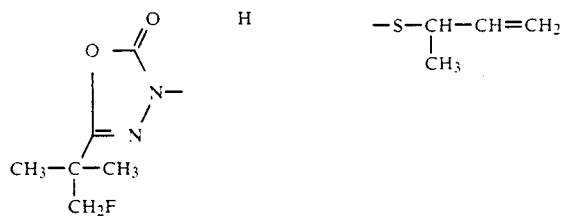 H —S—CH—CH=CH₂
                                |
                                CH₃
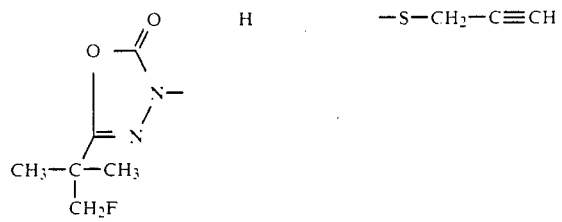 H —S—CH₂—C≡CH
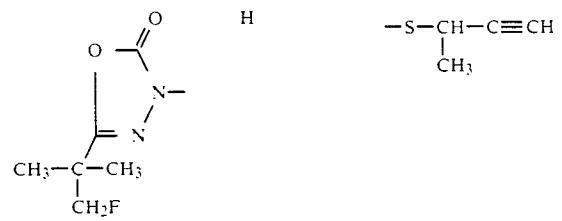 H —S—CH—C≡CH
                                |
                                CH₃
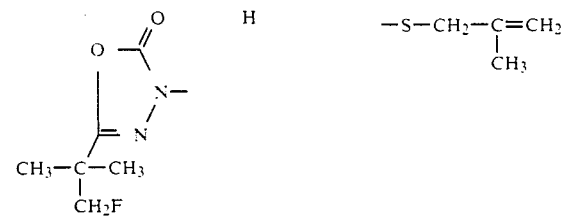 H —S—CH₂—C=CH₂
                                |
                                CH₃
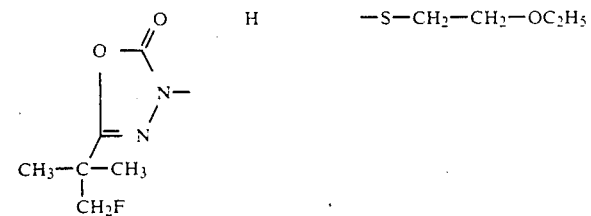 H —S—CH₂—CH₂—OC₂H₅
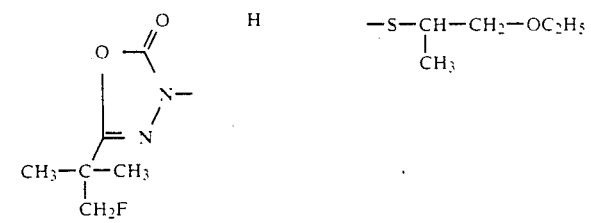 H —S—CH—CH₂—OC₂H₅
                                |
                                CH₃

-continued
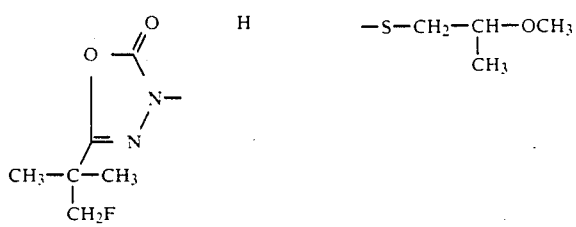 H —S—CH₂—CH—OCH₃
                              |
                              CH₃
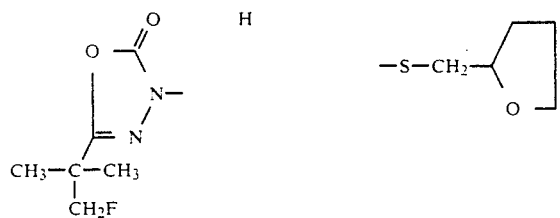 H —S—CH₂—⟨tetrahydrofuran⟩
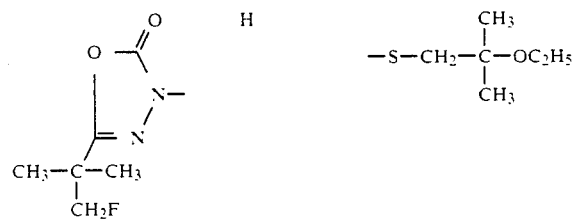 H     CH₃
                     |
          —S—CH₂—C—OC₂H₅
                     |
                     CH₃
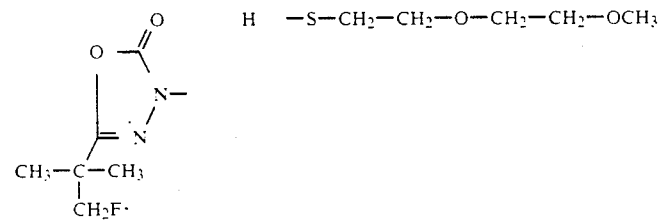 H —S—CH₂—CH₂—O—CH₂—CH₂—OCH₃
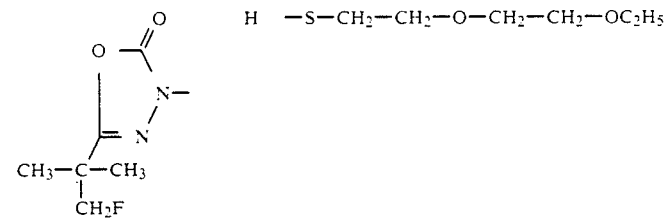 H —S—CH₂—CH₂—O—CH₂—CH₂—OC₂H₅
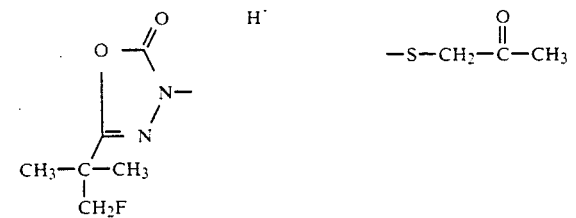 H           O
                                 ‖
                     —S—CH₂—C—CH₃
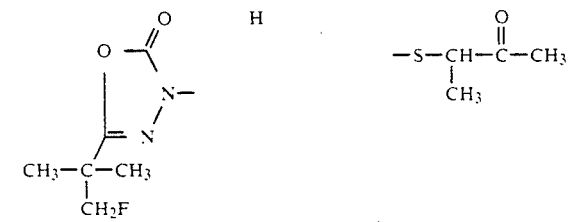 H           O
                                 ‖
                     —S—CH—C—CH₃
                          |
                          CH₃

-continued
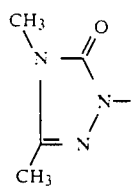 F 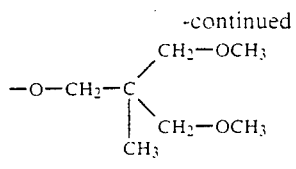
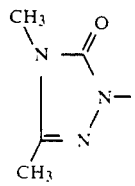 F 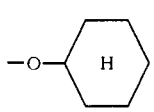
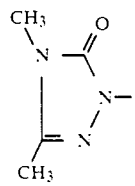 F 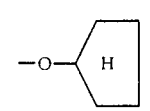
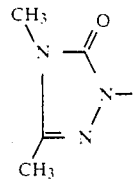 F 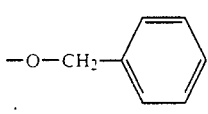
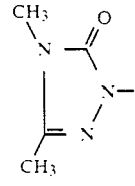 F —O—CH₂—CN
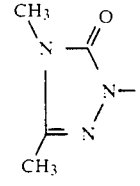 F —O—CH₂—COOC₂H₅
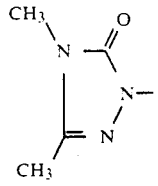 F 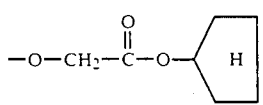
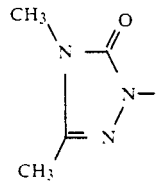 F —O—CH—COOC₂H₅
　　　　　　　　　|
　　　　　　　　　CH₃

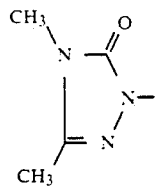 F 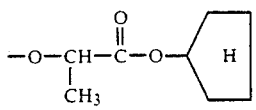
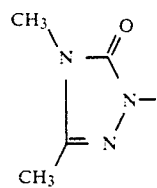 F 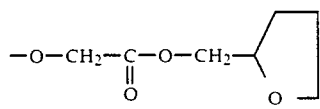
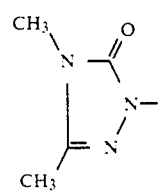 F 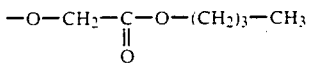
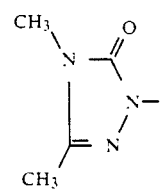 F 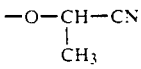
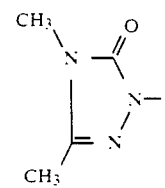 F 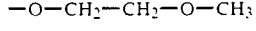
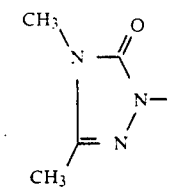 F 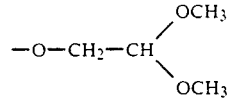
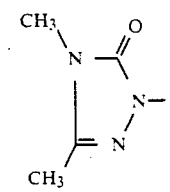 F 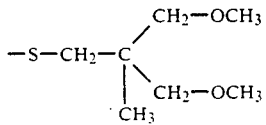
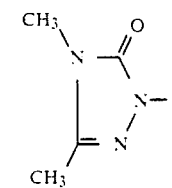 F 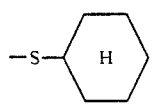

-continued
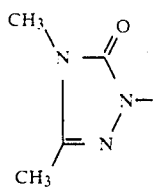 F 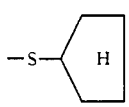
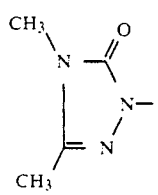 F 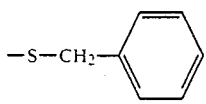
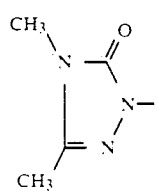 F 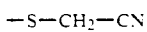
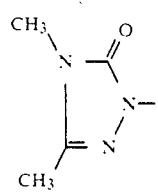 F 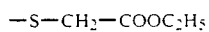
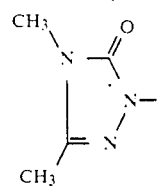 F 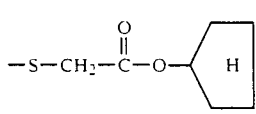
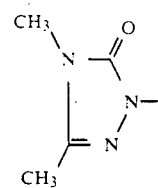 F 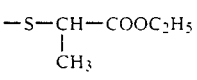
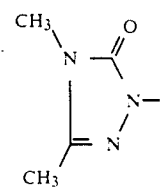 F 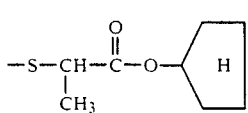
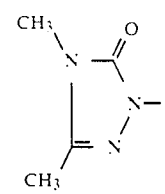 F 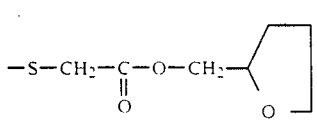

-continued
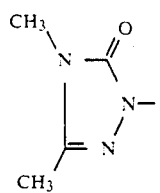 F 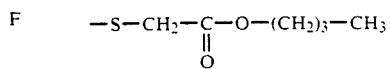
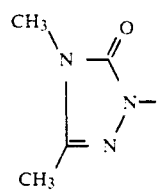 F 
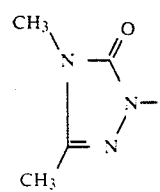 F —S—CH₂—CH₂—O—CH₃
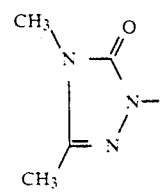 F 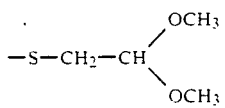
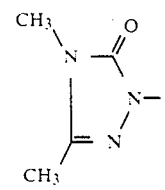 F —OCH₃
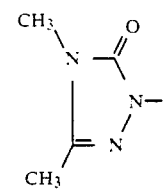 F —OC₂H₅
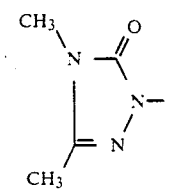 F —O—CH(CH₃)₂
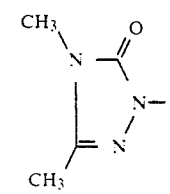 F —O—CH₂—CH=CH₂

-continued
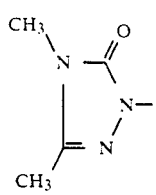 F 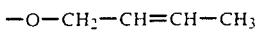
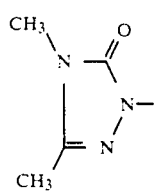 F —O—CH$_2$—CH=CH—Cl
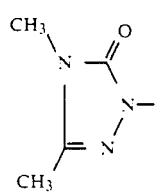 F 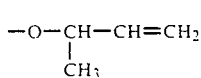
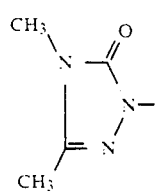 F —O—CH$_2$—C≡CH
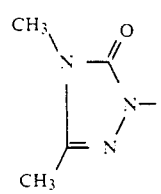 F 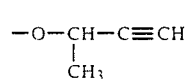
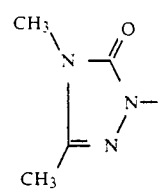 F 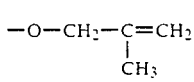
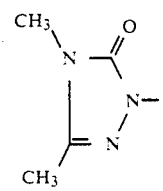 F —O—CH$_2$—CH$_2$—OC$_2$H$_5$
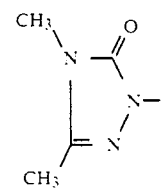 F 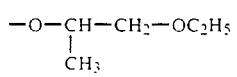

-continued
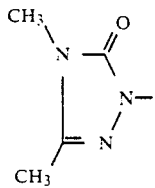 F $-O-CH_2-CH-OCH_3$
  $\phantom{-O-CH_2-}|$
  $\phantom{-O-CH_2-}CH_3$
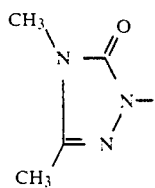 F 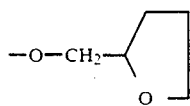
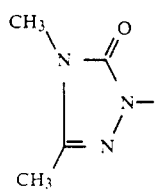 F $-O-CH_2-\underset{\underset{CH_3}{|}}{\overset{\overset{CH_3}{|}}{C}}-OC_2H_5$
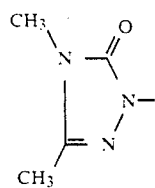 F $-O-CH_2-CH_2-O-CH_2-CH_2-OCH_3$
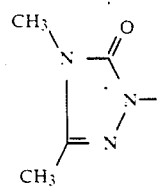 F $-O-CH_2-CH_2-O-CH_2-CH_2-OC_2H_5$
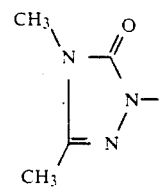 F $-O-CH_2-\overset{\overset{O}{\|}}{C}-CH_3$
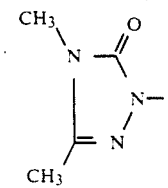 F $-O-\underset{\underset{CH_3}{|}}{CH}-\overset{\overset{O}{\|}}{C}-CH_3$
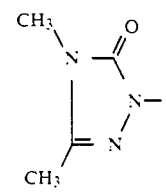 F $-SCH_3$

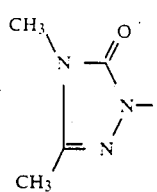   F   —SC$_2$H$_5$
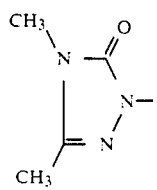   F   —S—CH(CH$_3$)$_2$
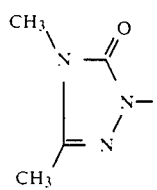   F   —S—CH$_2$—CH=CH$_2$
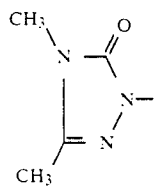   F   —S—CH$_2$—CH=CH—Cl
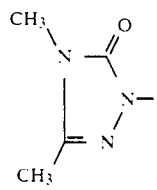   F   —S—CH$_2$—CH=CH—CH$_3$
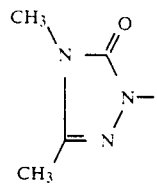   F   —S—CH—CH=CH$_2$
                           |
                           CH$_3$
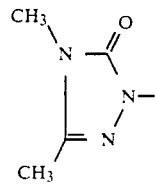   F   —S—CH$_2$—C≡CH
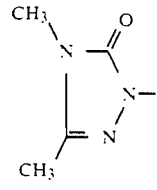   F   —S—CH—C≡CH
                           |
                           CH$_3$ -continued
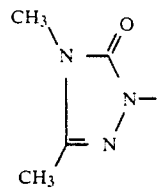 F 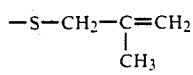
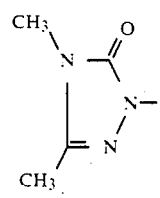 F —S—CH$_2$—CH$_2$—OC$_2$H$_5$
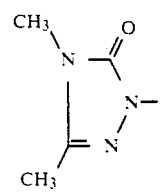 F 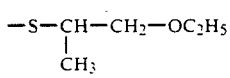
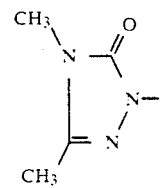 F 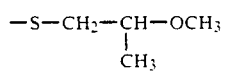
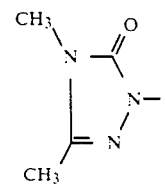 F 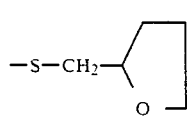
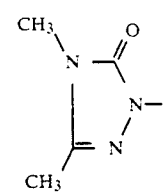 F 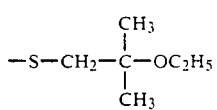
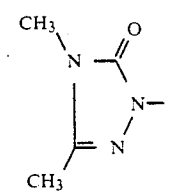 F —S—CH$_2$—CH$_2$—O—CH$_2$—CH$_2$—OCH$_3$
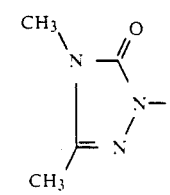 F —S—CH$_2$—CH$_2$—O—CH$_2$—CH$_2$—OC$_2$H$_5$ -continued
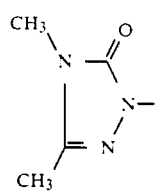 F 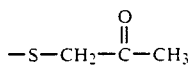
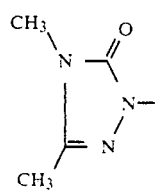 F 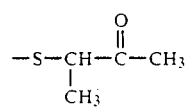
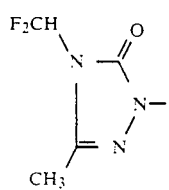 F 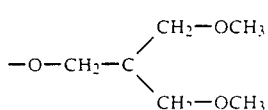
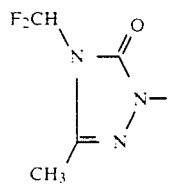 F 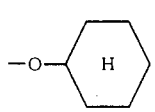
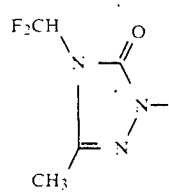 F 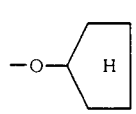
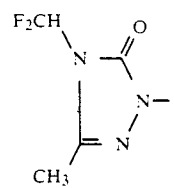 F 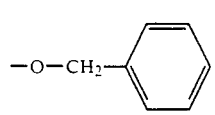
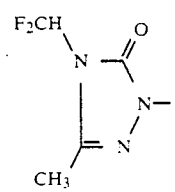 F —O—CH$_2$—CN
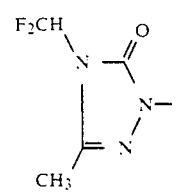 F —O—CH$_2$—COOC$_2$H$_5$ -continued
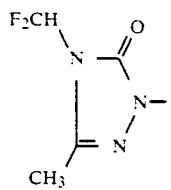 F 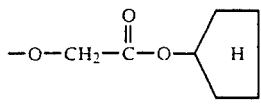
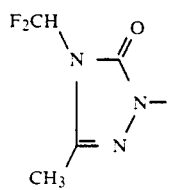 F 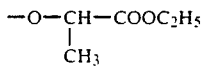
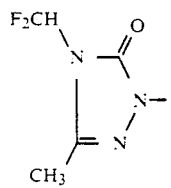 F 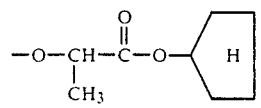
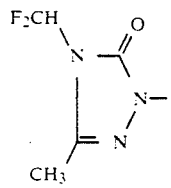 F 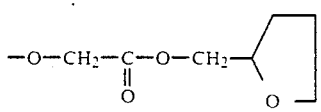
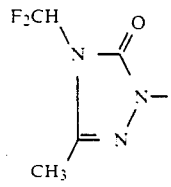 F 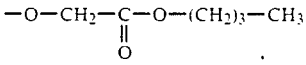
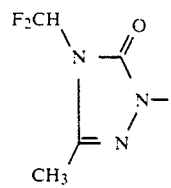 F 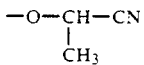
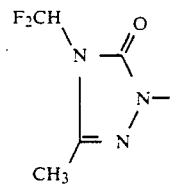 F 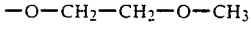
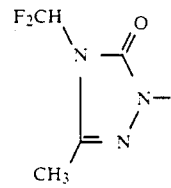 F 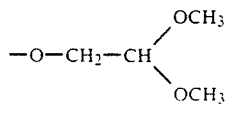

-continued
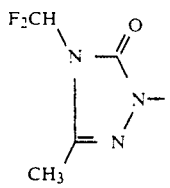 H 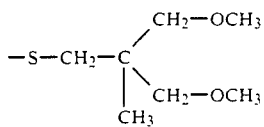
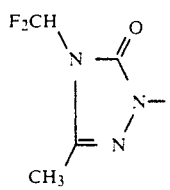 H 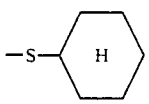
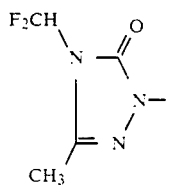 H 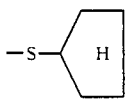
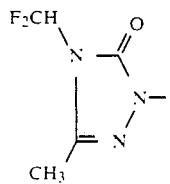 H 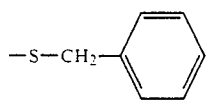
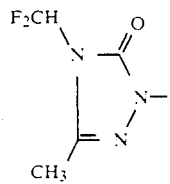 H 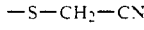
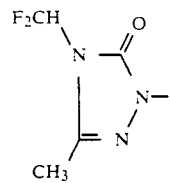 H 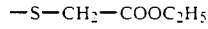
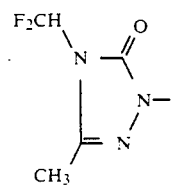 H 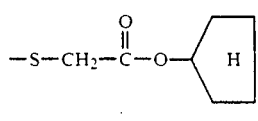
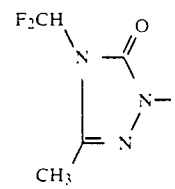 H 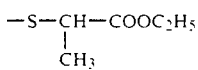

-continued
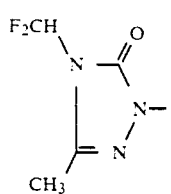 H 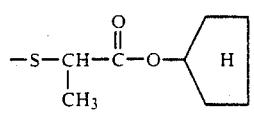
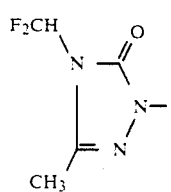 H 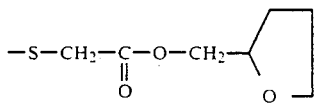
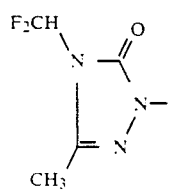 H 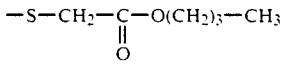
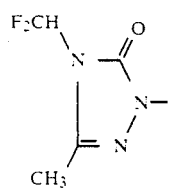 H 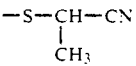
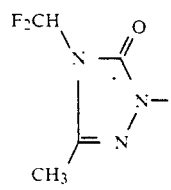 H 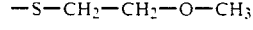
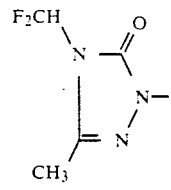 H 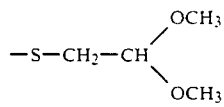
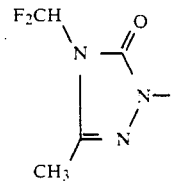 F —OCH$_3$
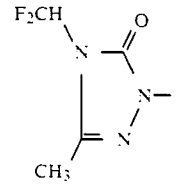 F —OC$_2$H$_5$ -continued
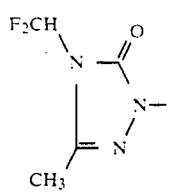 F —O—CH(CH$_3$)$_2$
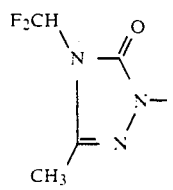 F —O—CH$_2$—C≡CH$_2$
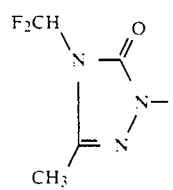 F —O—CH$_2$—CH=CH—CH$_3$
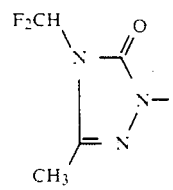 F —O—CH$_2$—CH=CH—Cl
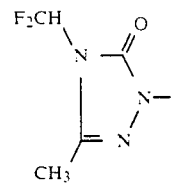 F —O—CH—CH=CH$_2$
                                    |
                                    CH$_3$
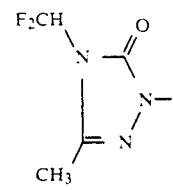 F —O—CH$_2$—C≡CH
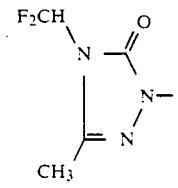 F —O—CH—C≡CH
                                     |
                                     CH$_3$
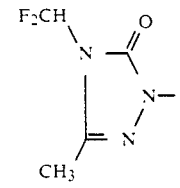 F —O—CH$_2$—C=CH$_2$
                                        |
                                        CH$_3$ -continued
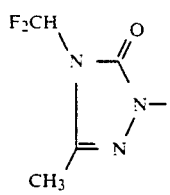 F —O—CH₂—CH₂—OC₂H₅
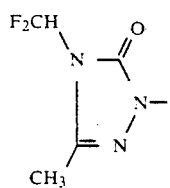 F —O—CH—CH₂—OC₂H₅
             |
             CH₃
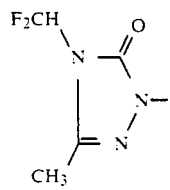 F —O—CH₂—CH—OCH₃
                  |
                  CH₃
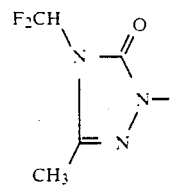 F 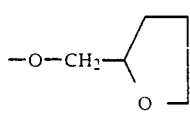
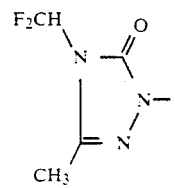 F 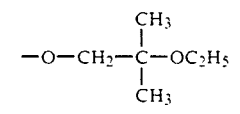
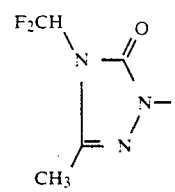 F —O—CH₂—CH₂—O—CH₂—CH₂—OCH₃
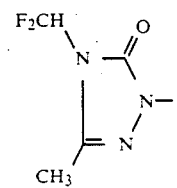 F —O—CH₂—CH₂—O—CH₂—CH₂—OC₂H₅
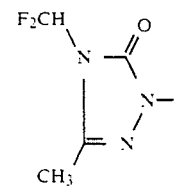 F —O—CH₂—C(=O)—CH₃

-continued
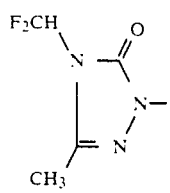 F    −O−CH(CH₃)−C(=O)−CH₃
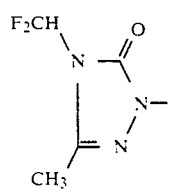 H    −SCH₃
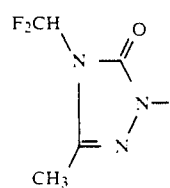 H    −SC₂H₅
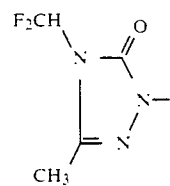 H    −S−CH(CH₃)₂
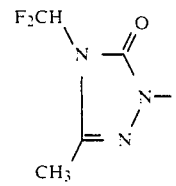 H    −S−CH₂−CH=CH₂
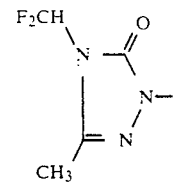 H    −S−CH₂−CH=CH−Cl
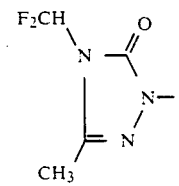 H    −S−CH₂−CH=CH−CH₃
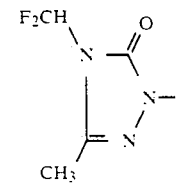 H    −S−CH(CH₃)−CH=CH₂

-continued
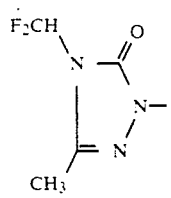 H 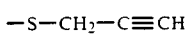
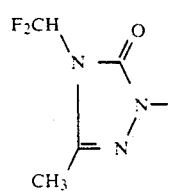 H 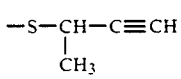
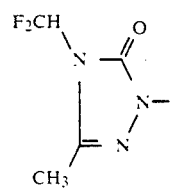 H 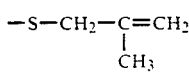
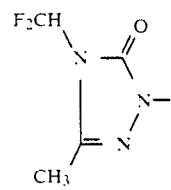 H 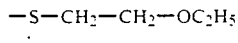
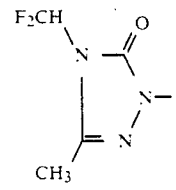 H 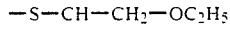
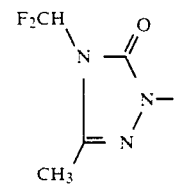 H 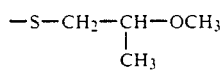
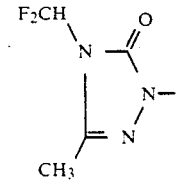 H 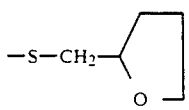
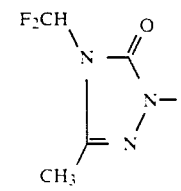 H 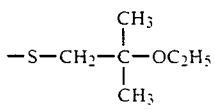

-continued
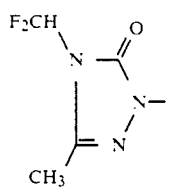 H  —S—CH₂—CH₂—O—CH₂—CH₂—OCH₃
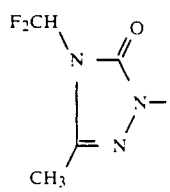 H  —S—CH₂—CH₂—O—CH₂—CH₂—OC₂H₅
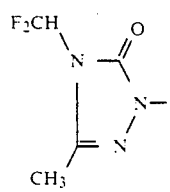 H  
$$-S-CH_2-\overset{\overset{O}{\|}}{C}-CH_3$$
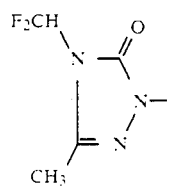 H  
$$-S-\underset{\underset{CH_3}{|}}{CH}-\overset{\overset{O}{\|}}{C}-CH_3$$
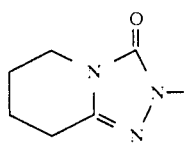 F  
$$-O-CH_2-\underset{\underset{CH_3}{|}}{\overset{\overset{CH_2-OCH_3}{|}}{C}}-CH_2-OCH_3$$
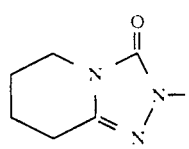 F  —O—⟨cyclohexyl-H⟩
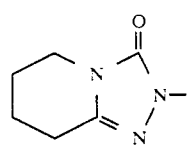 F  —O—⟨cyclopentyl-H⟩
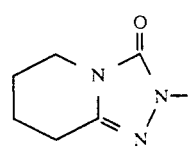 F  —O—CH₂—⟨phenyl⟩
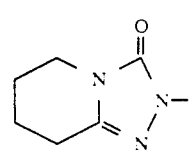 F  —O—CH₂—CN
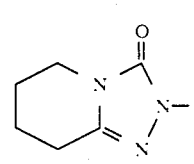 F  —O—CH₂—COOC₂H₅

-continued
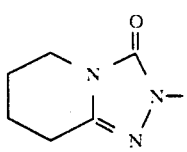 F 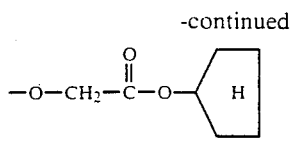
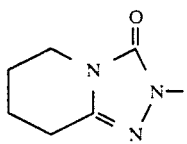 F 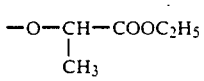
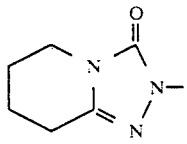 F 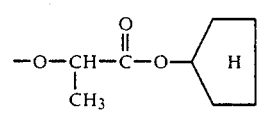
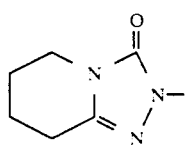 F 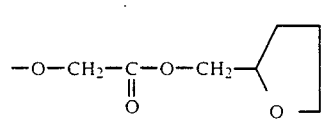
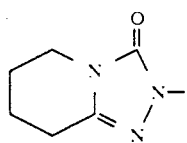 F 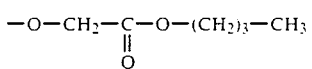
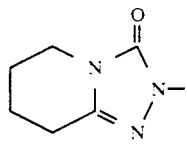 F 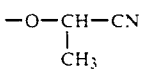
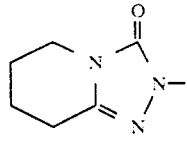 F 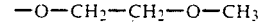
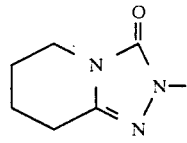 F 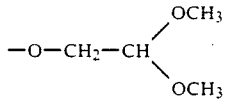
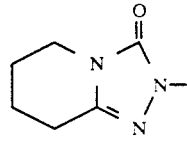 F 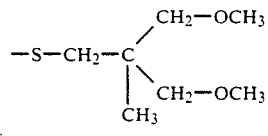
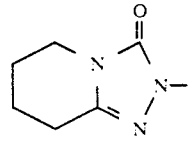 F 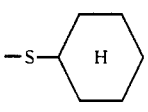
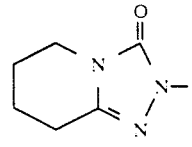 F 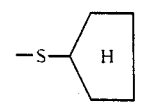

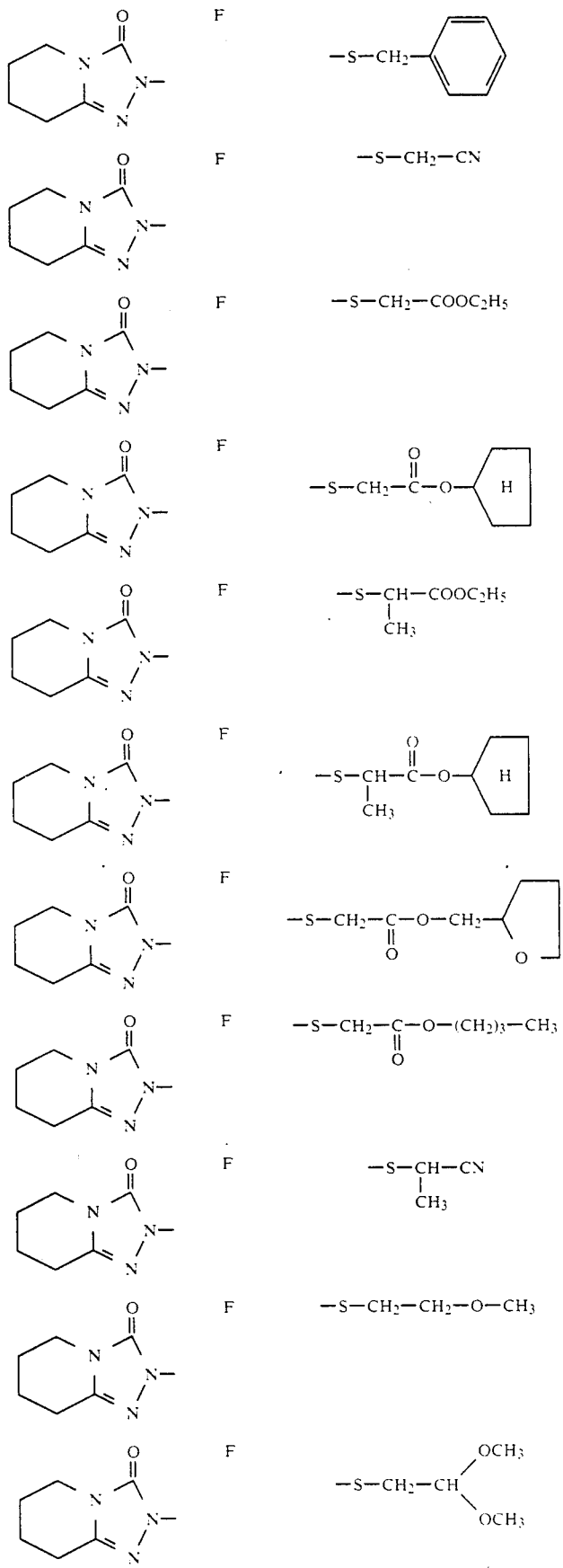

-continued
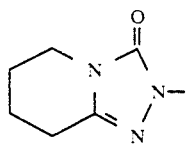 F  —OCH₃
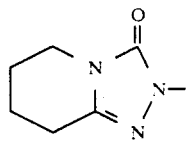 F  —OC₂H₅
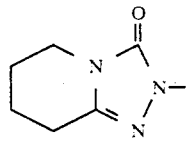 F  —O—CH(CH₃)₂
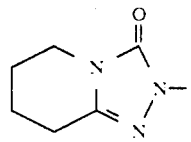 F  —O—CH₂—CH=CH₂
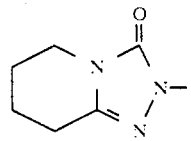 F  —O—CH₂—CH=CH—CH₃
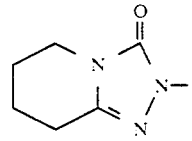 F  —O—CH₂—CH=CH—Cl
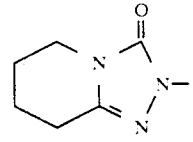 F  —O—CH—CH=CH₂
              |
              CH₃
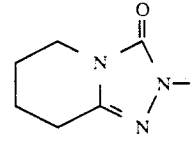 F  —O—CH₂—C≡CH
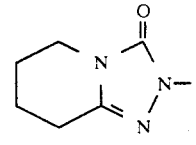 F  —O—CH—C≡CH
              |
              CH₃
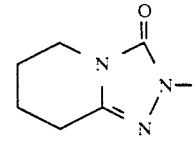 F  —O—CH₂—C=CH₂
               |
               CH₃
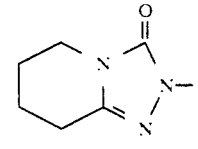 F  —O—CH₂—CH₂—OC₂H₅

-continued
| | | |
|---|---|---|
| 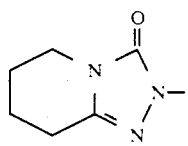 | F | 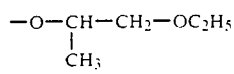 |
| 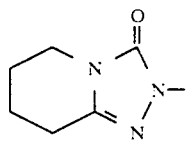 | F | 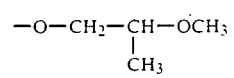 |
| 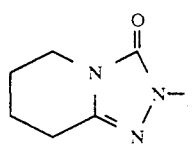 | F | 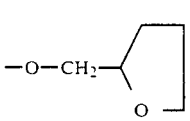 |
| 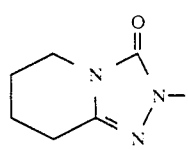 | F | 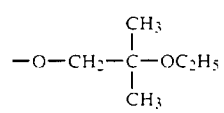 |
| 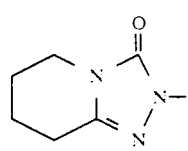 | F | —O—CH₂—CH₂—O—CH₂—CH₂—OCH₃ |
| 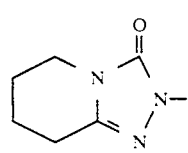 | F | —O—CH₂—CH₂—O—CH₂—CH₂—OC₂H₅ |
| 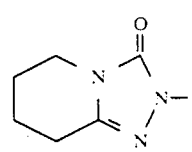 | F | 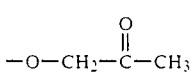 |
| 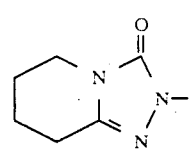 | F | 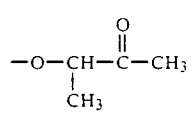 |
| 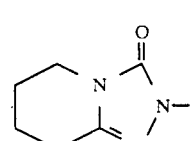 | F | —SCH₃ |
| 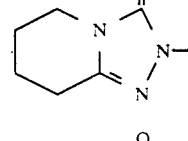 | F | —SC₂H₅ |
| 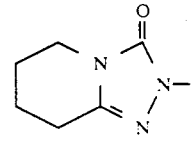 | F | —S—CH(CH₃)₂ |

| | | |
|---|---|---|
| 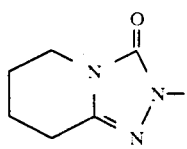 | F | 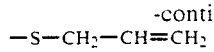 —S—CH₂—CH=CH₂ |
| 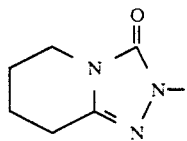 | F | 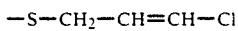 —S—CH₂—CH=CH—Cl |
| 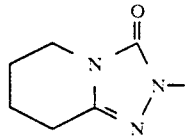 | F |  —S—CH₂—CH=CH—CH₃ |
| 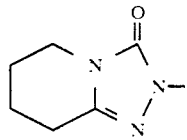 | F | 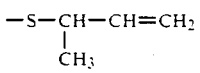 —S—CH—CH=CH₂<br>      \|<br>     CH₃ |
| 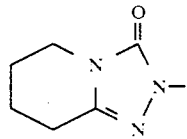 | F | 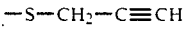 —S—CH₂—C≡CH |
| 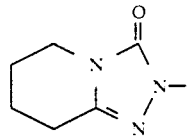 | F | 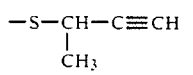 —S—CH—C≡CH<br>     \|<br>    CH₃ |
| 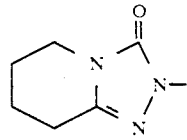 | F | 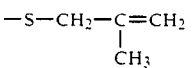 —S—CH₂—C=CH₂<br>         \|<br>        CH₃ |
| 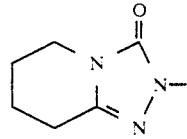 | F | 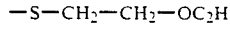 —S—CH₂—CH₂—OC₂H₅ |
| 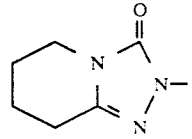 | F | 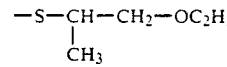 —S—CH—CH₂—OC₂H₅<br>     \|<br>    CH₃ |
| 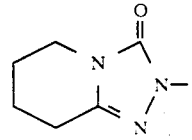 | F | 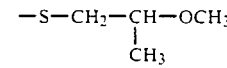 —S—CH₂—CH—OCH₃<br>        \|<br>       CH₃ |
| 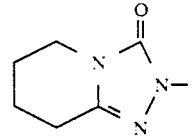 | F |  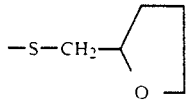 |

-continued
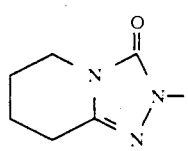 F 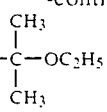
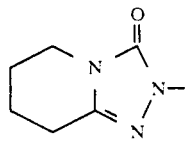 F —S—CH₂—CH₂—O—CH₂—CH₂—OCH₃
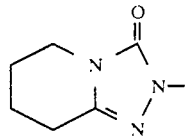 F —S—CH₂—CH₂—O—CH₂—CH₂—OC₂H₅
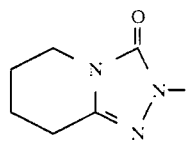 F 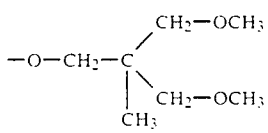
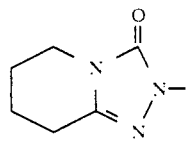 F 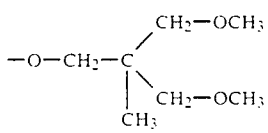
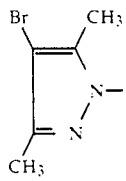 F 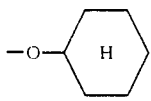
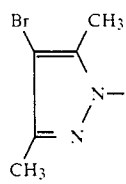 H 
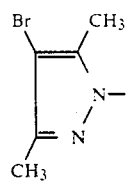 H 
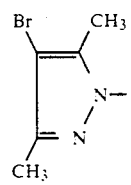 H 
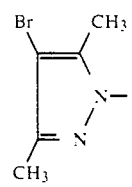 H —O—CH₂—CN -continued
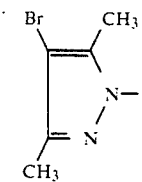 H —O—CH₂—COOC₂H₅
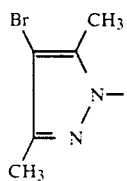 H 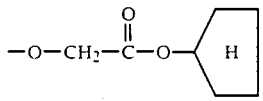
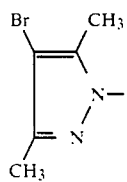 H 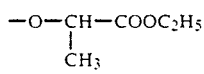
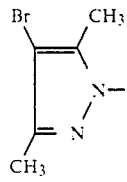 H 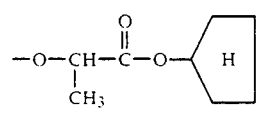
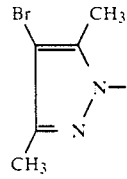 H 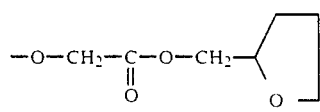
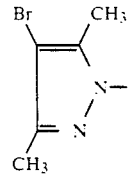 H 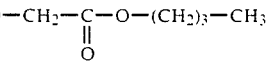
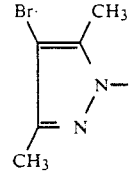 H 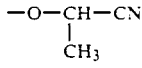
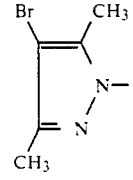 H —CH₂—CH₂—O—CH₃
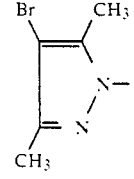 H 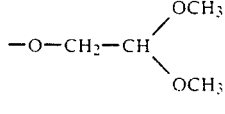

-continued
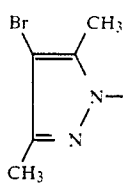 H 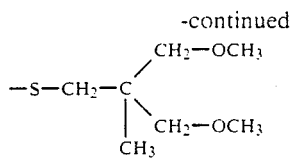
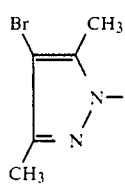 H 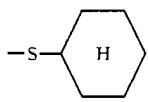
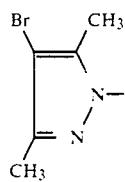 H 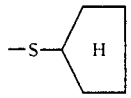
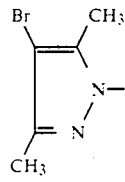 H 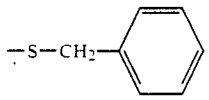
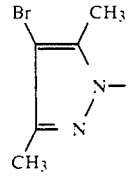 H —S—CH₂—CN
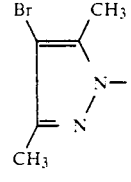 H —S—CH₂—COOC₂H₅
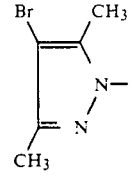 H 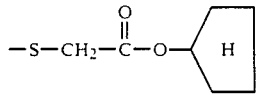
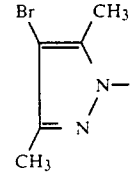 H 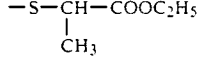
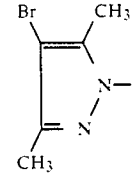 H 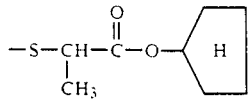

-continued
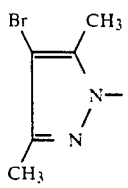 H 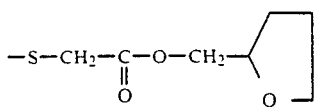
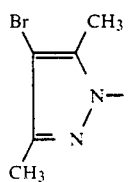 H 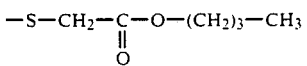
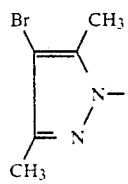 H 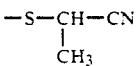
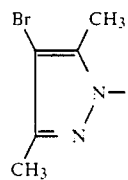 H 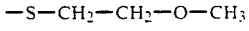
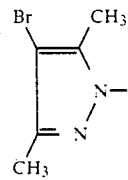 H 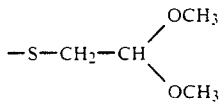
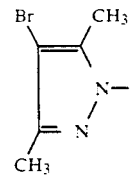 F —OCH₃
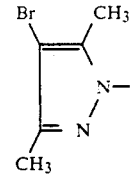 F —OC₂H₅
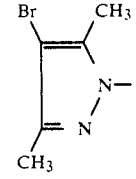 F —O—CH(CH₃)₂
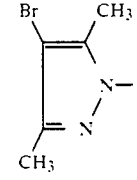 F —O—CH₂—CH=CH₂

-continued
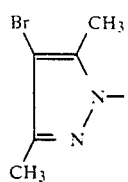 F —O—CH$_2$—CH=CH—CH$_3$
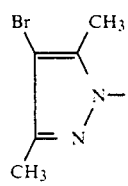 F —O—CH$_2$—CH=CH—Cl
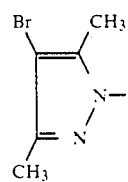 F —O—CH—CH=CH$_2$
                              |
                              CH$_3$
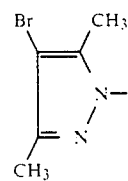 F —O—CH$_2$—C≡CH
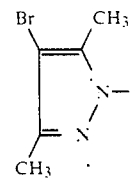 F —O—CH—C≡CH
                              |
                              CH$_3$
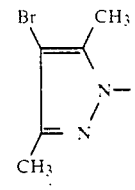 F —O—CH$_2$—C=CH$_2$
                              |
                              CH$_3$
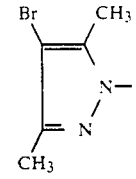 F —O—CH$_2$—CH$_2$—OC$_2$H$_5$
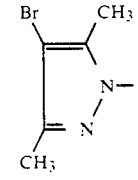 F —O—CH—CH$_2$—OC$_2$H$_5$
                              |
                              CH$_3$
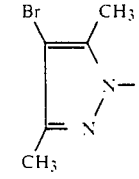 F —O—CH$_2$—CH—OCH$_3$
                              |
                              CH$_3$ -continued
| | | |
|---|---|---|
| 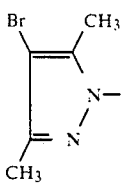 | F | 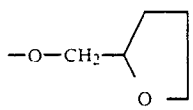 |
| 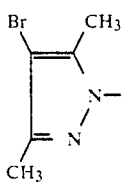 | F | 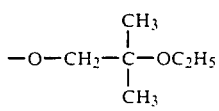 |
| 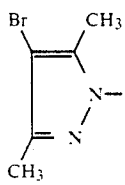 | F | —O—CH₂—CH₂—O—CH₂—CH₂—OCH₃ |
| 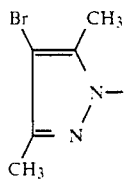 | F | —O—CH₂—CH₂—O—CH₂—CH₂—OC₂H₅ |
| 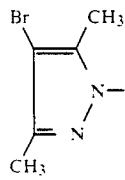 | F | 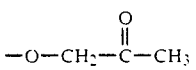 |
| 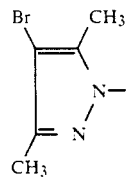 | F | 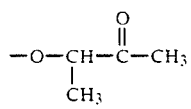 |
| 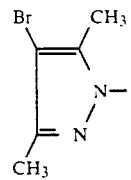 | F | —SCH₃ |
| 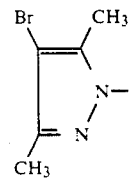 | F | —SC₂H₅ |
| 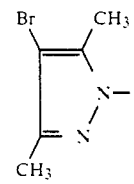 | F | —S—CH(CH₃)₂ |

-continued
| | | |
|---|---|---|
| 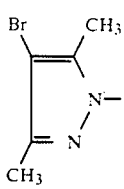 | F | —S—CH$_2$—CH=CH$_2$ |
| 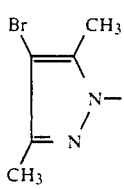 | F | —S—CH$_2$—CH=CH—Cl |
| 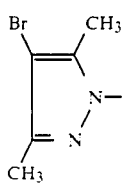 | F | —S—CH$_2$—CH=CH—CH$_3$ |
| 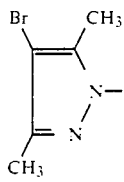 | F | —S—CH—CH=CH$_2$<br>      \|<br>     CH$_3$ |
| 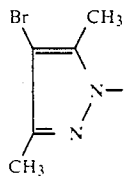 | F | —S—CH$_2$—C≡CH |
| 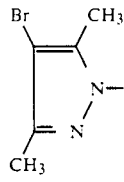 | F | —S—CH—C≡CH<br>     \|<br>    CH$_3$ |
| 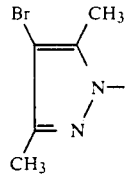 | F | —S—CH$_2$—C=CH$_2$<br>        \|<br>       CH$_3$ |
| 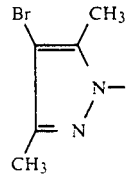 | F | —S—CH$_2$—CH$_2$—OC$_2$H$_5$ |
| 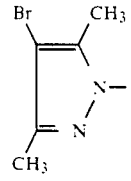 | F | —S—CH—CH$_2$—OC$_2$H$_5$ |

-continued
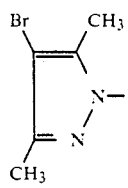 F 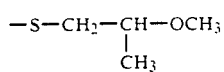
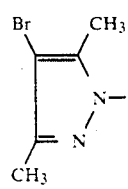 F 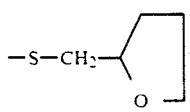
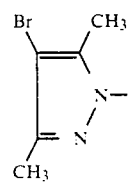 F 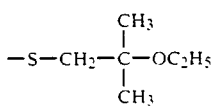
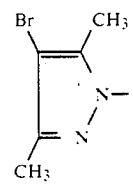 F —S—CH₂—CH₂—O—CH₂—CH₂—OCH₃
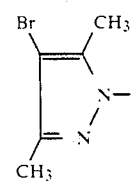 F —S—CH₂—CH₂—O—CH₂—CH₂—OC₂H₅
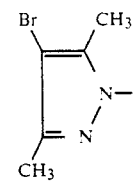 F 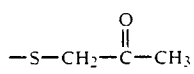
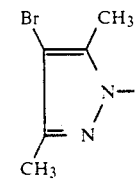 F 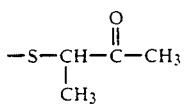
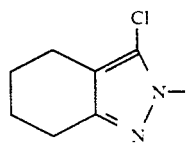 H 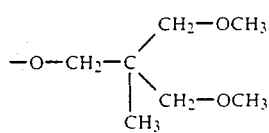
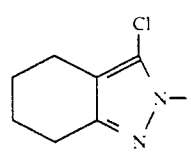 H 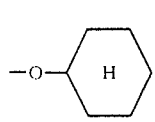

-continued
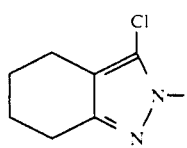 H 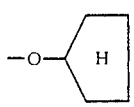
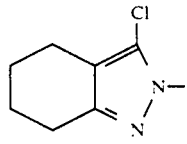 H 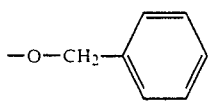
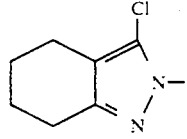 H —O—CH$_2$—CN
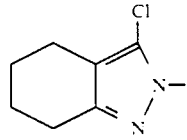 H —O—CH$_2$—COOC$_2$H$_5$
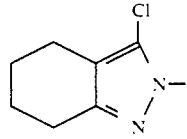 H 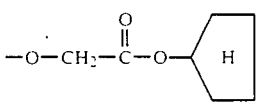
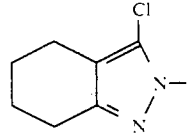 H —O—CH—COOC$_2$H$_5$
　　　　　　　　|
　　　　　　　CH$_3$
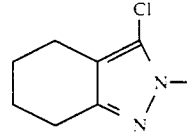 H 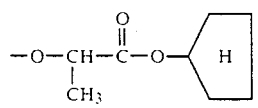
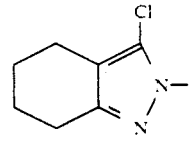 H 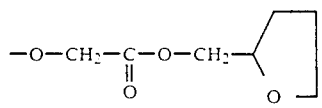
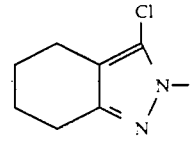 H —O—CH$_2$—C—O—(CH$_2$)$_3$—CH$_3$
　　　　　　　　　‖
　　　　　　　　　O
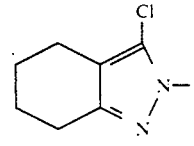 H —O—CH—CN
　　　　　　|
　　　　　CH$_3$
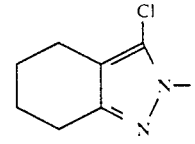 H —O—CH$_2$—CH$_2$—O—CH$_3$ -continued
| | | |
|---|---|---|
| 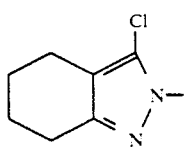 | H | 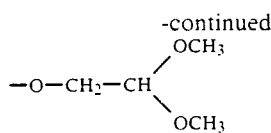 |
| 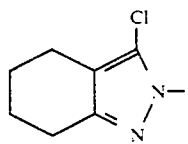 | H | 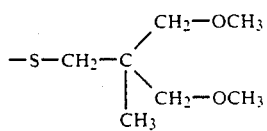 |
| 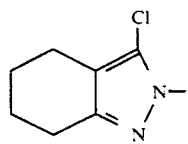 | H | 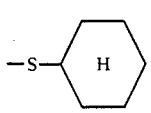 |
| 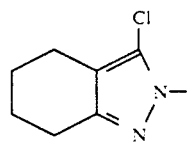 | H | 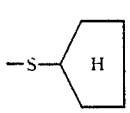 |
| 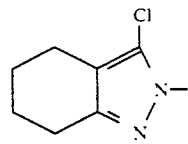 | H | 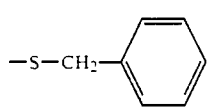 |
| 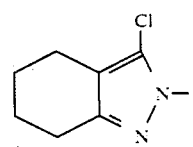 | H | —S—CH$_2$—CN |
| 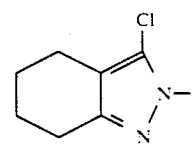 | H | —S—CH$_2$—COOC$_2$H$_5$ |
| 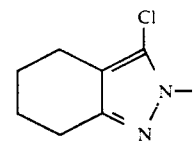 | H | 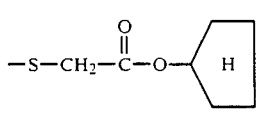 |
| 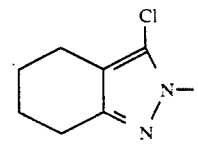 | H | 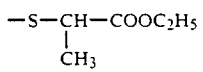 |
| 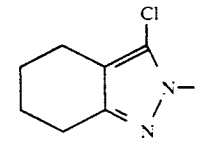 | H | 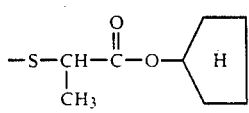 |
| 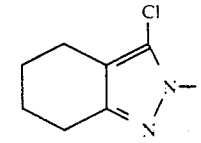 | H | 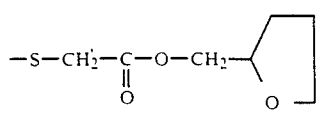 |

-continued
| | | |
|---|---|---|
| 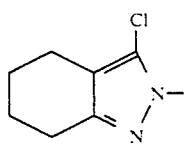 | H | —S—CH₂—C(=O)—O—(CH₂)₃—CH₃ |
| 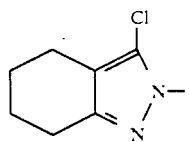 | H | —S—CH(CH₃)—CN |
| 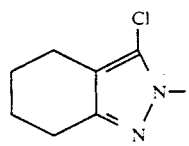 | H | —S—CH₂—CH₂—O—CH₃ |
| 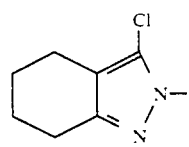 | H | —S—CH₂—CH(OCH₃)₂ |
| 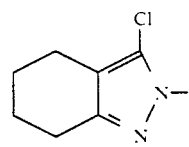 | H | —OCH₃ |
| 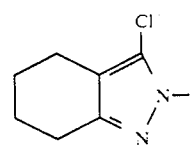 | H | —OC₂H₅ |
| 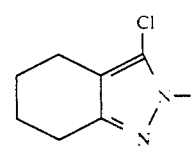 | H | —O—CH(CH₃)₂ |
| 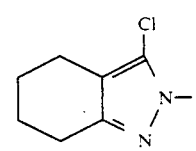 | H | —O—CH₂—CH=CH₂ |
| 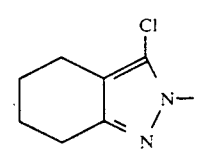 | H | —O—CH₂—CH=CH—CH₃ |
| 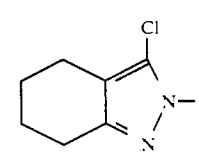 | H | —O—CH₂—CH=CH—Cl |
| 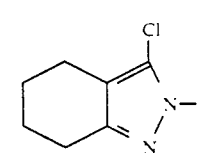 | H | —O—CH(CH₃)—CH=CH₂ |

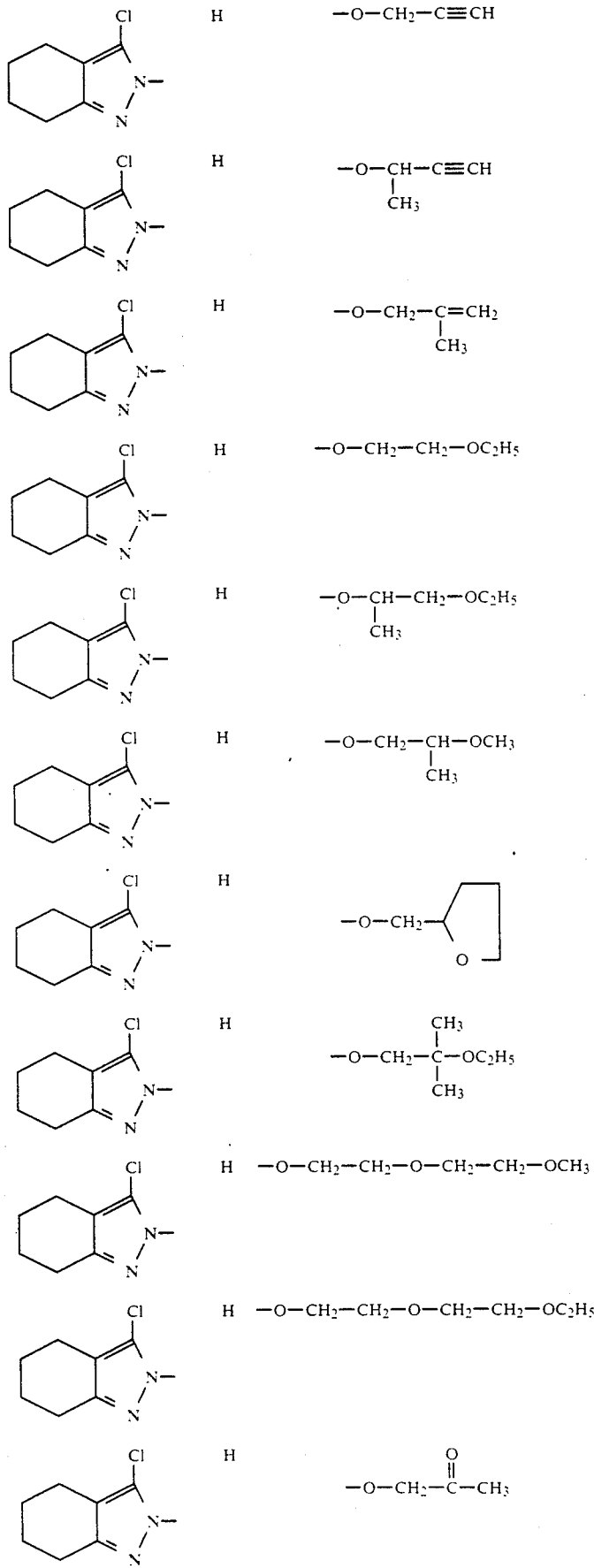

-continued
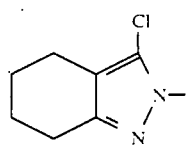 H  $-O-\underset{\underset{CH_3}{|}}{CH}-\overset{\overset{O}{\|}}{C}-CH_3$
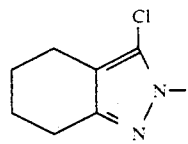 H  $-SCH_3$
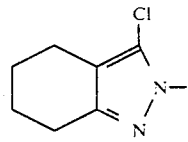 H  $-SC_2H_5$
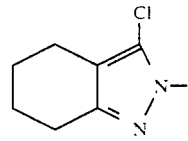 H  $-S-CH(CH_3)_2$
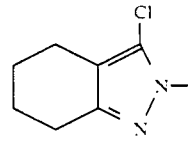 H  $-S-CH_2-CH=CH_2$
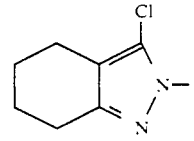 H  $-S-CH_2-CH=CH-Cl$
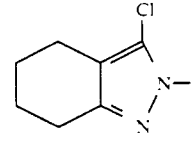 H  $-S-CH_2-CH=CH-CH_3$
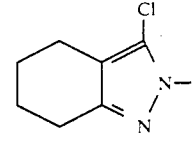 H  $-S-\underset{\underset{CH_3}{|}}{CH}-CH=CH_2$
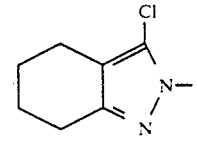 H  $-S-CH_2-C{\equiv}CH$
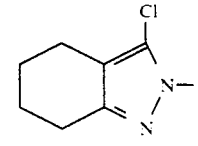 H  $-S-\underset{\underset{CH_3}{|}}{CH}-C{\equiv}CH$
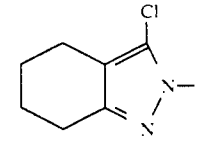 H  $-S-CH_2-\underset{\underset{CH_3}{|}}{C}=CH_2$ -continued
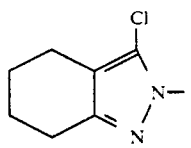 H —S—CH₂—CH₂—OC₂H₅
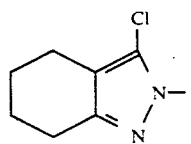 H 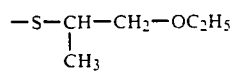
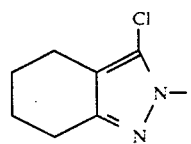 H 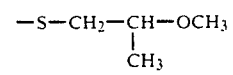
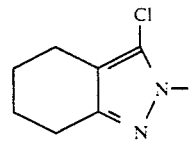 H 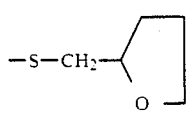
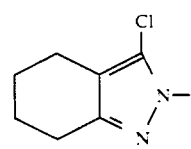 H 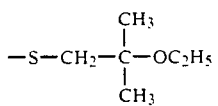
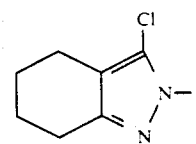 H —S—CH₂—CH₂—O—CH₂—CH₂—OCH₃
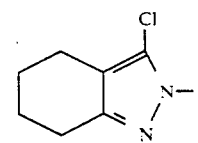 H —S—CH₂—CH₂—O—CH₂—CH₂—OC₂H₅
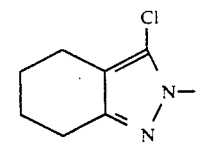 H 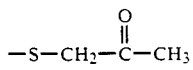
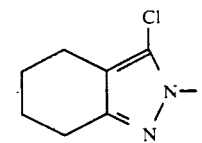 H 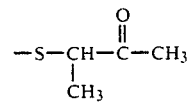
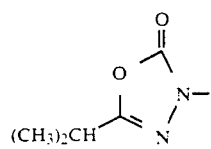 F 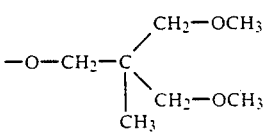
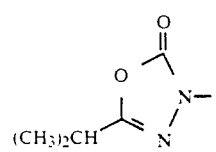 F 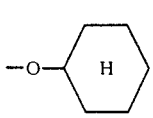

-continued
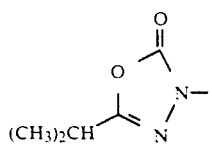 F 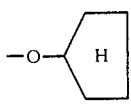
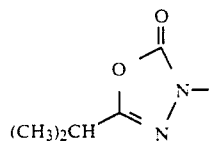 F 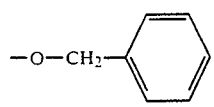
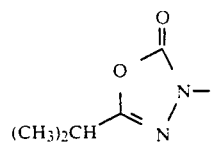 F 
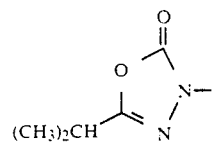 F —O—CH₂—COOC₂H₅
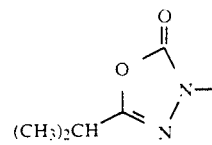 F 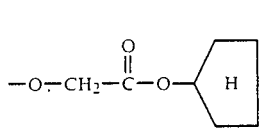
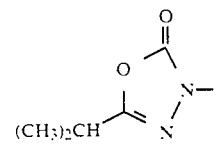 F —O—CH—COOC₂H₅
                          |
                          CH₃
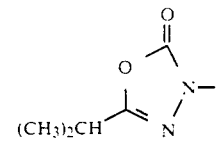 F 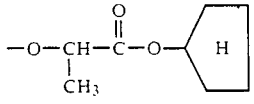
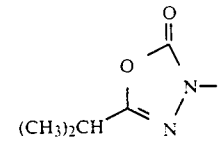 F 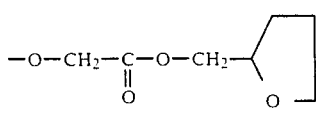
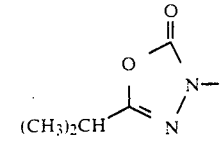 F 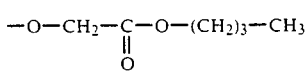
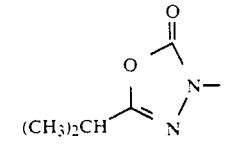 F —O—CH—CN
                          |
                          CH₃
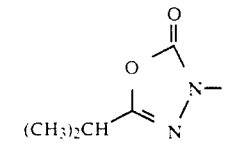 F —O—CH₂—CH₂—O—CH₃

-continued
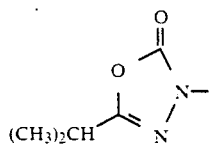 F 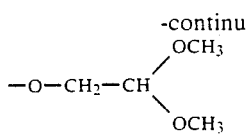
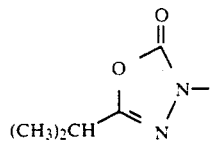 F 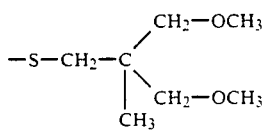
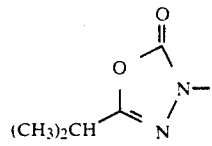 F 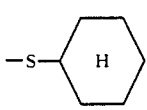
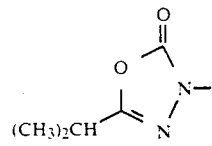 F 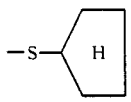
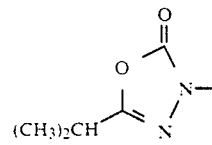 F 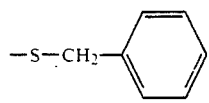
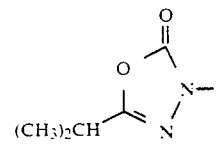 F 
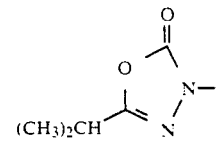 F 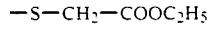
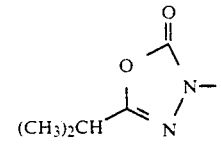 F 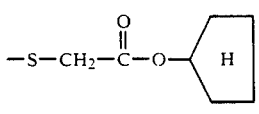
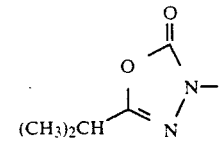 F 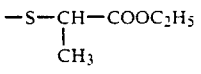
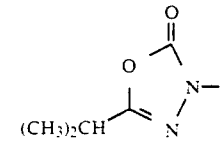 F 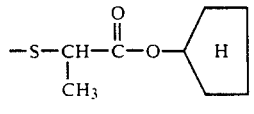
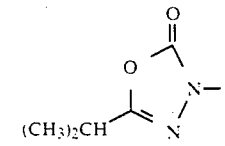 F 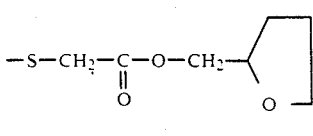

| Structure | R | R' |
|---|---|---|
| (CH₃)₂CH–C(=N–N(–)–C(=O)–O–) [1,3,4-oxadiazol-2(3H)-one, 5-isopropyl, N-substituted] | F | –S–CH₂–C(=O)–O–(CH₂)₃–CH₃ |
| same | F | –S–CH(CH₃)–CN |
| same | F | –S–CH₂–CH₂–O–CH₃ |
| same | F | –S–CH₂–CH(OCH₃)₂ |
| same | F | –OCH₃ |
| same | F | –OC₂H₅ |
| same | F | –O–CH(CH₃)₂ |
| same | F | –O–CH₂–CH=CH₂ |
| same | F | –O–CH₂–CH=CH–CH₃ |
| same | F | –O–CH₂–CH=CH–Cl |
| same | F | –O–CH(CH₃)–CH=CH₂ |

-continued
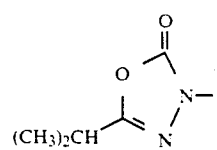 F    —O—CH₂—C≡CH
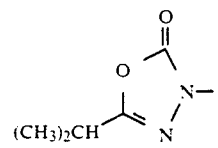 F    —O—CH—C≡CH
              |
              CH₃
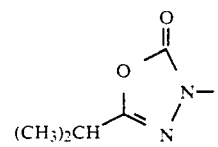 F    —O—CH₂—C=CH₂
              |
              CH₃
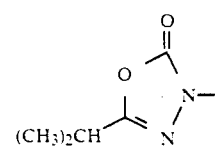 F    —O—CH₂—CH₂—OC₂H₅
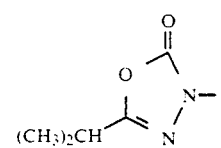 F    —O—CH—CH₂—OC₂H₅
              |
              CH₃
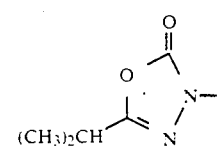 F    —O—CH₂—CH—OCH₃
              |
              CH₃
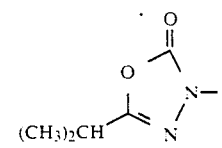 F    —O—CH₂—⟨tetrahydrofuran-2-yl⟩
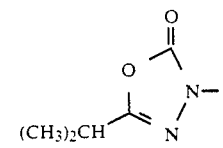 F       CH₃
              |
          —O—CH₂—C—OC₂H₅
              |
              CH₃
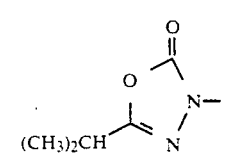 F  —O—CH₂—CH₂—O—CH₂—CH₂—OCH₃
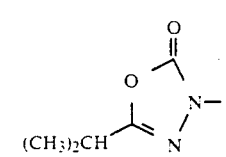 F  —O—CH₂—CH₂—O—CH₂—CH₂—OC₂H₅
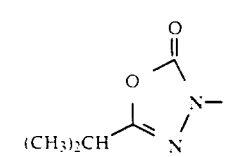 F        O
                     ‖
          —O—CH₂—C—CH₃

-continued
| | | |
|---|---|---|
| 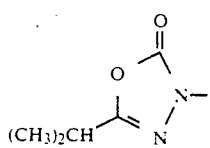 | F | —O—CH—C—CH₃ (with O= on C, CH₃ below CH) |
| 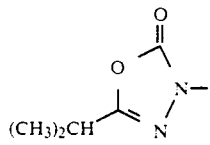 | H | —SCH₃ |
| 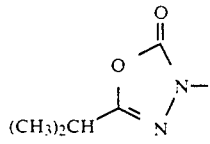 | H | —SC₂H₅ |
| 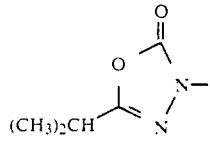 | H | —S—CH(CH₃)₂ |
| 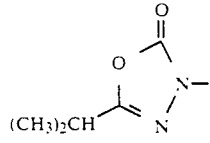 | H | —S—CH₂—CH=CH₂ |
| 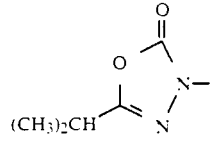 | H | —S—CH₂—CH=CH—Cl |
| 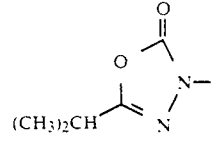 | H | —S—CH₂—CH=CH—CH₃ |
| 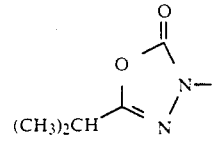 | H | —S—CH—CH=CH₂ (CH₃ below CH) |
| 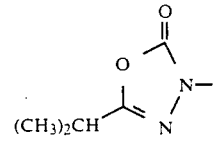 | H | —S—CH₂—C≡CH |
| 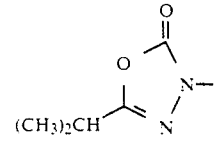 | H | —S—CH—C≡CH (CH₃ below CH) |
| 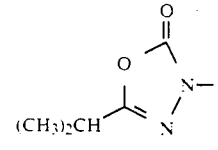 | H | —S—CH₂—C=CH₂ (CH₃ below C) |

-continued
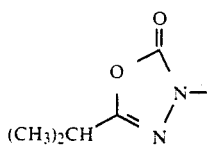 H —S—CH₂—CH₂—OC₂H₅
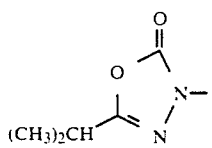 H —S—CH—CH₂—OC₂H₅
                         |
                         CH₃
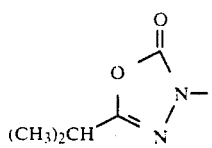 H —S—CH₂—CH—OCH₃
                              |
                              CH₃
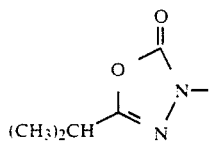 H —S—CH₂—⟨tetrahydrofuran-2-yl⟩
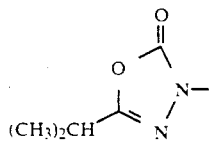 H  —S—CH₂—C(CH₃)₂—OC₂H₅
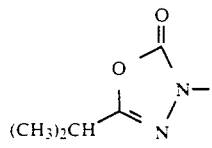 H —S—CH₂—CH₂—O—CH₂—CH₂—OCH₃
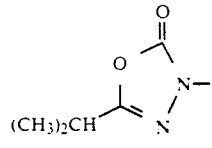 H —S—CH₂—CH₂—O—CH₂—CH₂—OC₂H₅
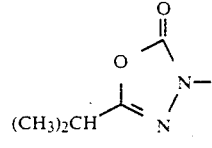 H —S—CH₂—C(=O)—CH₃
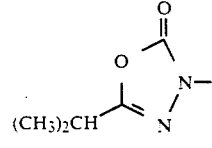 H —S—CH(CH₃)—C(=O)—CH₃
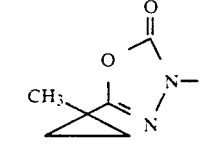 F —O—CH₂—C(CH₃)(CH₂OCH₃)(CH₂OCH₃)
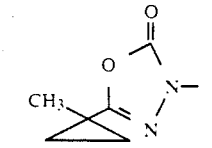 F —O—⟨cyclohexyl⟩ H -continued
| | | |
|---|---|---|
| 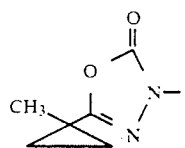 | F | 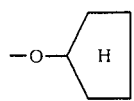 |
| 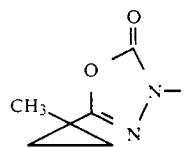 | F | 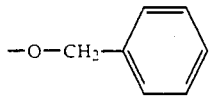 |
| 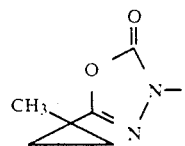 | F | 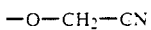 |
| 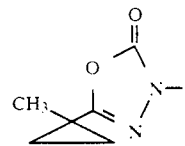 | F | 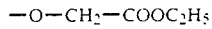 |
| 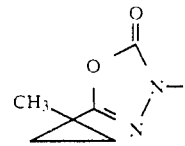 | F | 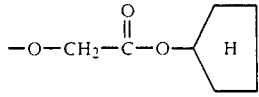 |
| 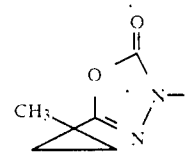 | F | 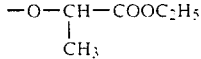 |
| 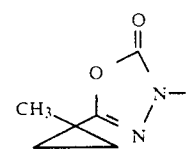 | F | 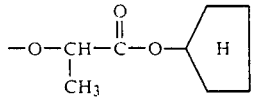 |
| 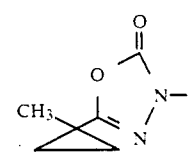 | F | 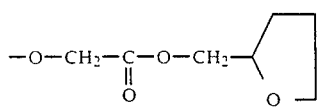 |
| 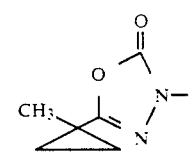 | F | 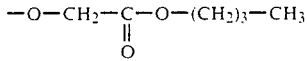 |
| 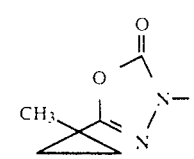 | F | 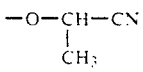 |

-continued
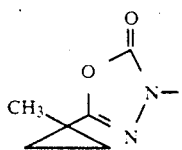 F —O—CH₂—CH₂—O—CH₃
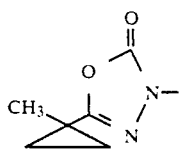 F 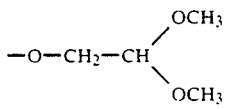
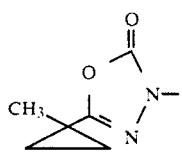 H 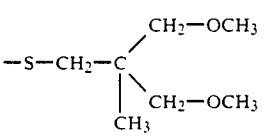
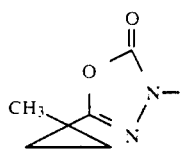 H 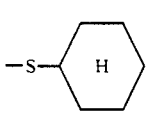
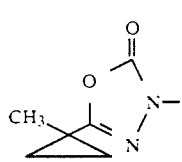 H 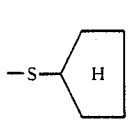
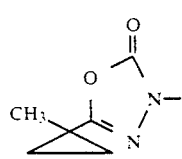 H 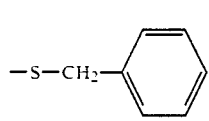
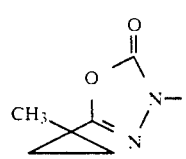 H —S—CH₂—CN
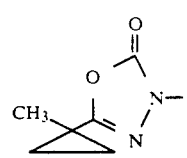 H —S—CH₂—COOC₂H₅
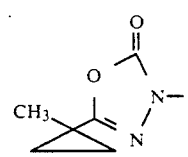 H 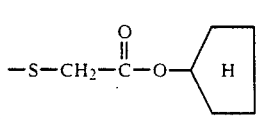
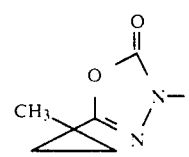 H —S—CH—COOC₂H₅
　　　　　　　　　　|
　　　　　　　　　　CH₃

-continued
| | | |
|---|---|---|
| 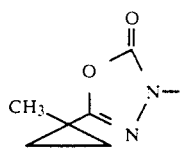 | H | 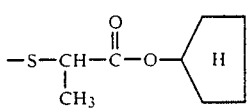 |
| 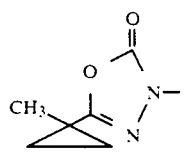 | H | 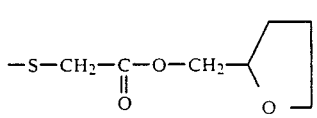 |
| 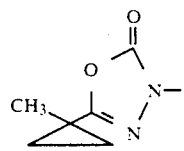 | H | 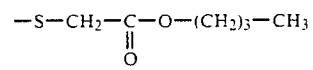 |
| 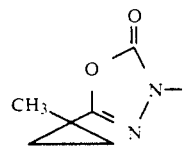 | H | 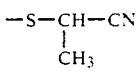 |
| 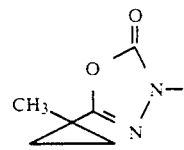 | H | 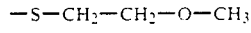 |
| 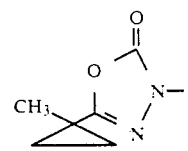 | H | 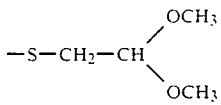 |
| 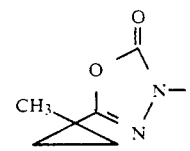 | F | —OCH$_3$ |
| 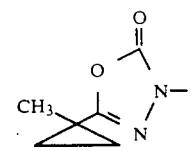 | F | —OC$_2$H$_5$ |
| 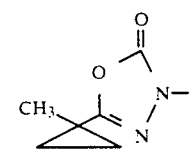 | F | —O—CH(CH$_3$)$_2$ |
| 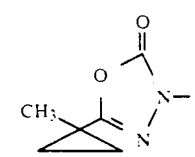 | F | —O—CH$_2$—CH=CH$_2$ |

-continued
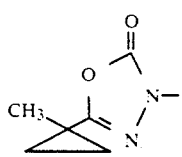 F  —O—CH$_2$—CH=CH—CH$_3$
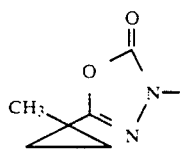 F  —O—CH$_2$—CH=CH—Cl
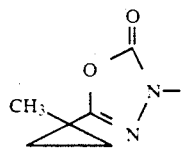 F  —O—CH—CH=CH$_2$
　　　　　|
　　　　　CH$_3$
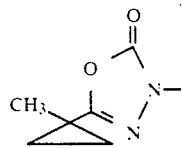 F  —O—CH$_2$—C≡CH
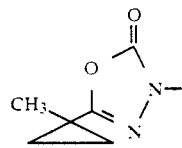 F  —O—CH—C≡CH
　　　　　|
　　　　　CH$_3$
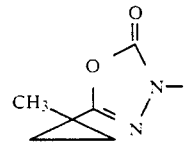 F  —O—CH$_2$—C=CH$_2$
　　　　　　　　|
　　　　　　　　CH$_3$
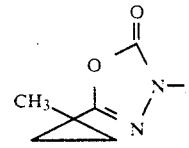 F  —O—CH$_2$—CH$_2$—OC$_2$H$_5$
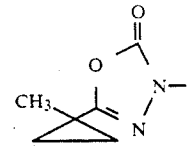 F  —O—CH—CH$_2$—OC$_2$H$_5$
　　　　　|
　　　　　CH$_3$
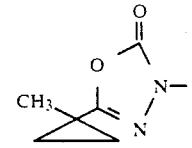 F  —O—CH$_2$—CH—OCH$_3$
　　　　　　　　|
　　　　　　　　CH$_3$
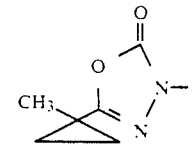 F  —O—CH$_2$—⟨tetrahydrofuran⟩

-continued
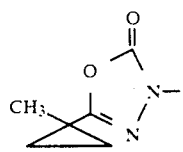 F 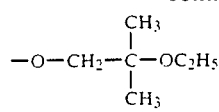
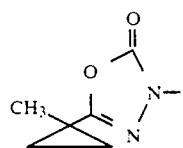 F —O—CH₂—CH₂—O—CH₂—CH₂—OCH₃
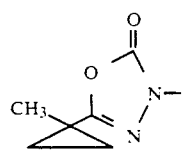 F —O—CH₂—CH₂—O—CH₂—CH₂—OC₂H₅
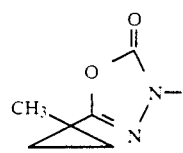 F $-O-CH_2-\overset{O}{\overset{\|}{C}}-CH_3$
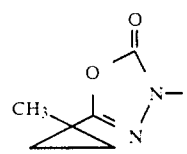 F $-O-\underset{\underset{CH_3}{|}}{CH}-\overset{O}{\overset{\|}{C}}-CH_3$
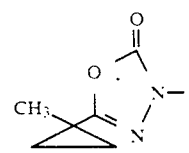 F —SCH₃
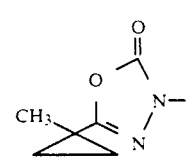 F —SC₂H₅
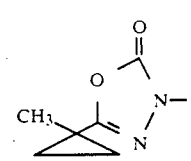 F —S—CH(CH₃)₂
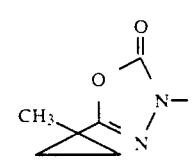 F —S—CH₂—CH=CH₂
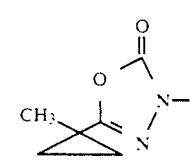 F —S—CH₂—CH=CH—Cl -continued
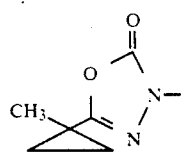 F  —S—CH₂—CH=CH—CH₃
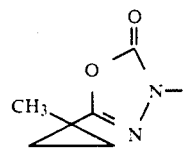 F  —S—CH—CH=CH₂
             |
             CH₃
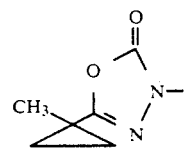 F  —S—CH₂—C≡CH
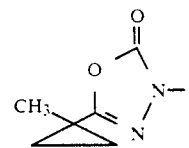 F  —S—CH—C≡CH
             |
             CH₃
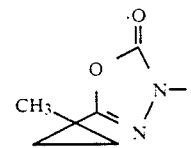 F  —S—CH₂—C=CH₂
             |
             CH₃
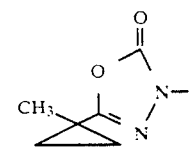 F  —S—CH₂—CH₂—OC₂H₅
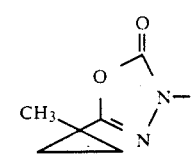 F  —S—CH—CH₂—OC₂H₅
             |
             CH₃
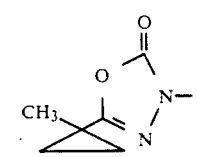 F  —S—CH₂—CH—OCH₃
             |
             CH₃
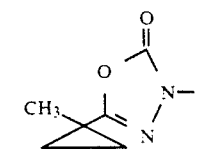 F  —S—CH₂—[tetrahydrofuran-2-yl]
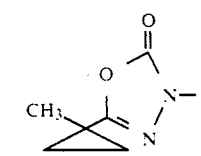 F     CH₃
              |
     —S—CH₂—C—OC₂H₅
              |
              CH₃

-continued
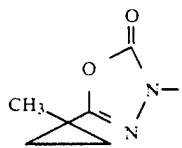 F 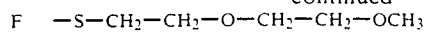 —S—CH$_2$—CH$_2$—O—CH$_2$—CH$_2$—OCH$_3$
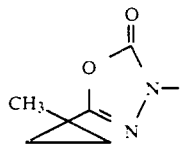 F 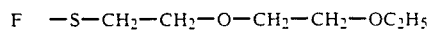 —S—CH$_2$—CH$_2$—O—CH$_2$—CH$_2$—OC$_2$H$_5$
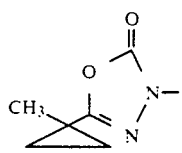 F 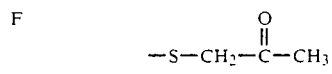
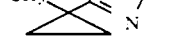 F 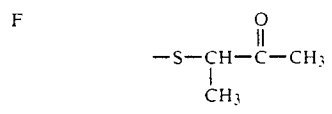
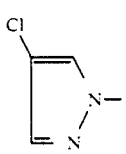 F 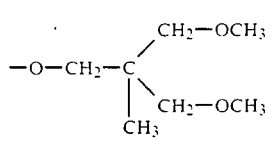
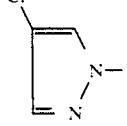 F 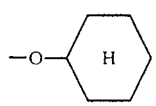
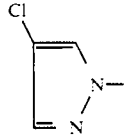 F 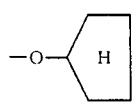
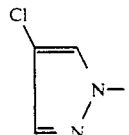 F 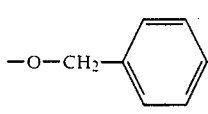
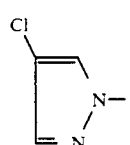 F  —O—CH$_2$—CN
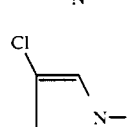 F  —O—CH$_2$—COOC$_2$H$_5$
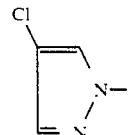 F 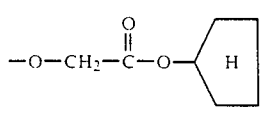

-continued
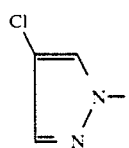 F 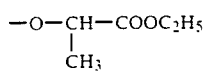
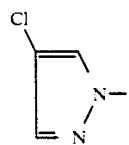 F 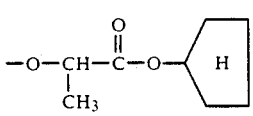
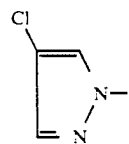 F 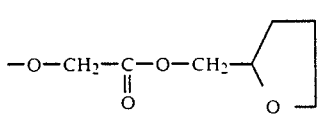
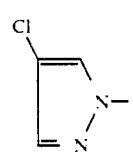 F 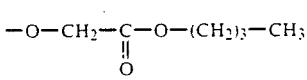
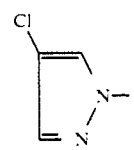 F 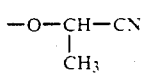
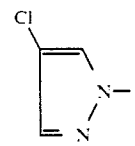 F 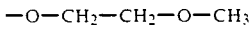
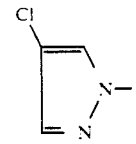 F 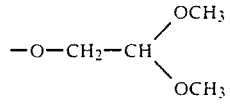
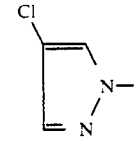 F 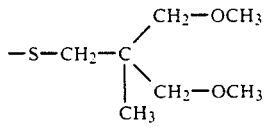
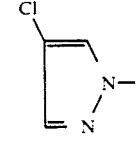 F 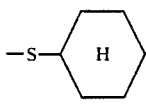
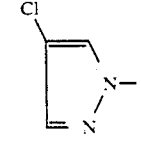 F 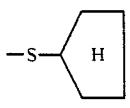
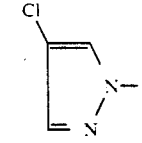 F 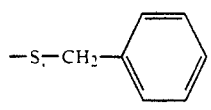

-continued
| | | |
|---|---|---|
| 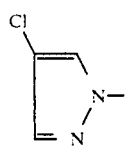 | F | —S—CH$_2$—CN |
| 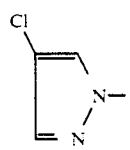 | F | —S—CH$_2$—COOC$_2$H$_5$ |
| 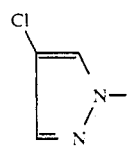 | F | 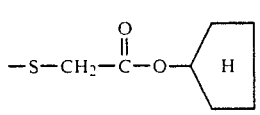 |
| 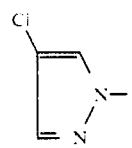 | F | 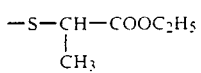 |
| 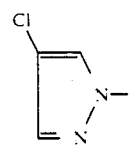 | F | 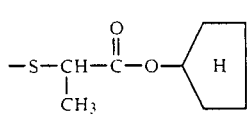 |
| 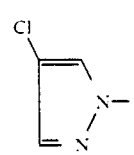 | F | 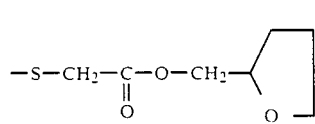 |
| 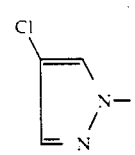 | F | 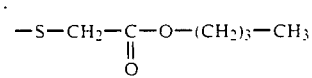 |
| 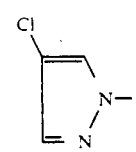 | F | 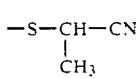 |
| 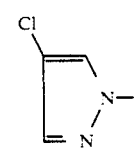 | F | —S—CH$_2$—CH$_2$—O—CH$_3$ |
| 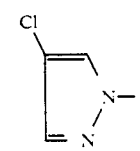 | F | 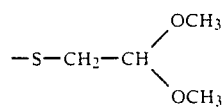 |
| 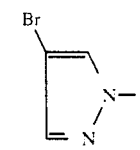 | F | —OCH$_3$ |

-continued
| | | |
|---|---|---|
| 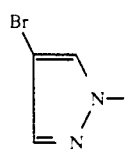 | F | —OC$_2$H$_5$ |
| 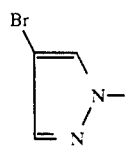 | F | —O—CH(CH$_3$)$_2$ |
| 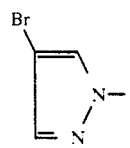 | F | —O—CH$_2$—CH=CH$_2$ |
| 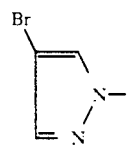 | F | —O—CH$_2$—CH=CH—CH$_3$ |
| 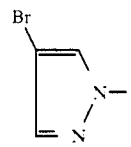 | F | —O—CH$_2$—CH=CH—Cl |
| 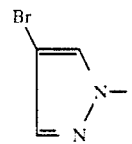 | F | —O—CH—CH=CH$_2$<br>       \|<br>      CH$_3$ |
| 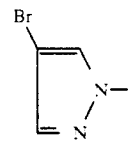 | F | —O—CH$_2$—C≡CH |
| 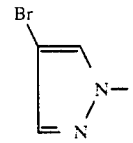 | F | —O—CH—C≡CH<br>       \|<br>      CH$_3$ |
| 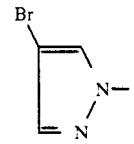 | F | —O—CH$_2$—C=CH$_2$<br>         \|<br>       CH$_3$ |
| 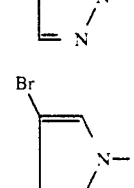 | F | —O—CH$_2$—CH$_2$—OC$_2$H$_5$ |
| 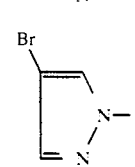 | F | —O—CH—CH$_2$—OC$_2$H$_5$<br>       \|<br>      CH$_3$ |

-continued
| | | |
|---|---|---|
| 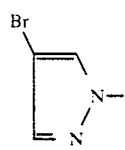 | F | 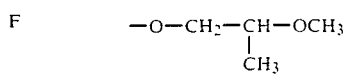 |
| 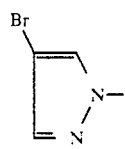 | F | 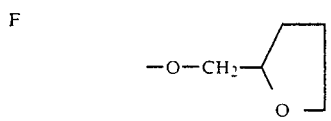 |
| 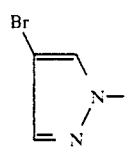 | F | 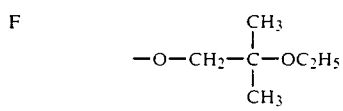 |
| 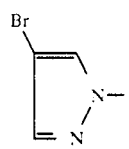 | F | 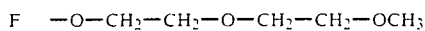 |
| 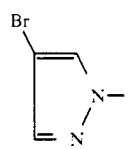 | F | 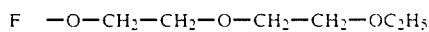 |
| 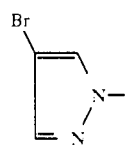 | F | 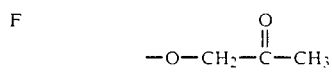 |
| 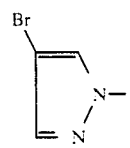 | F | 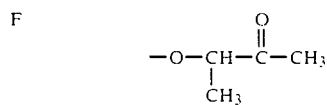 |
| 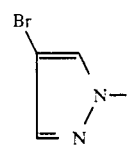 | F | —SCH$_3$ |
| 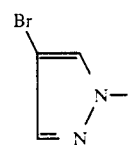 | F | —SC$_2$H$_5$ |
| 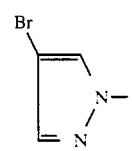 | F | —S—CH(CH$_3$)$_2$ |
| 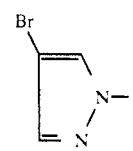 | F | —S—CH$_2$—CH=CH$_2$ |

-continued
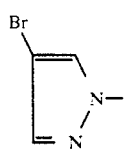   F   —S—CH$_2$—CH=CH—Cl
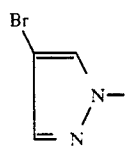   F   —S—CH$_2$—CH=CH—CH$_3$
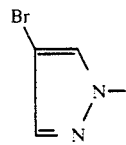   F   —S—CH—CH=CH$_2$
                          |
                          CH$_3$
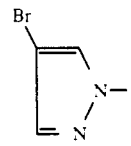   F   —S—CH$_2$—C≡CH
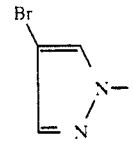   F   —S—CH—C≡CH
                          |
                          CH$_3$
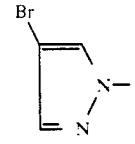   F   —S—CH$_2$—C≡CH$_2$
                          |
                          CH$_3$
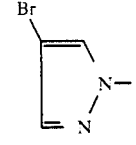   F   —S—CH$_2$—CH$_2$—OC$_2$H$_5$
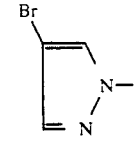   F   —S—CH—CH$_2$—OC$_2$H$_5$
                          |
                          CH$_3$
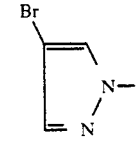   F   —S—CH$_2$—CH—OCH$_3$
                                     |
                                     CH$_3$
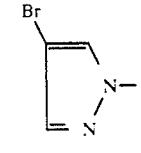  F   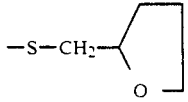
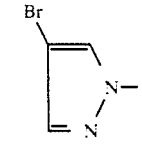  F   —S—CH$_2$—C(CH$_3$)$_2$—OC$_2$H$_5$

| | | |
|---|---|---|
| 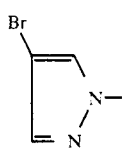 | F | 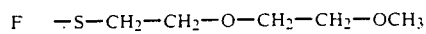 —S—CH₂—CH₂—O—CH₂—CH₂—OCH₃ |
| 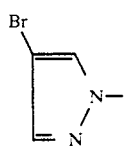 | F | 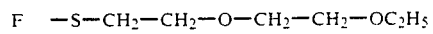 —S—CH₂—CH₂—O—CH₂—CH₂—OC₂H₅ |
| 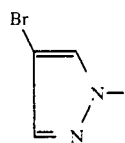 | F | 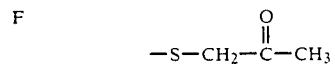 |
| 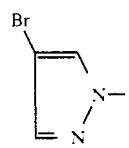 | F | 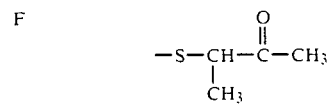 |
| 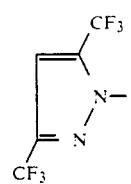 | F | 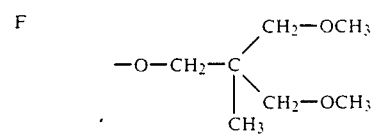 |
| 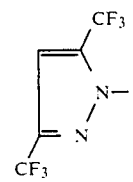 | F | 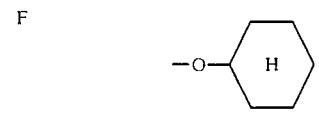 |
| 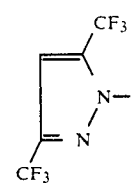 | F | 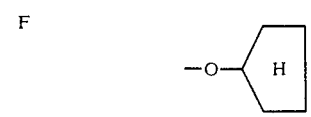 |
| 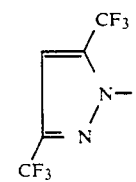 | F | 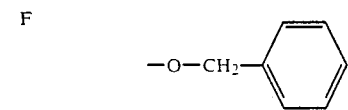 |
| 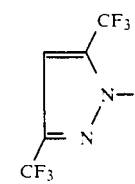 | F |  —O—CH₂—CN |

-continued
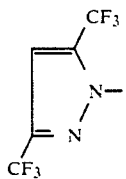 F —O—CH₂—COOC₂H₅
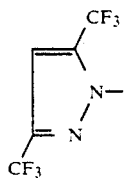 F 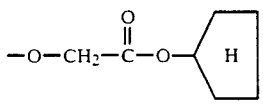
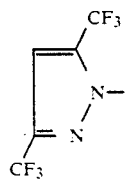 F —O—CH—COOC₂H₅
                  |
                  CH₃
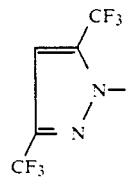 F 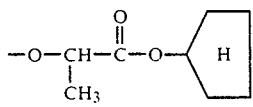
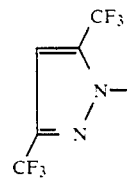 F 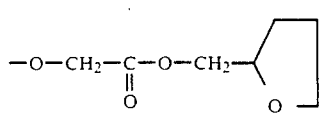
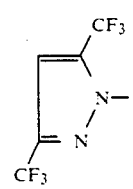 F —O—CH₂—C(=O)—O—(CH₂)₃—CH₃
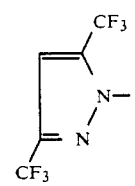 F —O—CH—CN
              |
              CH₃
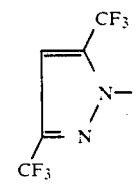 F —O—CH₂—CH₂—O—CH₃
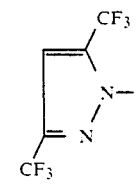 F 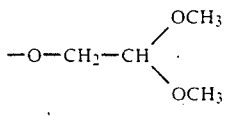

-continued
| | | |
|---|---|---|
| 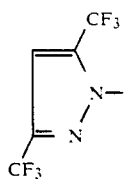 | F | 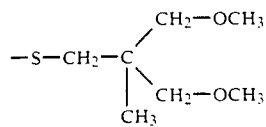 |
| 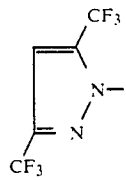 | F | 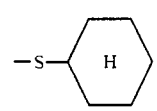 |
| 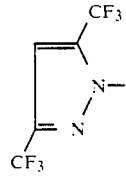 | F | 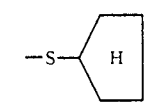 |
| 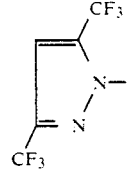 | F | —S—CH$_2$—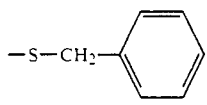 |
| 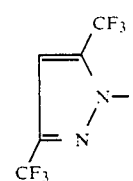 | F | —S—CH$_2$—CN |
| 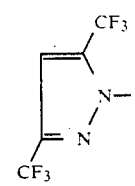 | F | —S—CH$_2$—COOC$_2$H$_5$ |
| 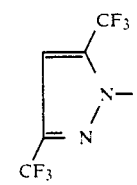 | F | 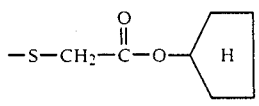 |
| 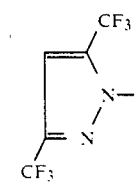 | F | 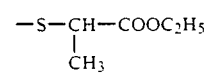 |
| 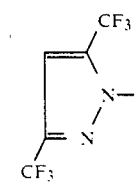 | F | 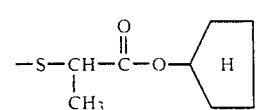 |

-continued

| Pyrazole (3,5-bis-CF₃) | X | R |
|---|---|---|
| 3,5-bis(CF₃)pyrazol-1-yl | F | $-S-CH_2-\underset{\underset{O}{\parallel}}{C}-O-CH_2-\text{(tetrahydrofuran-2-yl)}$ |
| 3,5-bis(CF₃)pyrazol-1-yl | F | $-S-CH_2-\underset{\underset{O}{\parallel}}{C}-O-(CH_2)_3-CH_3$ |
| 3,5-bis(CF₃)pyrazol-1-yl | F | $-S-\underset{\underset{CH_3}{\mid}}{CH}-CN$ |
| 3,5-bis(CF₃)pyrazol-1-yl | F | $-S-CH_2-CH_2-O-CH_3$ |
| 3,5-bis(CF₃)pyrazol-1-yl | F | $-S-CH_2-CH(OCH_3)_2$ |
| 3,5-bis(CF₃)pyrazol-1-yl | H | $-OCH_3$ |
| 3,5-bis(CF₃)pyrazol-1-yl | H | $-OC_2H_5$ |
| 3,5-bis(CF₃)pyrazol-1-yl | H | $-O-CH(CH_3)_2$ |

-continued

| Pyrazole (3,5-bis-CF₃, N-) | H | —O—CH₂—CH=CH₂ |
| Pyrazole (3,5-bis-CF₃, N-) | H | —O—CH₂—CH=CH—CH₃ |
| Pyrazole (3,5-bis-CF₃, N-) | H | —O—CH₂—CH—Cl |
| Pyrazole (3,5-bis-CF₃, N-) | H | —O—CH—CH=CH₂<br>      \|<br>     CH₃ |
| Pyrazole (3,5-bis-CF₃, N-) | H | —O—CH₂—C≡CH |
| Pyrazole (3,5-bis-CF₃, N-) | H | —O—CH—C≡CH<br>      \|<br>     CH₃ |
| Pyrazole (3,5-bis-CF₃, N-) | H | —O—CH₂—C=CH₂<br>           \|<br>          CH₃ |
| Pyrazole (3,5-bis-CF₃, N-) | H | —O—CH₂—CH₂—OC₂H₅ |
| Pyrazole (3,5-bis-CF₃, N-) | H | —O—CH—CH₂—OC₂H₅<br>      \|<br>     CH₃ |

-continued
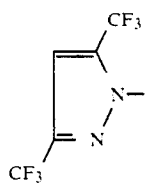 H 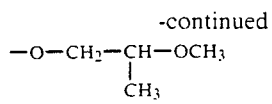
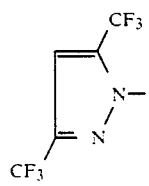 H 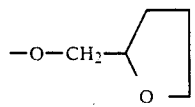
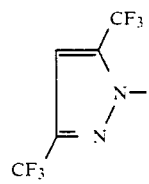 H 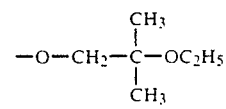
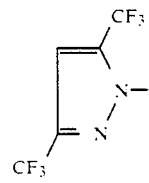 H —O—CH$_2$—CH$_2$—O—CH$_2$—CH$_2$—OCH$_3$
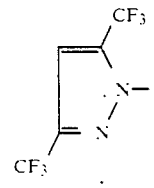 H —O—CH$_2$—CH$_2$—O—CH$_2$—CH$_2$—OC$_2$H$_5$
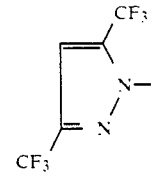 H 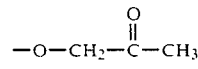
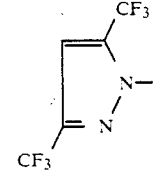 H 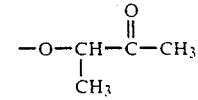
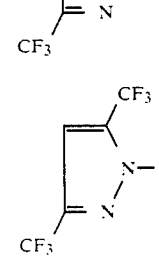 H —SCH$_3$
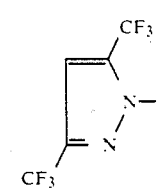 H —SC$_2$H$_5$ -continued
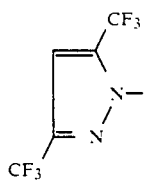 H —S—CH(CH₃)₂
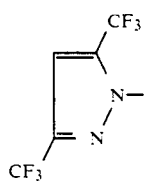 H —S—CH₂—CH=CH₂
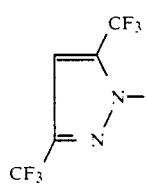 H —S—CH₂—CH=CH—Cl
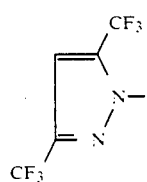 H —S—CH₂—CH=CH—CH₃
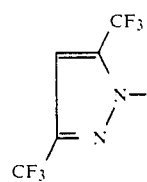 H —S—CH—CH=CH₂
               |
               CH₃
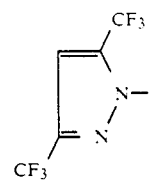 H —S—CH₂—C≡CH
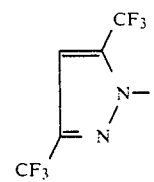 H —S—CH—C≡CH
               |
               CH₃
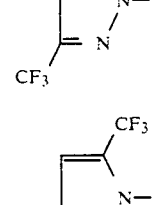 H —S—CH₂—C=CH₂
               |
               CH₃
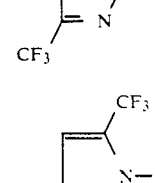 H —S—CH₂—CH₂—OC₂H₅

-continued
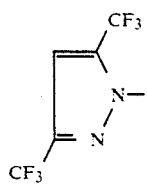 H 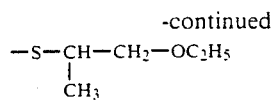
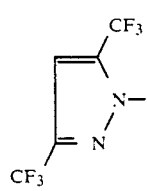 H 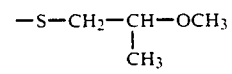
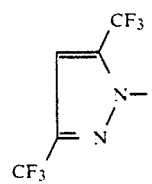 H 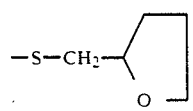
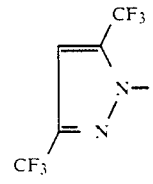 H 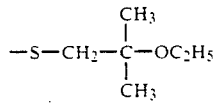
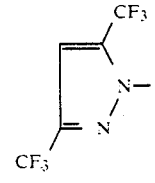 H 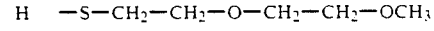
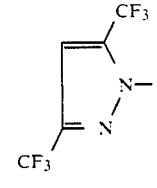 H 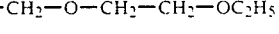
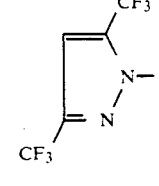 H 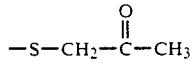
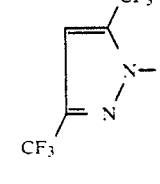 H 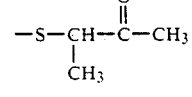
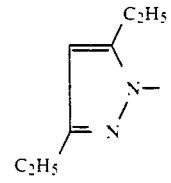 F 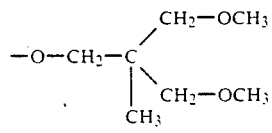

-continued
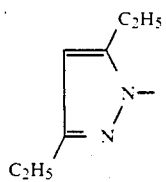 F 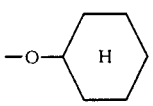
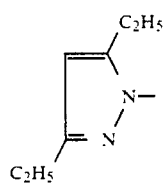 F 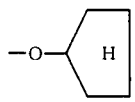
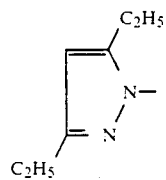 F 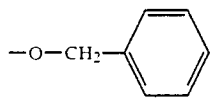
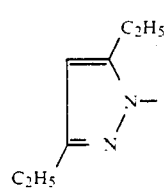 F 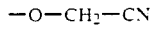
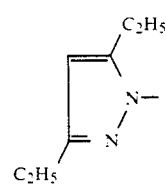 F 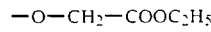
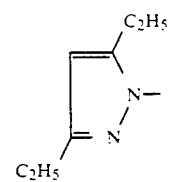 F 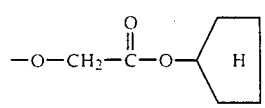
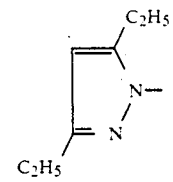 F 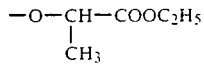
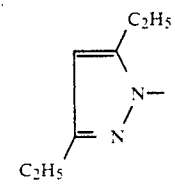 F 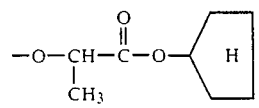
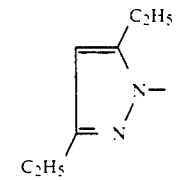 F 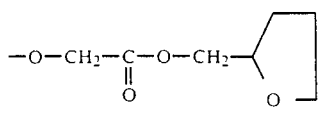

-continued
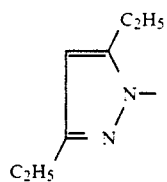 F 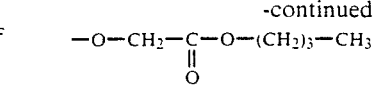
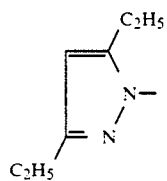 F 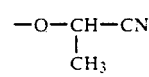
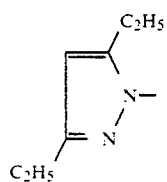 F —O—CH₂—CH₂—O—CH₃
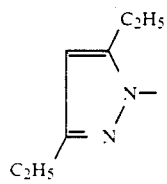 F 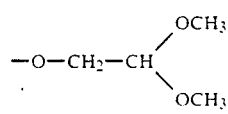
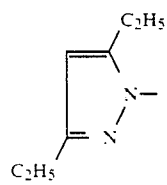 H 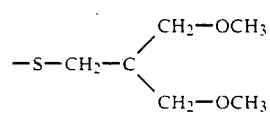
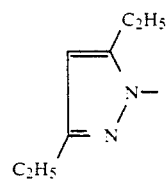 H 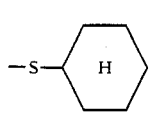
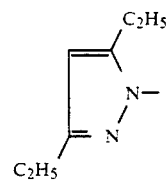 H 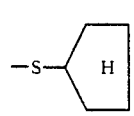
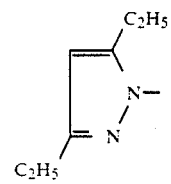 H 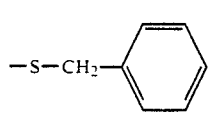
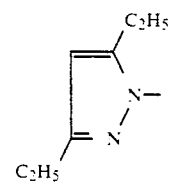 H —S—CH₂—CN -continued

| Pyrazole (3,5-diethyl-N-) | H | −S−CH₂−COOC₂H₅ |
| Pyrazole (3,5-diethyl-N-) | H | −S−CH₂−C(=O)−O−cyclopentyl(H) |
| Pyrazole (3,5-diethyl-N-) | H | −S−CH(CH₃)−COOC₂H₅ |
| Pyrazole (3,5-diethyl-N-) | H | −S−CH(CH₃)−C(=O)−O−cyclopentyl(H) |
| Pyrazole (3,5-diethyl-N-) | H | −S−CH₂−C(=O)−O−CH₂−(tetrahydrofuran-2-yl) |
| Pyrazole (3,5-diethyl-N-) | H | −S−CH₂−C(=O)−O−(CH₂)₃−CH₃ |
| Pyrazole (3,5-diethyl-N-) | H | −S−CH(CH₃)−CN |
| Pyrazole (3,5-diethyl-N-) | H | −S−CH₂−CH₂−O−CH₃ |
| Pyrazole (3,5-diethyl-N-) | H | −S−CH₂−CH(OCH₃)₂ |

-continued

| Pyrazole (3,5-diethyl, N-linked) | F | —OCH₃ |
| Pyrazole (3,5-diethyl, N-linked) | F | —OC₂H₅ |
| Pyrazole (3,5-diethyl, N-linked) | F | —O—CH(CH₃)₂ |
| Pyrazole (3,5-diethyl, N-linked) | F | —O—CH₂—CH=CH₂ |
| Pyrazole (3,5-diethyl, N-linked) | F | —O—CH₂—CH=CH—CH₃ |
| Pyrazole (3,5-diethyl, N-linked) | F | —O—CH₂—CH=CH—Cl |
| Pyrazole (3,5-diethyl, N-linked) | F | —O—CH(CH₃)—CH=CH₂ |
| Pyrazole (3,5-diethyl, N-linked) | F | —O—CH₂—C≡CH |
| Pyrazole (3,5-diethyl, N-linked) | F | —O—CH(CH₃)—C≡CH |

-continued
| | | |
|---|---|---|
| 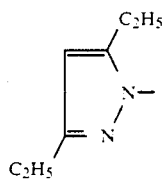 | F | 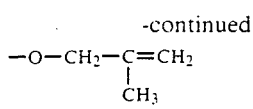 |
| 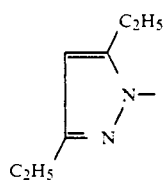 | F | —O—CH₂—CH₂—OC₂H₅ |
| 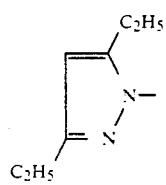 | F | 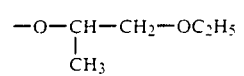 |
| 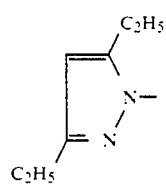 | F | 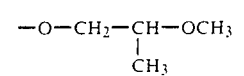 |
| 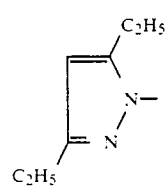 | F | 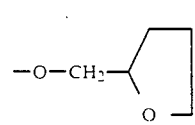 |
| 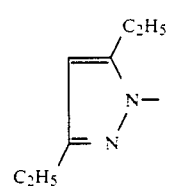 | F | 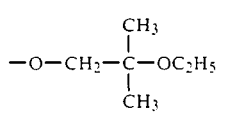 |
| 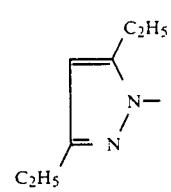 | F | —O—CH₂—CH₂—OCH₂—CH₂—OCH₃ |
| 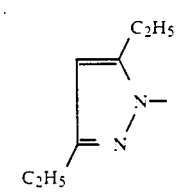 | F | —O—CH₂—CH₂—O—CH₂—CH₂—OC₂H₅ |
| 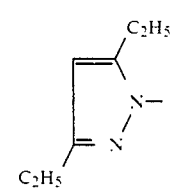 | F | 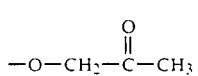 |

-continued
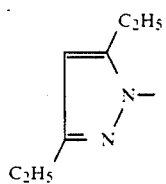 F $-O-CH(CH_3)-C(=O)-CH_3$
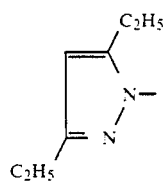 H $-SCH_3$
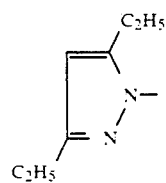 H $-SC_2H_5$
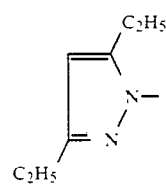 H $-S-CH(CH_3)_2$
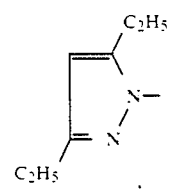 H $-S-CH_2-CH=CH_2$
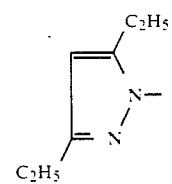 H $-S-CH_2-CH=CH-Cl$
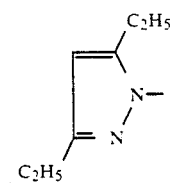 H $-S-CH_2-CH=CH-CH_3$
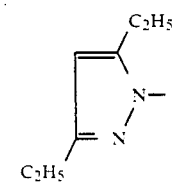 H $-S-CH(CH_3)-CH=CH_2$
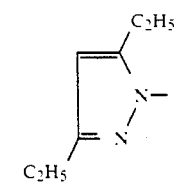 H $-S-CH_2-C\equiv CH$

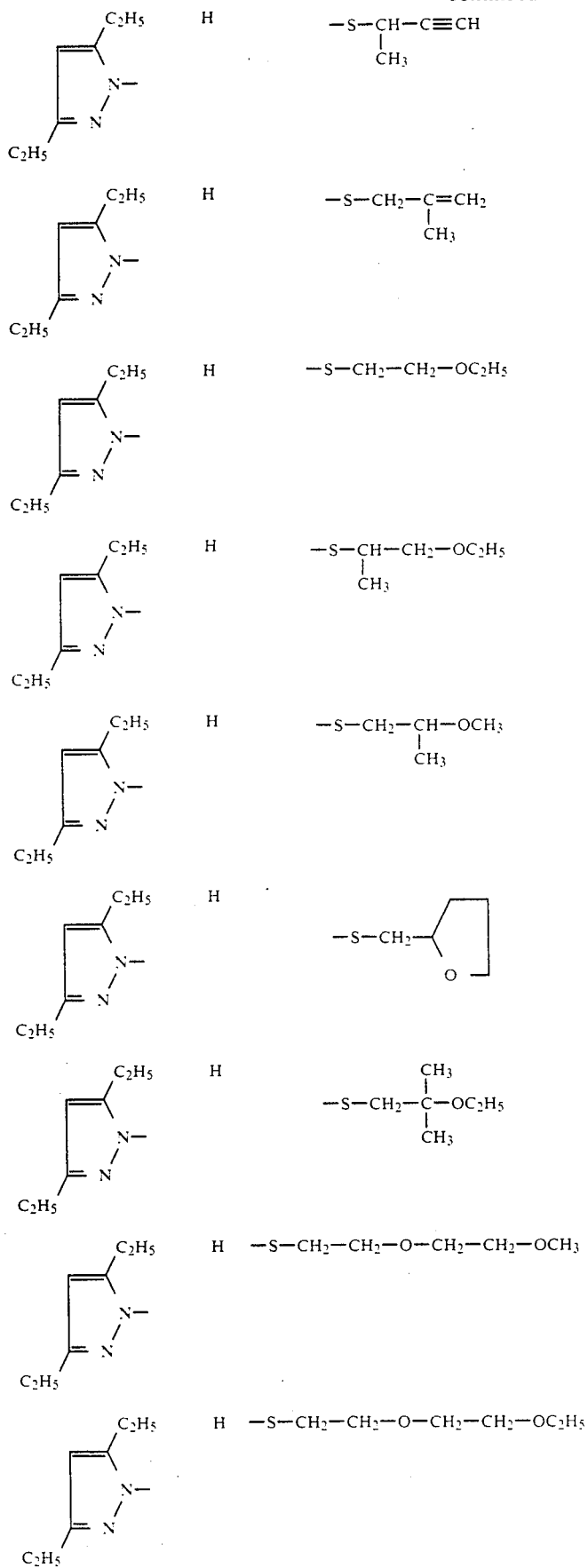

-continued
| | | |
|---|---|---|
| 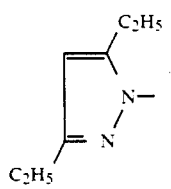 | H |  |
| 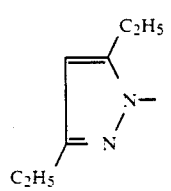 | H | 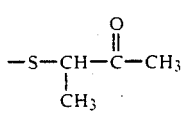 |
| 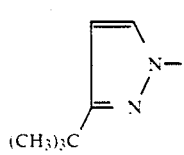 | F | 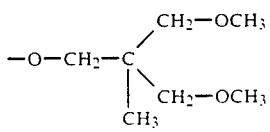 |
| 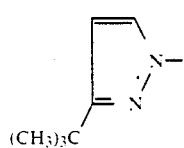 | F | 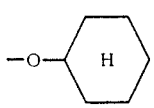 |
| 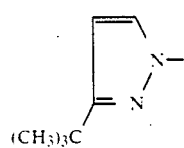 | F | 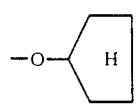 |
| 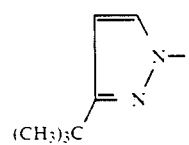 | F | 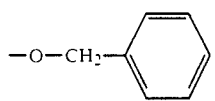 |
| 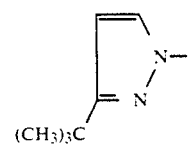 | F |  |
| 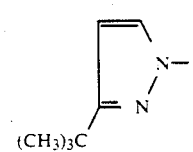 | F | 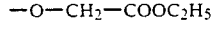 |
| 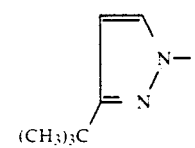 | F | 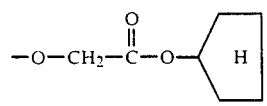 |
| 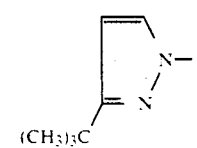 | F | 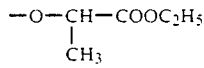 |

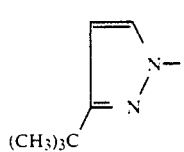 F 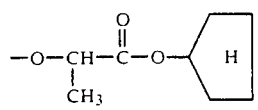
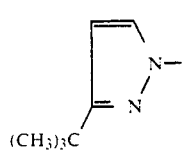 F 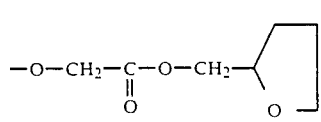
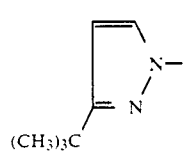 F 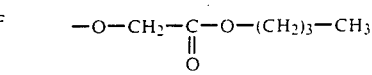
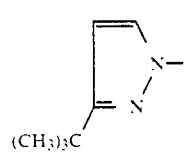 F 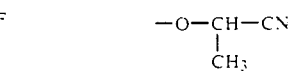
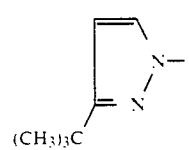 F —O—CH₂—CH₂—O—CH₃
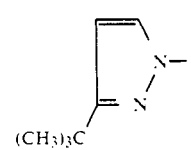 F 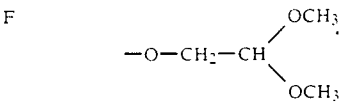
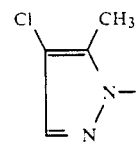 F —OCH₃
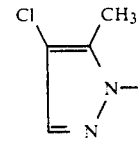 F —OC₂H₅
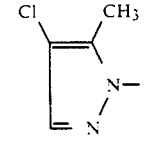 F —O—CH(CH₃)₂
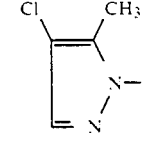 F —O—CH₂—CH=CH₂

-continued
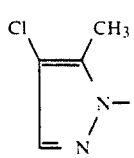  F  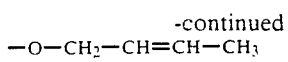
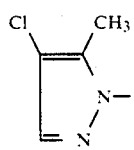  F  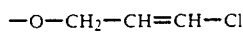
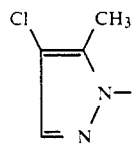  F  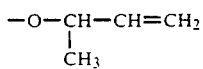
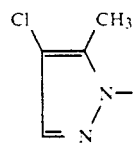  F  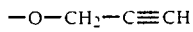
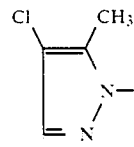  F  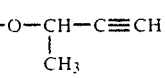
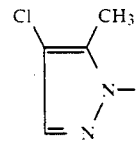  F  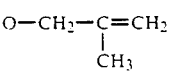
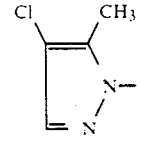  F  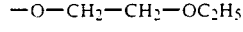
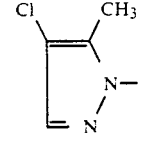  F  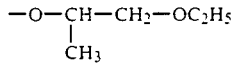
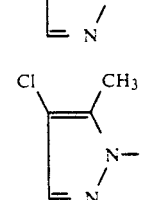  F  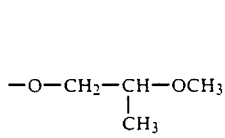
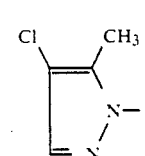  F  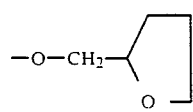
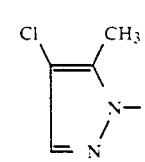  F  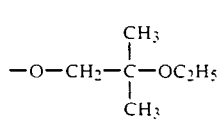

-continued

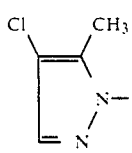 F  —O—CH$_2$—CH$_2$—O—CH$_2$—CH$_2$—OCH$_3$

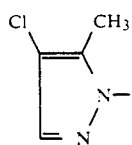 F  —O—CH$_2$—CH$_2$—O—CH$_2$—CH$_2$—OC$_2$H$_5$

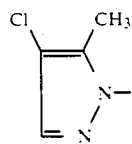 F  $-\text{O}-\text{CH}_2-\overset{\overset{\text{O}}{\|}}{\text{C}}-\text{CH}_3$

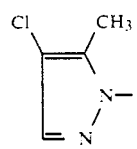 F  $-\text{O}-\underset{\underset{\text{CH}_3}{|}}{\text{CH}}-\overset{\overset{\text{O}}{\|}}{\text{C}}-\text{CH}_3$

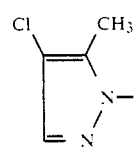 F  —SCH$_3$

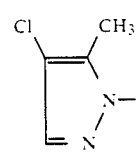 F  —SC$_2$H$_5$

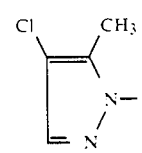 F  —S—CH(CH$_3$)$_2$

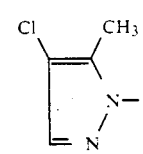 F  —S—CH$_2$—CH=CH$_2$

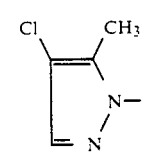 F  —S—CH$_2$—CH=CH—Cl

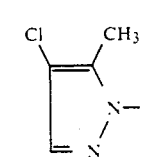 F  —S—CH$_2$—CH=CH—CH$_3$

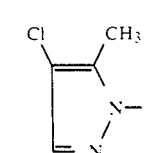 F  $-\text{S}-\underset{\underset{\text{CH}_3}{|}}{\text{CH}}-\text{CH}=\text{CH}_2$ -continued
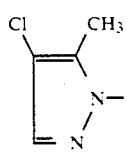 F  —S—CH$_2$—C≡CH
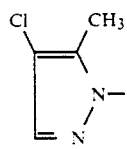 F  —S—CH(CH$_3$)—C≡CH
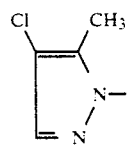 F  —S—CH$_2$—C(CH$_3$)=CH$_2$
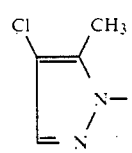 F  —S—CH$_2$—CH$_2$—OC$_2$H$_5$
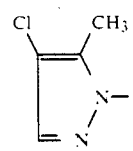 F  —S—CH(CH$_3$)—CH$_2$—OC$_2$H$_5$
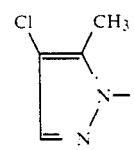 F  —S—CH$_2$—CH(CH$_3$)—OCH$_3$
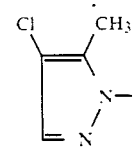 F 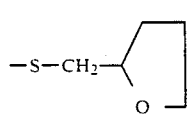
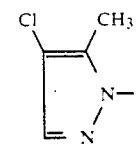 F  —S—CH$_2$—C(CH$_3$)$_2$—OC$_2$H$_5$
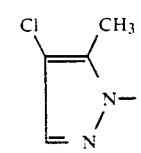 F  —S—CH$_2$—CH$_2$—O—CH$_2$—CH$_2$—OCH$_3$
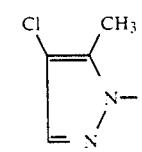 F  —S—CH$_2$—CH$_2$—O—CH$_2$—CH$_2$—OC$_2$H$_5$
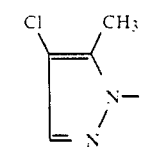 F  —S—CH$_2$—C(=O)—CH$_3$ -continued
| | | |
|---|---|---|
| 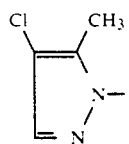 | F | 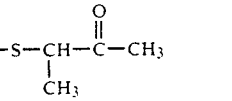 |
| 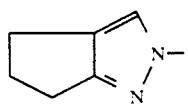 | F | 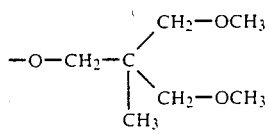 |
| 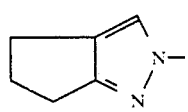 | F | 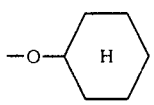 |
| 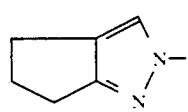 | F | 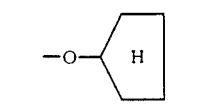 |
| 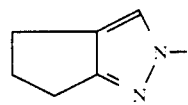 | F | 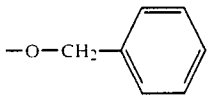 |
| 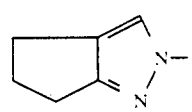 | F | 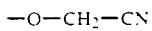 |
| 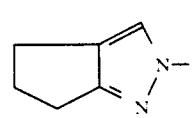 | F | 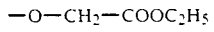 |
| 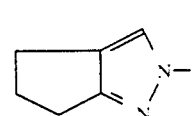 | F | 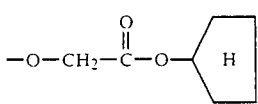 |
| 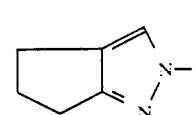 | F | 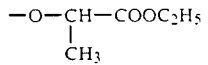 |
| 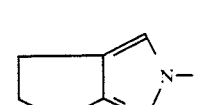 | F | 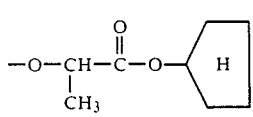 |
| 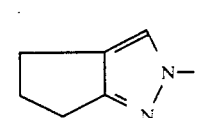 | F | 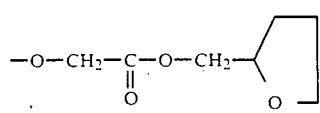 |
| 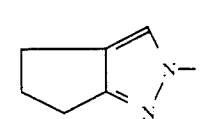 | F | 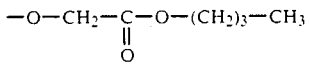 |
| 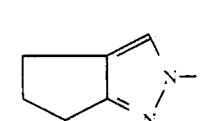 | F | 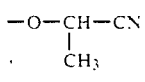 |

-continued
| | | |
|---|---|---|
| 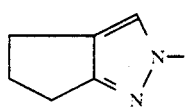 | F | —O—CH₂—CH₂—O—CH₃ |
| 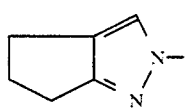 | F | 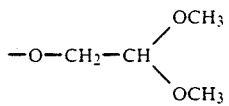 |
| 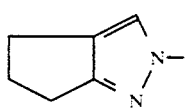 | F | 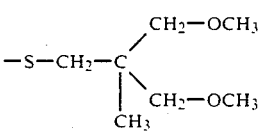 |
| 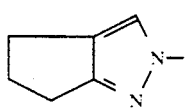 | F | 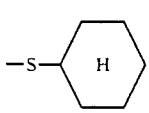 |
| 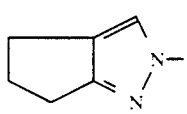 | F | 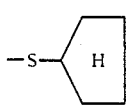 |
| 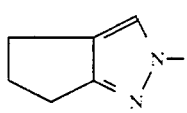 | F | 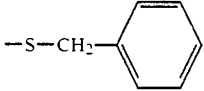 |
| 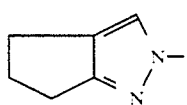 | F | —S—CH₂—CN |
| 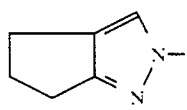 | F | —S—CH₂—COOC₂H₅ |
| 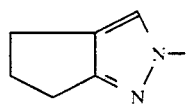 | F | 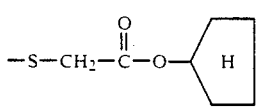 |
| 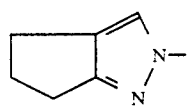 | F | 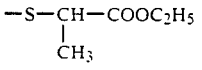 |
| 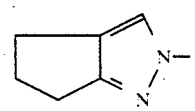 | F | 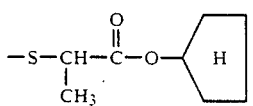 |
| 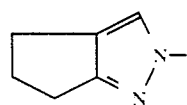 | F | 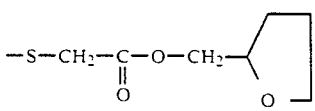 |
| 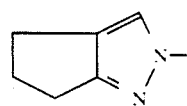 | F | 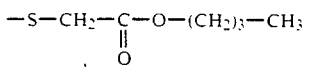 |

-continued
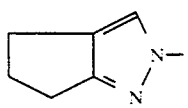 F 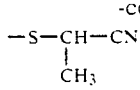
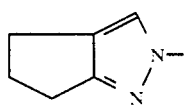 F —S—CH₂—CH₂—O—CH₃
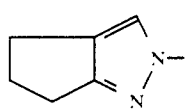 F —S—CH₂—CH(OCH₃)₂ (with OCH₃ shown above and below)
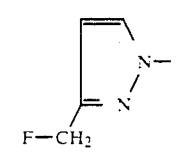 F —OCH₃
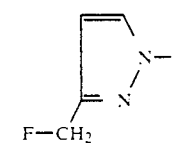 F —OC₂H₅
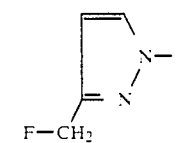 F —O—CH(CH₃)₂
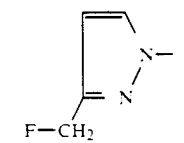 F —O—CH₂—CH=CH₂
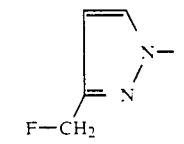 F —O—CH₂—CH=CH—CH₃
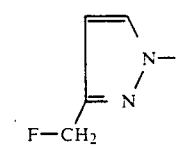 F —O—CH₂—CH=CH—Cl
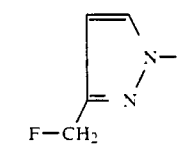 F —O—CH(CH₃)—CH=CH₂
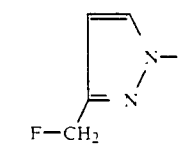 F —O—CH₂—C≡CH

| | | |
|---|---|---|
| 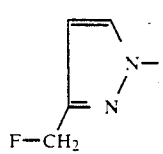 | F | 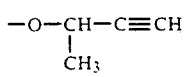 |
| 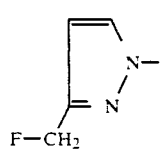 | F | 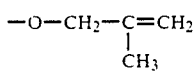 |
| 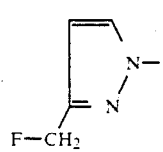 | F | 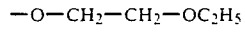 |
| 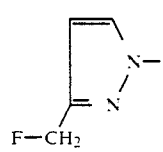 | F | 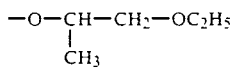 |
| 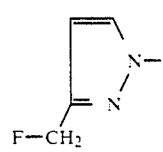 | F | 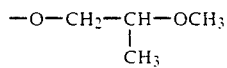 |
| 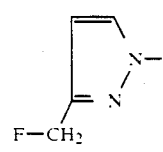 | F | 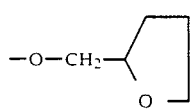 |
| 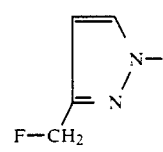 | F | 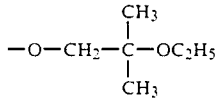 |
| 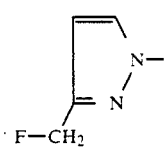 | F | 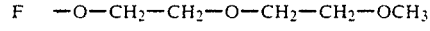 |
| 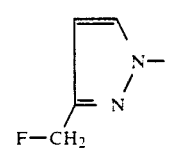 | F | 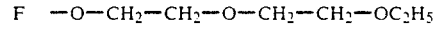 |
| 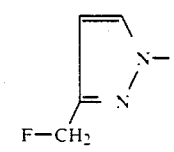 | F | 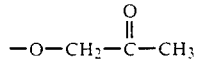 |

-continued
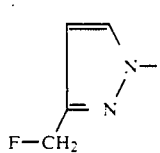 F −O−CH(CH₃)−C(=O)−CH₃
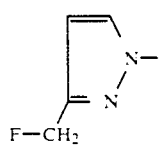 F −SCH₃
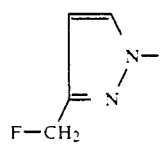 F −SC₂H₅
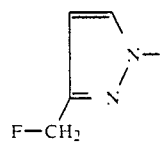 F −S−CH(CH₃)₂
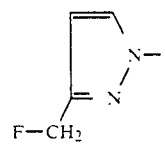 F −S−CH₂−CH=CH₂
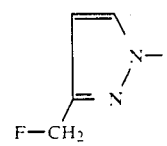 F −S−CH₂−CH=CH−Cl
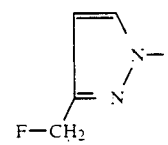 F −S−CH₂−CH=CH−CH₃
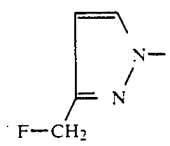 F −S−CH(CH₃)−CH=CH₂
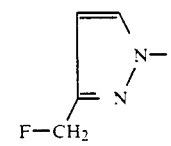 F −S−CH₂−C≡CH
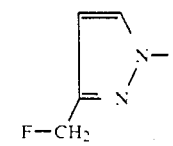 F −S−CH(CH₃)−C≡CH

| Pyrazole (F-CH₂ substituted) | F | Substituent |
|---|---|---|
| F-CH₂-pyrazol-N- | F | $-S-CH_2-C(CH_3)=CH_2$ |
| F-CH₂-pyrazol-N- | F | $-S-CH_2-CH_2-OC_2H_5$ |
| F-CH₂-pyrazol-N- | F | $-S-CH(CH_3)-CH_2-OC_2H_5$ |
| F-CH₂-pyrazol-N- | F | $-S-CH_2-CH(CH_3)-OCH_3$ |
| F-CH₂-pyrazol-N- | F | $-S-CH_2-\text{(tetrahydrofuran-2-yl)}$ |
| F-CH₂-pyrazol-N- | F | $-S-CH_2-C(CH_3)_2-OC_2H_5$ |
| F-CH₂-pyrazol-N- | F | $-S-CH_2-CH_2-O-CH_2-CH_2-OCH_3$ |
| F-CH₂-pyrazol-N- | F | $-S-CH_2-CH_2-O-CH_2-CH_2-OC_2H_5$ |
| F-CH₂-pyrazol-N- | F | $-S-CH_2-C(=O)-CH_3$ |
| F-CH₂-pyrazol-N- | F | $-S-CH(CH_3)-C(=O)-CH_3$ |

-continued
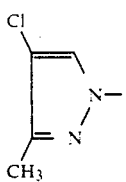 F 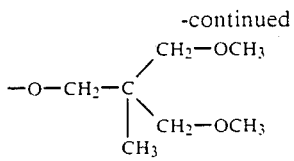
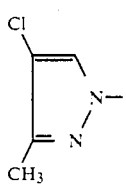 F 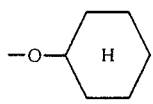
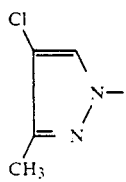 F 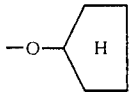
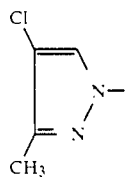 F 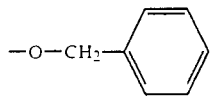
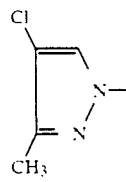 F 
—O—CH$_2$—CN
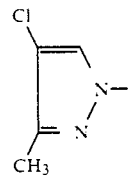 F 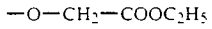
—O—CH$_2$—COOC$_2$H$_5$
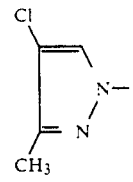 F 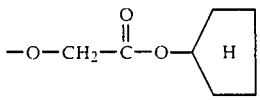
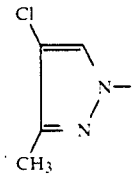 F 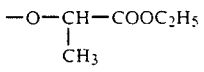
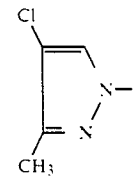 F 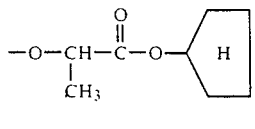

-continued
| | | |
|---|---|---|
| 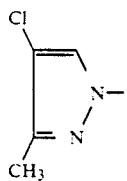 | F | 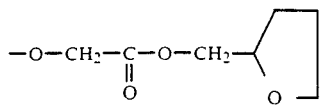 |
| 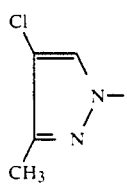 | F | —O—CH₂—C(=O)—O—(CH₂)₃—CH₃ |
| 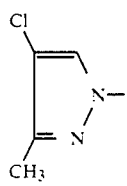 | F | —O—CH(CH₃)—CN |
| 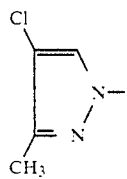 | F | —O—CH₂—CH₂—O—CH₃ |
|  | F | 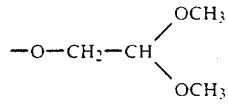 |
|  | F | 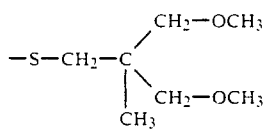 |
|  | F | 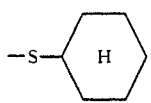 |
|  | F | 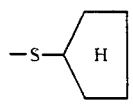 |
|  | F | 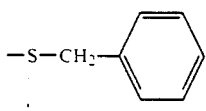 |

-continued
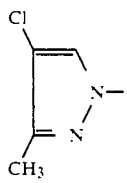 F 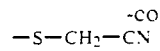
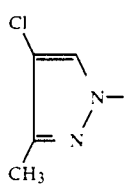 F 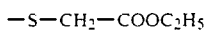
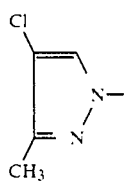 F 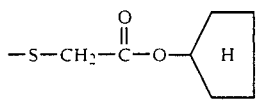
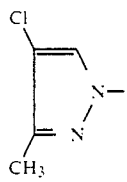 F 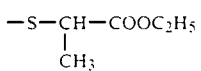
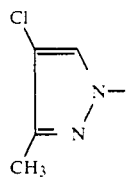 F 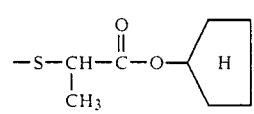
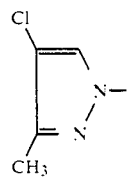 F 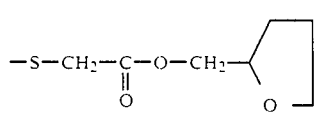
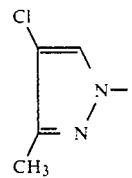 F 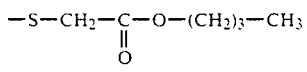
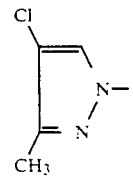 F 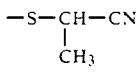
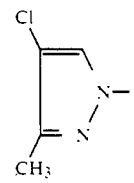 F 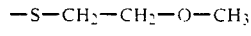

-continued
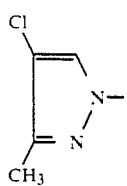 F  $-S-CH_2-CH\begin{smallmatrix}OCH_3\\OCH_3\end{smallmatrix}$
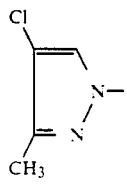 F  $-OCH_3$
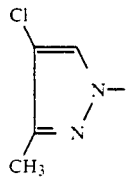 F  $-OC_2H_5$
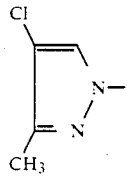 F  $-O-CH(CH_3)_2$
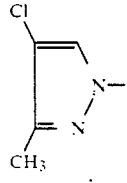 F  $-O-CH_2-CH=CH_2$
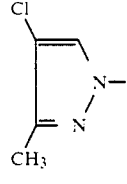 F  $-O-CH_2-CH=CH-CH_3$
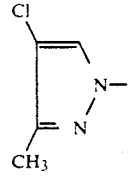 F  $-O-CH_2-CH=CH-Cl$
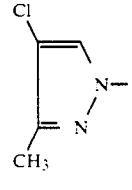 F  $-O-CH-CH=CH_2$
                           $\quad\quad\;\;|$
                           $\quad\quad\;\;CH_3$
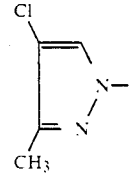 F  $-O-CH_2-C\equiv CH$ -continued

| Pyrazole (4-Cl, 3-CH₃) | F | —O—CH(CH₃)—C≡CH |
| Pyrazole (4-Cl, 3-CH₃) | F | —O—CH₂—C(CH₃)=CH₂ |
| Pyrazole (4-Cl, 3-CH₃) | F | —O—CH₂—CH₂—OC₂H₅ |
| Pyrazole (4-Cl, 3-CH₃) | F | —O—CH(CH₃)—CH₂—OC₂H₅ |
| Pyrazole (4-Cl, 3-CH₃) | F | —O—CH₂—CH(CH₃)—OCH₃ |
| Pyrazole (4-Cl, 3-CH₃) | F | —O—CH₂—(tetrahydrofuran-2-yl) |
| Pyrazole (4-Cl, 3-CH₃) | F | —O—CH₂—C(CH₃)₂—OC₂H₅ |
| Pyrazole (4-Cl, 3-CH₃) | F | —O—CH₂—CH₂—O—CH₂—CH₂—OCH₃ |
| Pyrazole (4-Cl, 3-CH₃) | F | —O—CH₂—CH₂—O—CH₂—CH₂—OC₂H₅ |

-continued
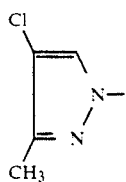 F —O—CH₂—C(=O)—CH₃
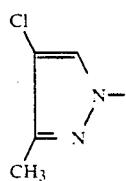 F —O—CH(CH₃)—C(=O)—CH₃
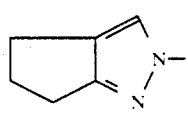 F —SCH₃
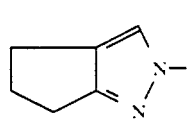 F —SC₂H₅
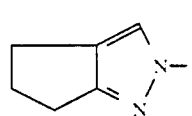 F —SC—CH(CH₃)₂
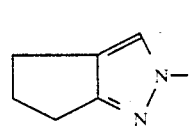 F —S—CH₂—CH=CH—CH₂
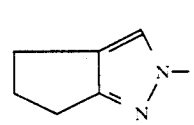 F —S—CH₂—CH=CH—Cl
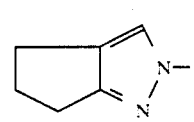 F —S—CH₂—CH=CH—CH₃
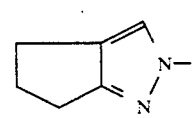 F —S—CH(CH₃)—CH=CH₂
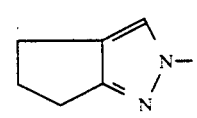 F —S—CH₂—C≡CH
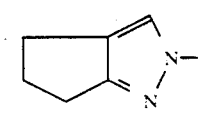 F —S—CH(CH₃)—C≡CH
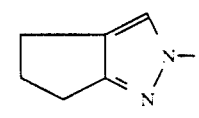 F —S—CH₂—C(CH₃)=CH₂

| | | |
|---|---|---|
| 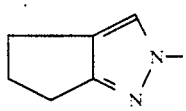 | F | —S—CH₂—CH₂—OC₂H₅ |
| 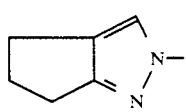 | F | —S—CH—CH₂—OC₂H₅<br>　　｜<br>　　CH₃ |
| 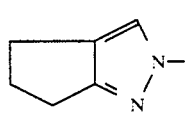 | F | —S—CH₂—CH—OCH₃<br>　　　　｜<br>　　　　CH₃ |
| 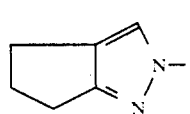 | F | 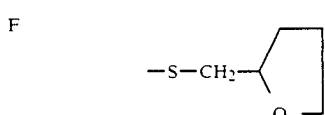 |
| 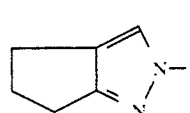 | F | 　　　CH₃<br>　　　｜<br>—S—CH₂—C—OC₂H₅<br>　　　｜<br>　　　CH₃ |
| 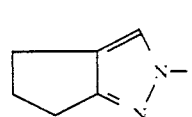 | F | —S—CH₂—CH₂—O—CH₂—CH₂—OCH₃ |
| 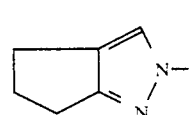 | F | —S—CH₂—CH₂—O—CH₂—CH₂—OC₂H₅ |
| 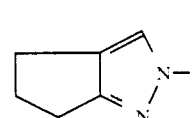 | F | 　　　　　O<br>　　　　　‖<br>—S—CH₂—C—CH₃ |
| 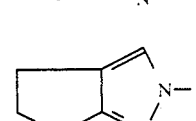 | F | 　　　　　O<br>　　　　　‖<br>—S—CH—C—CH₃<br>　　｜<br>　　CH₃ |

If, for example, 4-cyano-2,5-difluorophenylhydrazine and acetylacetone are used as the starting substances, the course of the reaction of process (a) according to the invention may be represented by the following equation:

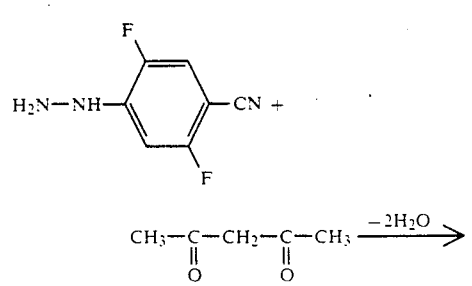

-continued

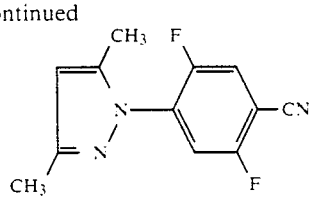

If, for example, 4-(3,5-dimethylpyrazol-1-yl)-2,5-difluorobenzonitrile is used as the starting compound and sulphuryl chloride as the halogenating agent, the course of the reaction of process (b) according to the invention may be represented by the following equation:

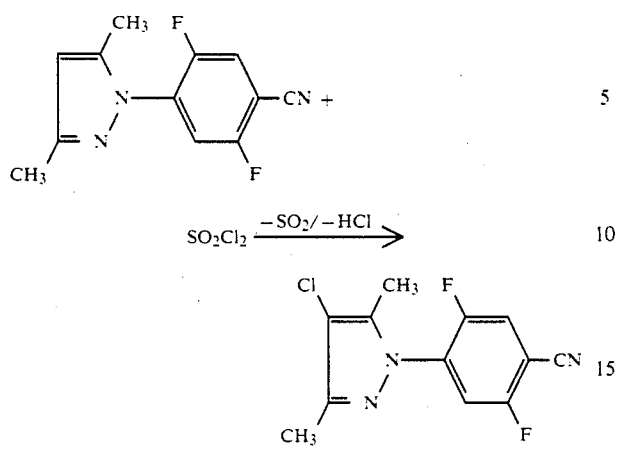

If, for example. 1-(2,5-difluoro-4-cyanophenyl)-4H-pyrazolin-5-one is used as the starting compound and phosphorus oxychloride in the presence of triphenylphosphine is used as the halogenating agent, the course of the reaction of process (c) according to the invention may be represented by the following equation:

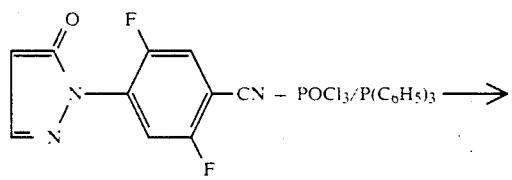

If, for example, 4-cyano-2-fluoro-5-isopropoxyphenylhydrazine and ethyl N-ethoxycarbonyl-2,2-dimethylpropaneimidate are used as the starting substances, the course of the reaction of process (d) according to the invention may be represented by the following equation:

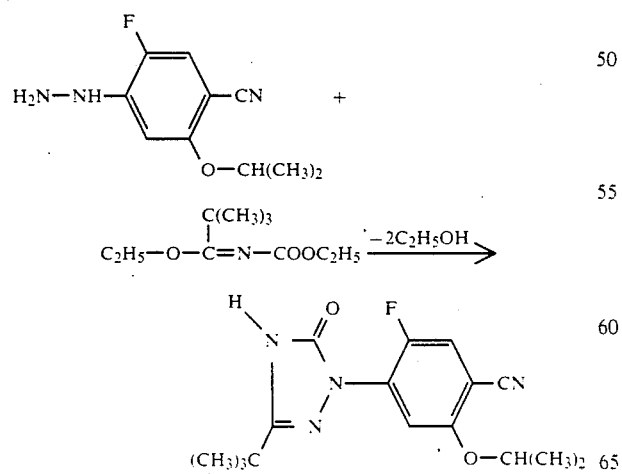

If, for example, 1-(4-cyano-2-fluoro-5-allyloxyphenyl)-3-t-butyl-4H-1,2,4-triazolin-5-one and propargyl bromide are used as the starting substances, the course of the reaction of process (e) according to the invention may be represented by the following equation:

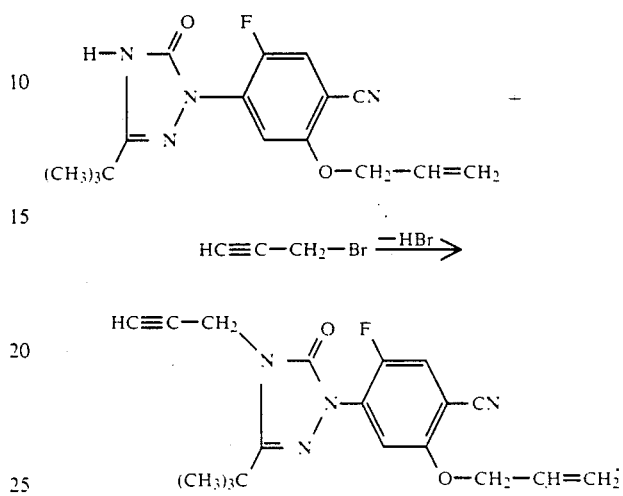

If, for example, piperidin-2-one-(2,5-difluoro-4-cyanophenylhydrazone is used as the starting compound, the course of the reaction of process (f) according to the invention may be represented by the following equation:

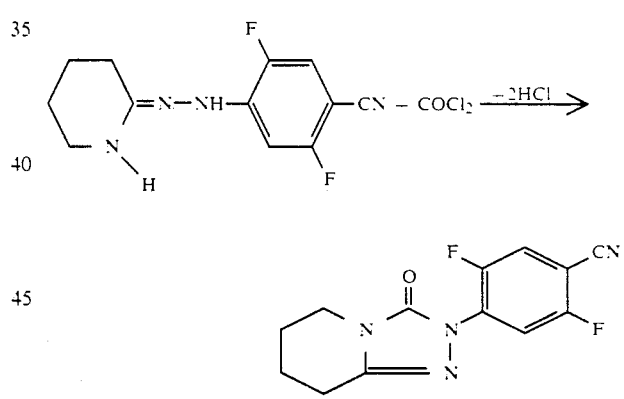

If, for example, N-pivaloyl-N'-(4-cyano-2-fluoro-5-methoxyphenyl)-hydrazine is used as the starting compound, the course of the reaction of process (g) according to the invention may be represented by the following equation:

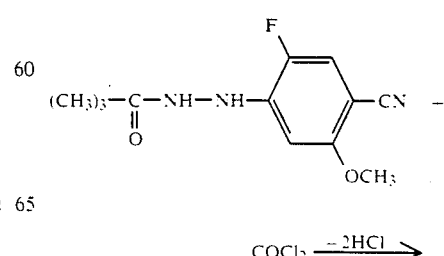

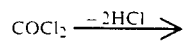

-continued

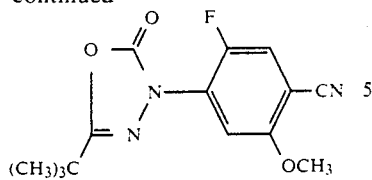

If, for example, 4-(3,4,5-trimethylpyrazol-1-yl)-2-fluorobenzonitrile and t-butylmercaptan are used as the starting substances, the course of the reaction of process (h-α) according to the invention may be represented by the following equation:

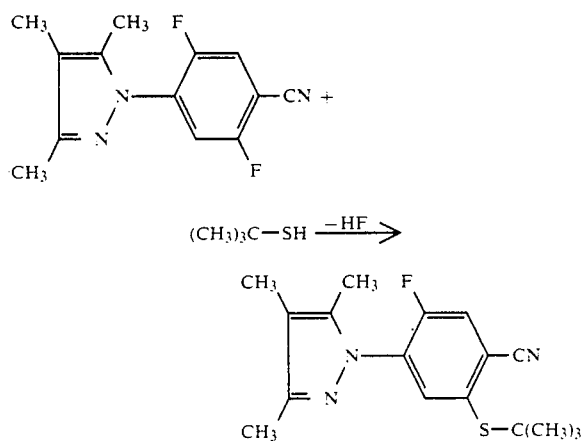

If, for example, 4-(1-pyrazolyl)-2-hydroxybenzonitrile and allyl bromide are used as the starting substances, the course of the reaction of process (h-β) according to the invention may be represented by the following equation:

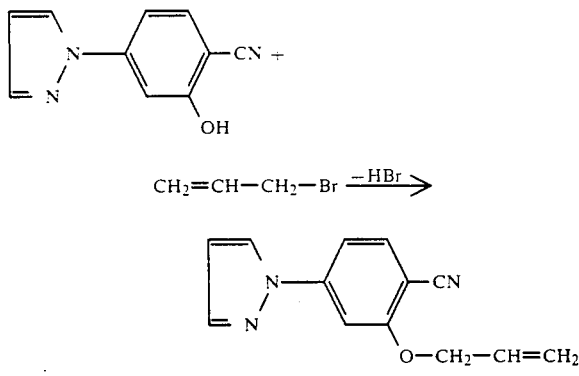

If, for example, 4-(3,5-dimethyl-4-ethoxycarbonyl-pyrazol-1-yl)-2,5-difluorobenzonitrile is used as the starting compound, the course of the reaction of process (i) according to the invention may be represented by the following equation:

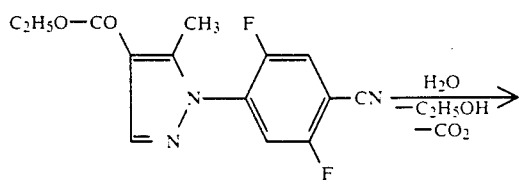

-continued

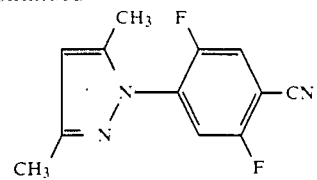

Formula (II) provides a general definition of the 4-cyanophenylhydrazines required as starting substances for carrying out processes (a) and (d) according to the invention. In this formula (II), $R^1$ and $R^2$ preferably represent those radicals which have already been mentioned in connection with the description of the substances of the formula (I) according to the invention as being preferred for these substituents.

The 4-cyanophenylhydrazines of the formula (II) were hitherto unknown and are also a subject of the invention.

They are obtained when 4-fluorobenzonitriles of the formula (XIII)

in which
$R^{2-1}$ represents halogen and
$R^1$ has the abovementioned meaning,
are reacted with hydrazine hydrate, if appropriate in the presence of a diluent, such as, for example, ethanol, at temperatures between 20° C. and 130° C., and the resulting 4-cyano-phenylhydrazines of the formula (IIa)

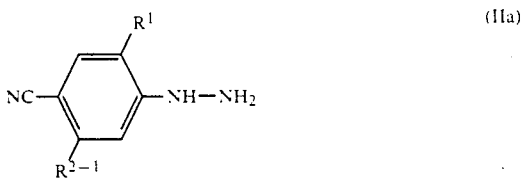

in which
$R^1$ and $R^{2-1}$ have the abovementioned meaning,
are, if required, reacted in a following 2nd step with alcohols or thiols of the formula (IX)

$$R^9—XH \qquad (IX)$$

in which
$R^9$ represents in each case optionally substituted alkyl, alkenyl, alkinyl or cycloalkyl and
X represents oxygen or sulphur,
if appropriate in the presence of a diluent, such as, for example, acetonitrile, and if appropriate in the presence of a reaction auxiliary, such as, for example, sodium hydride or potassium hydroxide, at temperatures between 0° C. and 80° C.

Alternatively, 4-cyanophenylhydrazines of the formula (IIb)

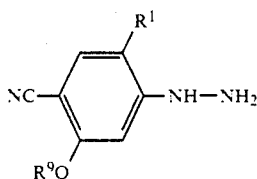

in which

R¹ has the abovementioned meaning and

R⁹ represents in each case optionally substituted alkyl, alkenyl, alkinyl or cycloalkyl, are also obtained when 4-aminobenzonitriles of the formula (XIV)

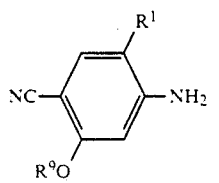

in which

R¹ and R⁹ have the abovementioned meaning, are first diazotized in a customary manner, using sodium nitrite in the presence of an acid such as, for example, hydrochloric acid, and the product is subsequently reduced using a reducing agent, such as, for example, tin(II) chloride, likewise in a generally customary manner.

4-Fluorobenzonitriles of the formula (XIII) are known or can be obtained in analogy to known processes (cf., for example, European Patent 191,185; U.S. Pat. No. 3,978,127; DE 2,104,312; J. Heterocycl. Chem. 15, 1373-1378 [1978]; DE 2,711,332; PCT Int. Appl. WO87/7602; Japanese Patent 56/79,660; Zh. org. Khim. 3, 1257-1259 [1967]; J. Chem. Res., Synop. 1984, 382-383; Collect. Czech. Chem. Commun. 49, 992-1000 [1984]; Collect. Czech. Chem. Commun. 42, 2001-2017 [1977]).

4-Aminobenzonitriles of the formula (XIV) are likewise known or can be obtained in analogy to known processes (cf., for example, Japanese Patent 46/3368; European Patent 100,172 or European Patent 224,001).

Formula (III) provides a general definition of the 1,3-diketones furthermore required as starting substances for carrying out process (a) according to the invention. In this formula (III), R³ preferably represents those radicals which have already been mentioned in connection with the description of the substances of the formula (I) according to the invention as being preferred for these substituents.

R⁴⁻¹ preferably represents hydrogen, represents straight-chain or branched alkyl having 1 to 6 carbon atoms or represents straight-chain or branched halogenoalkyl having 1 to 4 carbon atoms and 1 to 9 identical or different halogen atoms, in particular represents hydrogen, methyl, ethyl, n- or i-propyl, n-, i-, s- or t-butyl, represents fluoromethyl, difluoromethyl, trifluoromethyl, chloromethyl, dichloromethyl, trichloromethyl, difluorochloromethyl or dichlorofluoromethyl.

R⁵⁻¹ preferably represents hydrogen, represents straight-chain or branched alkyl having 1 to 6 carbon atoms or represents straight-chain or branched halogenoalkyl having 1 to 4 carbon atoms and 1 to 9 identical or different halogen atoms, in particular represents hydrogen, methyl, ethyl, n- or i-propyl, n-, i-, s- or t-butyl, represents fluoromethyl, difluoromethyl, trifluoromethyl, chloromethyl, dichloromethyl, trichloromethyl, difluorochloromethyl or dichlorofluoromethyl.

1,3-Diketones of the formula (III) and derivatives of these diketones, such as, for example, enol ethers, enol esters, ketals, enol ether ketals, enamines or β-halogenovinyl ketones are generally known compounds of organic chemistry.

Formula (Ij) provides a general definition of the N-aryl-substituted nitrogen-containing heterocycles required as starting substances for carrying out process (b) according to the invention. In this formula (Ij), R¹, R² and R³ preferably represent those radicals which have already been mentioned in connection with the description of the substances of the formula (I) according to the invention as being preferred for these substituents.

R⁵⁻¹ preferably represents hydrogen, represents straight-chain or branched alkyl having 1 to 6 carbon atoms or represents straight-chain or branched halogenoalkyl having 1 to 4 carbon atoms and 1 to 9 identical or different halogen atoms, in particular represents hydrogen, methyl, ethyl, n- or i-propyl, n-, i-, s- or t-butyl, represents fluoromethyl, difluoromethyl, trifluoromethyl, chloromethyl, dichloromethyl, trichloromethyl, difluorochloromethyl or dichlorofluoromethyl.

The N-aryl-substituted nitrogen-containing heterocycles of the formula (Ij) are compounds according to the invention and can be obtained by means of processes (a), (h-α), (h-β) and (i) according to the invention.

Formula (IV) provides a general definition of the N-arylpyrazolinones required as starting substances for carrying out process (c) according to the invention. In this formula (IV), R¹, R², R³ and R⁴ preferably represent those radicals which have already been mentioned in connection with the description of the substances of the formula (I) according to the invention as being preferred for these substituents.

The N-arylpyrazolinones of the formula (IV) were hitherto unknown and are likewise a subject of the invention. They are obtained when β-keto esters of the formula (XV)

in which

R¹³ represents alkyl, in particular represents methyl or ethyl, and

R³ and R⁴ have the abovementioned meaning, are reacted with 4-cyanophenylhydrazines of the formula (II)

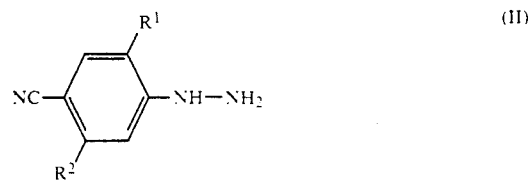

in which

R¹ and R² have the abovementioned meaning.

if appropriate in the presence of a diluent, such as, for example, ethanol, and, if appropriate, in the presence of a reaction auxiliary, such as, for example, sulphuric acid, at temperatures between 20° C. and 120° C.

β-Keto esters of the formula (XV) are generally known compounds of organic chemistry.

Formula (V) provides a general definition of the iminocarboxylic acid esters required as starting substances for carrying out process (d) according to the invention. In this formula (V), $R^7$ preferably represents those radicals which have already been mentioned in connection with the description of the substances of the formula (I) according to the invention as being preferred for this substituent.

$R^{10}$ and $R^{11}$ each preferably represent independently of one another straight-chain or branched alkyl having 1 to 4 carbon atoms, in particular represent methyl or ethyl.

The iminocarboxylic acid esters of the formula (V) are known or can be obtained in analogy to known processes (cf., for example, Chem. Ber. 119, 2444–2457 [1986]; Bull. chem. Soc. Jpn. 55, 3943–3944 [1982]; Chem. Lett. 1982, 1015–1016; Chem. Lett. 1978, 1403–1404; J. Amer. chem. Soc. 95, 3957–3963 [1973]; J. org. Chem. 36, 3251–3252 [1971]).

Formula (Id) provides a general definition of the N-aryl-substituted nitrogen-containing heterocycles required as starting substances for carrying out process (e) according to the invention. In this formula (Id), $R^1$, $R^2$ and $R^7$ preferably represent those radicals which have already been mentioned in connection with the description of the substances of the formula (I) according to the invention as being preferred for these substituents.

The N-aryl-substituted nitrogen-containing heterocycles of the formula (Id) are compounds according to the invention and can be obtained by means of process (d) according to the invention.

Formula (VI) provides a general definition of the alkylating agents furthermore required as starting substances for carrying out process (e) according to the invention. In this formula (VI), $R^{8\text{-}1}$ preferably represents in each case straight-chain or branched alkyl having 1 to 6 carbon atoms, alkenyl having 3 to 6 carbon atoms, alkinyl having 3 to 6 carbon atoms, halogenoalkyl having 1 to 4 carbon atoms and 1 to 9 identical or different halogen atoms, halogenoalkenyl having 3 to 6 carbon atoms and 1 to 5 identical or different halogen atoms or halogenoalkinyl having 3 to 6 carbon atoms and 1 to 5 identical or different halogen atoms.

$R^{8\text{-}1}$ in particular represents methyl, ethyl, n- or i-propyl, n-, i-, s- or t-butyl, represents methyl, ethyl or t-butyl, each of which is monosubstituted, disubstituted or trisubstituted by fluorine and/or chlorine, represents allyl, represents n- or i-butenyl, represents chloroallyl, represents dichloroallyl, represents propargyl or represents chloropropargyl.

$E^1$ preferably represents halogen, in particular represents chlorine, bromine or iodine, or represents in each case optionally substituted alkylsulphonyloxy, alkoxysulphonyloxy or alkylsulphonyloxy, such as, for example, methanesulphonyloxy, trifluoromethanesulphonyloxy, methoxysulphonyloxy, ethoxysulphonyloxy or p-toluenesulphonyloxy.

The alkylating agents of the formula (VI) are generally known compounds of organic chemistry.

Formula (VII) provides a general definition of the amidrazones required as starting substances for carrying out process (f) according to the invention. In this formula (VII), $R^1$ and $R^2$ preferably represent those radicals which have already been mentioned in connection with the description of the substances of the formula (I) according to the invention as being preferred for these substituents.

Preferably, $R^{7\text{-}1}$ and $R^{8\text{-}2}$ together represent a doublelinked alkanediyl radical having 2 to 6 carbon atoms, in particular represent a 1,3-propanediyl radical, a 1,4-butanediyl radical or a 1,5-pentanediyl radical.

The amidrazones of the formula (VII) were hitherto unknown. They are obtained in analogy to known processes (cf., for example, U.S. Pat. No. 4,080,192 or DE-OS (German Published Specification) 1,957,783), when lactams of the formula (XVI)

in which
$R^{7\text{-}1}$ and $R^{8\text{-}2}$ have the abovementioned meaning,
are initially reacted in a 1st step with a halogenating agent, such as, for example, phosphorus oxychloride, thionyl chloride or phosgene, if appropriate in the presence of a diluent, such as, for example, ethanol or dioxane, and, if appropriate, in the presence of a reaction auxiliary, such as, for example, triethylamine or pyridine, at temperatures between 0° C. and 50° C., and the resulting imide chlorides of the formula (XVII)

in which
$R^{7\text{-}1}$ and $R^{8\text{-}2}$ have the abovementioned meaning,
are subsequently reacted with 4-cyanophenylhydrazines of the formula (II)

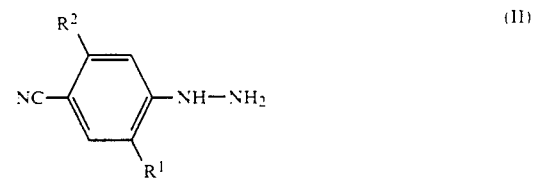

in which
$R^1$ and $R^2$ have the abovementioned meaning,
if appropriate in the presence of a diluent, such as, for example, ethanol, and, if appropriate, in the presence of a reaction auxiliary, such as, for example, triethylamine or pyridine, at temperatures between 0° C. and 80° C.

Lactams of the formula (XVI) are generally known compounds of organic chemistry.

Formula (VIII) provides a general definition of the phenyl hydrazides required as starting substances for carrying out process (g). In this formula (VIII), $R^1$, $R^2$ and $R^6$ preferably represent those radicals which have already been mentioned in connection with the description of the substances of the formula (L) according to the invention as being preferred for these substituents.

The phenyl hydrazides of the formula (VIII) were hitherto unknown.

They are obtained when 4-cyanophenylhydrazines of the formula (II)

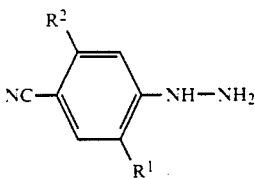

(II)

in which
R¹ and R² have the abovementioned meaning,
are reacted with acylating agents of the formula (XVIII)

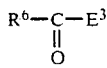

(XVIII)

in which
R⁶ has the abovementioned meaning and
E³ represents an electron-withdrawing leaving group, preferably represents halogen or represents a radical

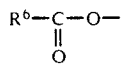

where R⁶ has the abovementioned meaning and in particular represents chlorine,
if appropriate in the presence of a diluent, such as, for example, dichloromethane, and, if appropriate, in the presence of a reaction auxiliary, such as, for example, triethylamine, at temperatures between −20° C. and +60° C.

Acylating agents of the formula (XVIII) are generally known compounds of organic chemistry.

Formula (Ik) provides a general definition of the N-aryl-substituted nitrogen-containing heterocycles required as starting substances for carrying out process (h-α) according to the invention. In this formula (Ik), R¹, R³, R⁴ and R⁵ preferably represent those radicals which have already been mentioned in connection with the description of the substances of the formula (I) according to the invention as being preferred for these substituents.

R²⁻¹ preferably represents fluorine, chlorine or bromine, in particular represents fluorine.

The N-aryl-substituted nitrogen-containing heterocycles of the formula (Ik) are compounds according to the invention and can be obtained by means of processes (a), (b), (c) or (i) according to the invention.

Formula (IX)) represents a general definition of the alcohols or thiols furthermore required as starting substances for carrying out process (h-α) according to the invention. In this formula (IX), R⁹ and X preferably represent those radicals which have already been mentioned in connection with the description of the substances of the formula (I) according to the invention as being preferred for these substituents.

The alcohols and thiols of the formula (IX) are generally known compounds of organic chemistry.

Formula (X) provides a general definition of the (thio)phenol derivatives required as starting substances for carrying out process (h-β) according to the invention. In this formula (X), R¹, R³, R⁴, R⁵ and X preferably represent those radicals which have already been mentioned in connection with the description of the substances of the formula (I) according to the invention as being preferred for these substituents.

The (thio)phenol derivatives of the formula (X) were hitherto unknown and are likewise a subject of the invention.

They are obtained either when N-aryl-substituted nitrogen-containing heterocycles of the formula (Ik)

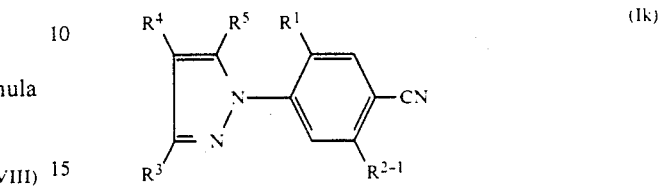

(Ik)

in which
R²⁻¹ represents halogen, in particular represents fluorine, and
R¹, R³, R⁴ and R⁵ have the abovementioned meaning,
are reacted with sodium hydrogen sulphide, if appropriate in the presence of a diluent, such as, for example, methanol, ethanol or their mixtures with water, and, if appropriate, in the presence of a reaction auxiliary, such as, for example, sodium hydroxide or potassium carbonate, if appropriate in the presence of a nitrogen or argon protective gas atmosphere, at temperatures between 0° C. and 50° C., or when N-aryl-substituted nitrogen-containing heterocycles of the formula (Il)

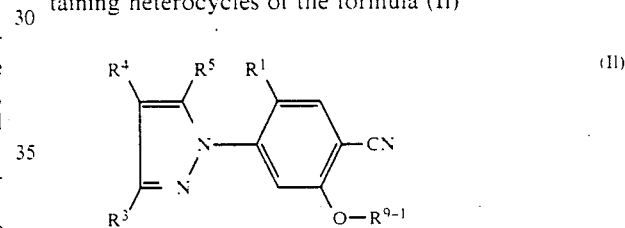

(Il)

in which
R¹, R³, R⁴ and R⁵ have the abovementioned meaning and
R⁹⁻¹ represents allyl or represents benzyl,
are reacted with customary reducing agents, such as, for example, molecular hydrogen in the presence of a customary hydrogenation catalyst, such as trimethylsilyl iodide or such as tris-triphenylphosphim-rhodium chloride, if appropriate in the presence of a diluent, such as, for example, ethanol or dichloromethane, and, if appropriate, in the presence of a reaction auxiliary, such as, for example, diazabicyclooctane (DABCO), at temperatures between 20° C. and 120° C.

N-Aryl-substituted nitrogen-containing heterocycles of the formula (Ik) are compounds according to the invention and can be obtained by means of processes (a), (b), (c) or (i) according to the invention.

N-Aryl-substituted nitrogen-containing heterocycles of the formula (Il) are likewise compounds according to the invention and can be obtained by means of processes (a), (b), (c) and (i) according to the invention.

Formula (XI) provides a general definition of the alkylating agents furthermore required as starting substances for carrying out process (h-β) according to the invention. In this formula (XI), R⁹ preferably represents those radicals which have already been mentioned in connection with the description of the substances of the formula (I) according to the invention as being preferred for this substituent.

$E^2$ preferably represents halogen, in particular represents chlorine, bromine or iodine, or represents in each case optionally substituted alkylsulphonyloxy, alkoxysulphonyloxy or arylsulphonyloxy, such as, for example, methanesulphonyloxy, trifluoromethanesulphonyloxy, methoxysulphonyloxy, ethoxysulphonyloxy or p-toluenesulphonyloxy.

The alkylating agents of the formula (XI) are generally known compounds of organic chemistry.

Formula (XII) provides a general definition of the N-arylpyrazolyl-4-carboxylic acid esters required as starting substances for carrying out process (i) according to the invention. In this formula (XII), $R^1$, $R^2$, $R^3$ and $R^5$ preferably represent those radicals which have already been mentioned in connection with the description of the substances of the formula (I) according to the invention as being preferred for these substituents.

$R^{12}$ preferably represents straight-chain or branched alkyl having 1 to 4 carbon atoms, in particular represents methyl or ethyl.

The N-arylpyrazolyl-4-carboxylic acid esters of the formula (XII) were hitherto unknown.

They are obtained when acrylic ester derivatives of the formula (XIX)

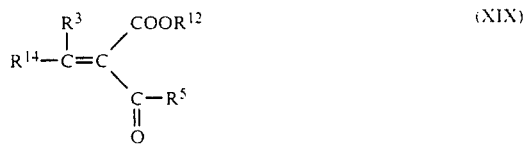

in which
$R^3$, $R^5$ and $R^{12}$ have the abovementioned meaning and
$R^{14}$ represents an alkoxy radical or represents a dialkylamino radical having in each case 1 to 4 carbon atoms in the individual straight-chain or branched alkyl moieties, in particular having in each case 1 to 2 carbon atoms in the individual alkyl moieties,
are reacted with 4-cyanophenylhydrazines of formula (II)

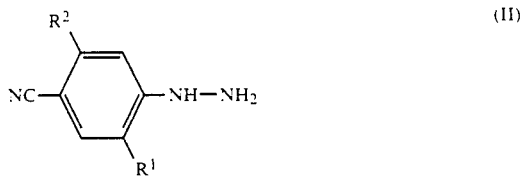

in which
$R^1$ and $R^2$ have the abovementioned meaning,
if appropriate in the presence of a diluent, such as, for example, ethanol or ethylene glycol monoethyl ether, and, if appropriate, in the presence of a reaction auxiliary, such as, for example, hydrochloric acid or sulphuric acid, at temperatures between 20° C. and 150° C.

Acrylic ester derivatives of the formula (XIX) are known or can be obtained in analogy to known processes (cf., for example, European Patent 257,882; Japanese Patent 62/148,482; PCT Int. Appl. WO 86/1202; European Patent 188,094; U.S. Pat. No. 4,555,517; European Patent 104,432; J. org. Chem. 49, 140–152 [1984]; Austral. J. Chem. 34, 2401–2421 [1981]; BE 888,389; U.S. Pat. No. 4,277,418; Farmaco. Ed. Sci. 34, 898–906 [1979]; J. chem. Soc. Perkin Trans. 1, 1979; 464–471; J. chem. Soc. Perkin Trans. 1, 1978, 1041–1046).

Suitable diluents for carrying out process (a) according to the invention are inert organic solvents. In particular, these include aliphatic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl ether or ethylene glycol diethyl ether, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, sulphoxides, such as dimethyl sulphoxide, alcohols, such as methanol, ethanol or propanol, or acids, such as acetic acid.

If appropriate, process (a) according to the invention is carried out in the presence of a suitable reaction auxiliary. In particular, possible reaction auxiliaries are inorganic mineral acids, such as, for example, hydrochloric acid or sulphuric acid. It is also possible to employ the 4-cyanophenylhydrazines of the formula (II), which are possible as starting substances, in the form of corresponding acid addition salts, such as, for example, hydrochlorides.

When carrying out process (a) according to the invention, the reaction temperatures can be varied within a relatively wide range. In general, the process is carried out at temperatures between −20° C. and 180° C., preferably at temperatures between 20° C. and 120° C.

For carrying out process (a) according to the invention, 0.5 to 10.0 moles of 1,3-diketone of the formula (III) or of a corresponding derivative and if appropriate 0.01 to 1.0 mole of reaction auxiliary are generally employed per mole of 4-cyanophenylhydrazine of the formula (II) or of a corresponding acid addition salt. The reaction is carried out and the N-aryl-substituted nitrogen-containing heterocycles of the formula (Ia) are worked up and isolated by generally customary methods (cf. also the Preparation Examples).

When 1,3-diketones of the formula (III) are used in which the substituent $R^{5-1}$ is other than the substituent $R^3$, mixtures of isomers of compounds of the formula (Ia1)

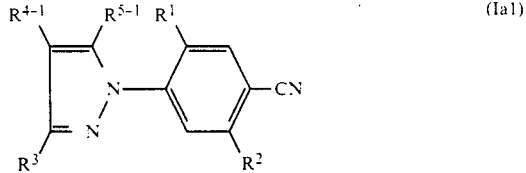

and compounds of the formula (Ia2)

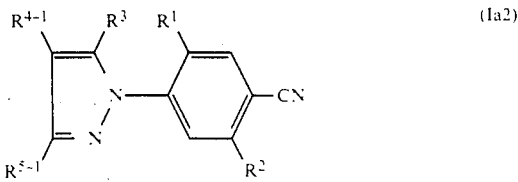

where
$R^1$, $R^2$, $R^3$, $R^{4-1}$ and $R^{5-1}$ in each case have the abovementioned meaning, are usually obtained.

The desired reaction products of the formula (Ia) may be isolated from these mixtures of isomers using customary separation methods (distillation, crystallization, chromatography).

Possible halogenating agents for carrying out process (b) according to the invention are customary halogenating agents. Sulphuryl chloride, elemental chlorine or elemental bromine are particularly preferably used as halogenating agents.

Possible diluents for carrying out process (b) according to the invention are inert organic solvents. In particular, these include aliphatic, alicyclic or aromatic, optionally halogenated hydrocarbons, such as, for example, benzine, benzene, toluene, xylene, chlorobenzene, O-dichlorobenzene, petroleum ether, hexane, cyclohexane, dichloromethane, chloroform or carbon tetrachloride.

When carrying out process (b) according to the invention, the reaction temperatures can be varied within a relatively wide range. In general, the process is carried out at temperatures between 0° C. and 150° C., preferably at temperatures between 35° C. and 70° C.

For carrying out process (b) according to the invention, 1.0 to 5.0 moles, preferably 1.0 to 2.0 moles, of halogenating agent are generally employed per mole of N-aryl-substituted nitrogen-containing heterocycle of the formula (Ij). The reaction is carried out and the reaction products are worked up and isolated by generally customary methods (cf. also the Preparation Examples).

Possible halogenating agents for carrying out process (c) according to the invention are likewise customary halogenating agents. Inorganic acid halides, such as, for example, phosphorus oxychloride, thionyl chloride, phosgene, phosphorus tribromide or diphosgene ($Cl_3C$-O-CO-Cl), are particularly preferably used.

Possible diluents for carrying out process (c) according to the invention are inert organic solvents. In particular, these include aliphatic, alicyclic or aromatic, optionally halogenated hydrocarbons, such as, for example, benzine, benzene, toluene, xylene, chlorobenzene, O-dichlorobenzene, petroleum ether, hexane, cyclohexane, dichloromethane, chloroform or carbon tetrachloride, or basic diluents, such as, for example, pyridine. It is also possible to employ an appropriate excess of halogenating agent simultaneously as the diluent.

Process (c) according to the invention is preferably carried out in the presence of a suitable reaction auxiliary. Possible reaction auxiliaries are, in particular, customary auxiliary nucleophilic substances, such as, for example, triphenylphosphine, dimethylaniline or dimethylformamide.

When carrying out process (c) according to the invention, the reaction temperatures can be varied within a relatively wide range. In general, the process is carried out at temperatures between 0° C. and 200° C., preferably at temperatures between 30° C. and 150° C.

For carrying out process (c) according to the invention, 1.0 to 10.0 moles, preferably 1.0 to 5.0 moles, of halogenating agent and, if appropriate, 0.01 to 1.0 mole, preferably 0.05 to 0.1 mole, of reaction auxiliary are generally employed per mole of N-arylpyrazolinone of the formula (IV). The reaction is carried out and the reaction products are worked up and isolated by generally customary methods (cf. also the Preparation Examples).

Possible diluents for carrying out process (d) according to the invention are inert organic solvents. In particular, these include aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl ether or ethylene glycol diethyl ether, ketones, such as acetone or butanone, nitriles, such as acetonitrile or propionitrile, amides such as dimethylformamide, dimethylacetamide, N-methylformanilide, N-methylpyrrolidone or hexamethylphosphoric triamide, esters, such as ethyl acetate, sulphoxides, such as dimethyl sulphoxide, or alcohols, such as methanol, ethanol or propanol.

When carrying out process (d) according to the invention, the reaction temperatures can be varied within a relatively wide range. In general, the process is carried out at temperatures between 0° C. and 180° C., preferably at temperatures between 50° C. and 150° C.

For carrying out process (d) according to the invention, 1.0 to 3.0 moles, preferably 1.0 to 2.0 moles, of iminocarboxylic acid ester of the formula (V) are generally employed per mole of 4-cyanophenylhydrazine of the formula (II). The reaction is carried out and the reaction products are worked up and isolated by generally customary methods (cf. also the Preparation Examples).

Possible diluents for carrying out process (e) according to the invention are inert organic solvents. Aliphatic, cyclic or aromatic, optionally halogenated hydrocarbons, such as, for example, benzine, benzene, toluene, xylene, pentane, hexane, heptane, cyclohexane, petroleum ether, ligroin, methylene chloride, chloroform, carbon tetrachloride, chlorobenzene or dichlorobenzene, ethers, such as diethyl ether, diisopropyl ether, dioxane, tetrahydrofuran or ethylene glycol diethyl ether or ethylene glycol dimethyl ether, ketones, such as acetone, butanone, methyl isopropyl ketone or methyl isobutyl ketone, esters, such as ethyl acetate, nitriles, such as acetonitrile or propionitrile, or amides, such as dimethylformamide, dimethylacetamide, N-methylpyrrolidone or hexamethylphosphoric triamide are preferably used. If alkylating agents of the formula (VI) are used in liquid form, it is also possible to employ these simultaneously as the diluent, in appropriate excess.

Possible reaction auxiliaries for carrying out process (e) according to the invention are all inorganic and organic bases which can customarily be employed. The hydrides, hydroxides, amides, carbonates or hydrogen carbonates of alkali metals, such as, for example, sodium hydride, sodium amide, sodium hydroxide, sodium carbonate, potassium carbonate or sodium hydrogen carbonate, or else tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU), are preferably used.

When carrying out preparation process (e), the reaction temperatures can be varied within a relatively wide range. In general, the process is carried out between −20° C. and +150° C., preferably between 0° C. and +100° C.

For carrying out process (e) according to the invention, 1.0 to 15.0 moles, preferably 1.0 to 5.0 moles, of alkylating agent of the formula (VI) and, if appropriate, 1.0 to 3.0 moles, preferably 1.0 to 2.0 moles, of reaction auxiliary are generally employed per mole of N-arylsubstituted nitrogen-containing heterocycle of the formula (Id). The reaction is carried out and the reaction products are worked up and isolated by generally customary methods (cf. also the Preparation Examples).

Possible diluents for carrying out processes (f) and (g) according to the invention are inert organic solvents. In particular, these include aliphatic, alicyclic or aromatic, optionally halogenated hydrocarbons, such as, for example, benzine, benzene, toluene, xylene, chlorobenzene, O-dichlorobenzene, petroleum ether, hexane, cyclohexane, dichloromethane, chloroform or carbon tetrachloride.

Processes (f) and (g) according to the invention are preferably carried out in the presence of a suitable reaction auxiliary. Possible reaction auxiliaries are all customary bases. Tertiary amines, such as triethylamine, N,N-dimethylaniline, pyridine, N,N-dimethylaminopyridine, diazabicyclooctane (DABCO), diazabicyclononene (DBN) or diazabicycloundecene (DBU) are particularly preferably used.

When carrying out processes (f) and (g) according to the invention, the reaction temperatures can be varied within a relatively wide range. In general, the process is carried out at temperatures between −20° C. and 180° C., preferably at temperatures between 0° C. and 150° C.

For carrying out process (f) according to the invention, 1.0 to 5.0 moles, preferably 1.0 to 1.5 moles, of phosgene and, if appropriate, 1.0 to 5.0 moles, preferably 1.0 to 3.0 moles, of reaction auxiliary are generally employed per mole of amidrazone of the formula (VII). The reaction is carried out and the reaction products are worked up and isolated by generally customary methods.

For carrying out process (g) according to the invention, 1.0 to 5.0 moles, preferably 1.0 to 1.5 moles, of phosgene and, if appropriate, 1.0 to 5.0 moles, preferably 1.0 to 3.0 moles, of reaction auxiliary are generally employed per mole of phenyl hydrazide of the formula (VIII). The reaction is carried out and the reaction products are worked up and isolated by generally customary methods (cf. also the Preparation Examples).

Possible diluents for carrying out process (h-α) according to the invention are inert organic solvents. In particular, these include aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide. It is also possible for the alcohols or thiols of the formula (IX), which are possible as reactants, to be employed simultaneously as the diluent, in appropriate excess.

Process (h-α) according to the invention is preferably carried out in the presence of a suitable reaction auxiliary. Possible reaction auxiliaries are all inorganic and organic bases which can customarily be employed. The hydrides, hydroxides, amides, alkoxides or carbonates of alkali metals, such as, for example, sodium hydride, sodium amide, sodium hydroxide, potassium hydroxide, sodium methoxide, sodium ethoxide, potassium t-butoxide or potassium carbonate, or else tertiary amines, such as, for example, triethylamine, N,N-dimethylaniline, pyridine, N,N-dimethylaminopyridine, diazabicyclooctane (DABCO), diazabicyclononene (DBN) or diazabicycloundecene (DBU) are preferably employed.

When carrying out process (h-α) according to the invention, the reaction temperatures can be varied within a relatively wide range. In general, the process is carried out at temperatures between 0° C. and 150° C., preferably at temperatures between 20° C. and 120° C.

For carrying out process (h-α) according to the invention, 1.0 to 3.0 moles, preferably 1.0 to 1.5 moles, of alcohol or thiol of the formula (IX) and 1.0 to 3.0 moles, preferably 1.0 to 2.0 moles, of reaction auxiliary are generally employed per mole of N-aryl-substituted nitrogen-containing heterocycle of the formula (Ik). The reaction is carried out and the reaction products are worked up and isolated by generally customary methods (cf. also the Preparation Examples).

Possible diluents for carrying out process (h-β) according to the invention are inert organic solvents. Aliphatic, alicyclic or aromatic, optionally halogenated hydrocarbons, such as, for example, benzine, benzene, toluene, xylene, pentane, hexane, heptane, cyclohexane, petroleum ether, ligroin, methylene chloride, chloroform, carbon tetrachloride, chlorobenzene or dichlorobenzene, ethers, such as diethyl ether, diisopropyl ether, dioxane, tetrahydrofuran or ethylene glycol diethyl ether or ethylene glycol dimethyl ether, ketones, such as acetone, butanone, methyl isopropyl ketone or methyl isobutyl ketone, esters, such as ethyl acetate, acids, such as acetic acid, nitriles, such as acetonitrile or propionitrile, amides, such as dimethylformamide, dimethylacetamide, N-methylpyrrolidone or hexamethylphosphoric triamide, are preferably used. If alkylating agents of the formulae (VI), (VII) or (XI) are used in the liquid form, it is also possible for these to be employed simultaneously as diluents, in appropriate excess.

Possible reaction auxiliaries for carrying out process (h-β) according to the invention are all inorganic and organic bases which can customarily be used. The hydrides, hydroxides, amides, carbonates or hydrogen carbonates of alkali metals, such as, for example, sodium hydride, sodium amide, sodium hydroxide, sodium carbonate or sodium hydrogen carbonate, or tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU) are preferably used.

When carrying out process (h-β) according to the invention, the reaction temperatures can be varied within a relatively wide range. In general, the process is carried out between −20° C. and +150° C., preferably between 0° C. and +100° C.

For carrying out process (h-β) according to the invention, 1.0 to 20.0 moles, preferably in each case 1.0 to 15.0 moles, of alkylating or acylating agent of the formula (XI) and, if appropriate, 1.0 to 3.0 moles, preferably 1.0 to 2.0 moles, of reaction auxiliary are generally employed per mole of (thio)phenol derivative of the formula (X). The reaction is carried out and the reaction products of the formula (Ih) are worked up and isolated by customary methods.

Possible diluents for carrying out process (i) according to the invention are inorganic or organic solvents. Polar solvents, in particular alcohols, such as, for example, methanol, ethanol or propanol, or their mixtures with water, are preferably used.

Possible reaction auxiliaries for carrying out process (i) according to the invention are all catalysts which can customarily be used for ester hydrolyses and decarboxylations of this type. Bases, such as, for example, sodium hydroxide, sodium alkoxide or sodium carbonate, or acids, such as, for example, hydrochloric acid, hydrobromic acid or sulphuric acid, are preferably used.

When carrying out process (i) according to the invention, the reaction temperatures can be varied within a relatively wide range. In general, the process is carried out at temperatures between 20° C. and 250° C., preferably at temperatures between 50° C. and 150° C.

For carrying out process (i) according to the invention, 1.0 to 15.0 moles, preferably 1.0 to 2.0 moles, of acid or basic reaction auxiliary are generally employed per mole of 1-arylpyrazolyl-4-carboxylic acid ester of the formula (XII) and the mixture is heated for several hours at the reaction temperature required. The reaction products are worked up and isolated by generally customary methods.

Depending on the reaction temperature and the duration of the reaction, it is also possible to isolate the 1-arylpyrazolyl-4-carboxylic acids, which occur as intermediates, and to decarboxylate them in a separate reaction step.

The active compounds according to the invention can be used as defoliants, desiccants, agents for destroying broadleaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

Here, the active compounds of the formula (I) according to the invention can be employed with particularly good success for combating dicotyledon weeds in monocotyledon and dicotyledon crops, such as, for example, soya or wheat. The intermediates of the formula (X) also possess a good herbicidal activity.

The active compounds according to the invention furthermore engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amount of active compound applied to the plants or their environment and the way in which the compounds are employed. In each case, growth regulators are intended to influence the crop plants in the particular manner desired.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable:

for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants, such as inorganic pigments, for example iron oxide, titanium oxide and Prussian Blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations in general contain between 0.1 and 95 per cent by weight of active compound, preferably between 0.5 and 90%.

When used as herbicides, the active compounds according to the invention, as such or in the form of their formulations, can also be used as mixtures with known herbicides for combating weeds, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (amethydione) or N-(2-benzothiazolyl)-N,N'-dimethyl-urea (metabenzthiazuron) for combating weeds in cereals; 4-amino -3-methyl-6-phenyl-1,2,4-triazin-5(4H)-one for (metamitron) combating weeds in sugar beet, and 4-amino-6-(1,1-dimethylethyl)-3-methylthio-1,2,4-triazin-5(4H)-one (metribuzin) for combating weeds in soya beans. Mixtures with 2,4-dichlorophenoxyacetic acid (2,4-D);

2,4-dichlorophenoxypropionic acid (2,4-DP);
4-(2,4-dichlorophenoxy)butyric acid (2,4-DB);
(2-methyl-4-chlorophenoxy)-acetic acid (MCPA);
(4-chloro-2-methylphenoxy)-propionic acid (MCPP);
[(4-amino-3,5-dichloro-6-fluoro-2-pyridin-yl)-oxy]-acetic acid or its 1-methylheptyl ester (FLUROXYPYR);
2-[4-(2,4-dichlorophenoxy)-phenoxy]-propionic acid, its methyl or its ethyl ester (DICLOFOP[METHYL]);
2-{4-[(6-chloro-2-benzoxazolyl)-oxy]-phenoxy}-propanoic acid, its methyl or ethyl ester (FENOXAPROP);
methyl 5-(2,4-dichlorophenoxy)-2-nitrobenzoate (BIFENOX);
N-methoxymethyl-2,6-diethylchloroacetanilide (ALACHLOR);
2-chloro-N-(2,6-dimethylphenyl)-N-[(1H)-pyrazol-1-yl-methyl]-acetamide (METAZACHLOR);
2-ethyl-6-methyl-N-(1-methyl-2-methoxyethyl)-chloroacetanilide (METOLACHLOR);
N-(1-ethylpropyl)-3,4-dimethyl-2,6-dinitroaniline (PENDIMETHALIN);
2,6-dinitro-4-trifluoromethyl-N,N-dipropylaniline (TRIFLURALIN);
N,N-dimethyl-N'-(3-chloro-4-methylphenyl)-urea (CHLORTOLURON);
N,N-dimethyl-N'-(4-isopropylphenyl)-urea (ISOPROTURON);
2-[4,5-dihydro-4-methyl-4-isopropyl-5-oxo-(1H) -imidazol-2-yl]-5-ethylpyridine-3-carboxylic acid (IMAZETHAPYR);
methyl 2-[4,5-dihydro-4-methyl-4-(1-methylethyl)-5-oxo -1H-imidazol-2-yl]-4(5)-methylbenzoate (IMAZAMETHABENZ);
2-[5-methyl-5-(1-methylethyl)-4-oxo-2-imidazolin-2-yl]-3-quinolinecarboxylic acid (IMAZAQUIN);
3,5-dibromo-4-hydroxy-benzonitrile (BROMOXYNIL);
3,5-diiodo-4-hydroxybenzonitrile (IOXYNIL);
N-methyl-2-(1,3-benzothiazol-2-yloxy)-acetanilide (MEFENACET);
ethyl 2-{[(4-chloro-6-methoxy-2-pyrimidinyl)-aminocarbonyl]-aminosulphonyl}-benzoate (CHLORIMURON);
2-chloro-N-{[(4-methoxy-6-methyl-1,3,5-triazin-2-yl)amino]-carbonyl}-benzenesulphonamide (CHLORSULFURON);
2-{[[((4-methoxy-6-methyl-1,3,5-triazin-2-yl)-amino)-carbonyl]-amino]-sulphonyl}-benzoic acid or its methyl ester (METSULFURON);
methyl 3-[[[[(4-methoxy-6-methyl-1,3,5-triazin-2-yl)amino]-carbonyl]-amino]-sulphonyl]-thiophene-2-carboxylate (THIAMETHURON);
S-2,3,3-trichloroallyl N,N-diisopropylthiolcarbamate (TRIALLATE);
4-ethylamino-2-t-butylamino-6-methylthio-s-triazine (TERBUTRYNE)
3-isopropyl-2,1,3-benzothiadiazin-4-one 2,2-dioxide (BENTAZONE);
4-amino-6-t-butyl-3-ethylthio-1,2,4-triazin-5(4H)-one (ETHIOZIN);
2-[(2-chlorophenyl)-methyl]-4,4-dimethylisoxazolidin-3-one [DIMETHAZONE];
exo-1-methyl-4-(1-methylethyl)-2-(2-methylphenyl-mathoxy)-7-oxabicyclo-(2,2,1)-heptane (CINMETHYLIN) and
O-(6-chloro-3-phenyl-pyridazin-4-yl) S-octyl thiocarbonate (PYRIDATE) are also possible. Surprisingly, some mixtures also exhibit a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

When applied as herbicides, the amount of active compound used can vary within a substantial range. It depends essentially on the nature of the desired effect. In general, the amounts used are between 0.01 and 10 kg of active compound per hectare of soil surface, preferably between 0.05 and 5 kg per ha.

When used as growth regulators, the active compounds according to the invention can be present in the formulations also as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

When the compounds are used as plant growth regulators, the amounts applied can also be varied within a substantial range. In general, 0.01 to 50 kg, preferably 0.05 to 10 kg, of active compound are used per hectare of soil surface.

As far as the time of application is concerned, the application of the growth regulators is carried out in a preferred period, the exact limits of which depend on the climatic and vegetative conditions.

PREPARATION EXAMPLES

Example 1

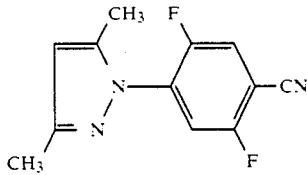

(Process a)

1.1 g (0.125 mol) of 4-cyano-2,5-difluorophenylhydrazine and 12.5 g (0.125 mol) of 2,4-pentanedione are stirred for 2 hours at room temperature in 250 ml of ethanol, and the mixture is subsequently heated at 70° C. for 15 hours and then evaporated in vacuo. The residue is stirred with petroleum ether and filtered off with suction.

28 g (96% of theory) of 4-(3,5-dimethyl-1-pyrazolyl)-2,5-difluorobenzonitrile of melting point 122° C. are obtained.

Example 2

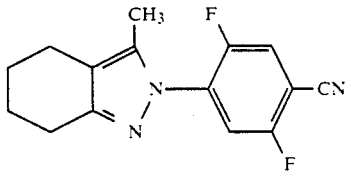

(Process a)

5.2 ml (0.04 mol) of 2-acetylcyclohexanone (cf., for example, J. org. Chem. 34, 1425–1429 [1969]) are added to 6.76 g (0.04 mol) of 4-cyano-2,5-difluorophenylhydrazine in 40 ml of glacial acetic acid, the reaction mixture is stirred at room temperature for 2 hours and then stirred into 250 ml of ice-water, the mixture is extracted with dichloromethane, dried over sodium sulphate and evaporated in vacuo, and the residue is recrystallized from dichloromethane/n-hexane.

3.21 g (23.5% of theory) of 4-(5-methyl-3,4-tetramethylene-1-pyrazolyl)-2,5-difluorobenzonitrile of melting point 120° C. are obtained.

Example 3

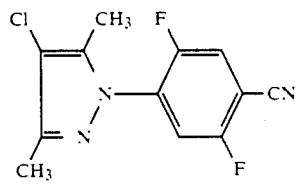

(Process b)

1.68 g (=1 ml; 0.012 mol) of sulphuryl chloride are added to 2.3 g (0.01 mol) of 4-(3,5-dimethyl-1-pyrazolyl)-2,5-difluorobenzonitrile in 50 ml of dichloromethane, the mixture is stirred at 35° C. for 15 hours, allowed to come to room temperature, dried over sodium sulphate and evaporated in vacuo, and the residue is purified by stirring with petroleum ether.

2.0 g (75% of theory) of 4-(3,5-dimethyl-4-chloro-1-pyrazolyl)-2,5-difluorobenzonitrile of melting point 153° C. are obtained.

Example 4

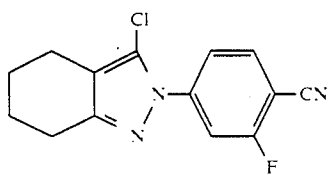

(Process c)

1.78 g (0.0068 mol) of triphenylphospine are added to 15 g (0.068 mol) of 1-(4-cyano-3-fluorophenyl)-3,4-tetramethylene-(1H,4H)-pyrazolin-5-one in 28.8 ml (0.2 mol) of phosphorus oxychloride, and the mixture is heated at reflux temperature for 15 hours. For working up, the cooled reaction mixture is poured into 300 ml of ice-water, the mixture is stirred for 1 hour, and precipitated product is filtered off with suction, washed with water and dried.

15.2 g (81% of theory) of 1-(4-cyano-3-fluorophenyl)-5-chloro-3,4-tetramethylenepyrazole of melting point 84°–86°. C. are obtained.

Example 5

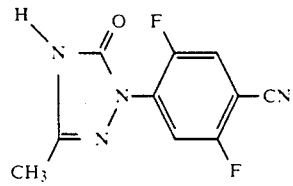

(Process d)

8.45 g (0.05 mol) of 4-cyano-2,5-difluorophenylhydrazine and 12.08 g (0.078 mol) of ethyl N-ethoxycarbonylethaneimidate (cf., for example, Chem. Ber. 119, 2444–2457 [1986]) are heated at reflux temperature for 8 hours in 50 ml of xylene, the mixture is then cooled to room temperature, and solids are filtered off with suction and recrystallized from dichloromethane/petroleum ether.

5.91 g (50% of theory) of 1-(4-cyano-2,5-difluorophenyl)3-methyl-4,5-dihydro-1,2,4-triazolin-5-one of melting point 174° C. are obtained which has precipitated is filtered off, the mixture is concentrated in vacuo, and the residue is recrystallized from dichloromethane/petroleum ether.

14.33 g (64% of theory) of 3-(4-cyano-2,5-difluorophenyl)-5-t-butyl-1,3,4-oxadiazolin-2-one of melting point 137° C. are obtained.

Example 6

(Process e)

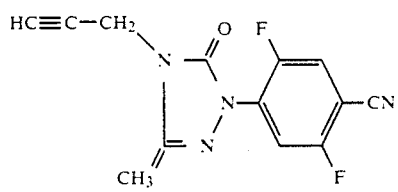

2.36 g (0.01 mol) of 1-(4-cyano-2,5-difluorophenyl)-2-methyl-4,5-dihydro-1,2,4-triazolin-5-one and 1.52 g (0.011 mol) of potassium carbonate in 20 ml of acetonitrile are heated at reflux temperature for 2 hours, the mixture is subsequently cooled to 25° C., an 80 per cent strength solution of 1.31 g (0.011 mol) of propargyl bromide in toluene is added, and the mixture is heated at reflux temperature for 4 more hours. For working up, the mixture is evaporated in vacuo, and the residue is taken up in dichloromethane, washed with saturated aqueous sodium hydrogen carbonate solution and water, dried over sodium sulphate, evaporated in vacuo and recrystallized from dichloromethane/petroleum ether.

2.16 g (79% of theory) of 1-(4-cyano-2,5-difluorophenyl-3-methyl-4-propargyl-4,5-dihydro-1,2,4-triazolin-5-one of melting point 127° C. are obtained.

Example 8

(Process h-α)

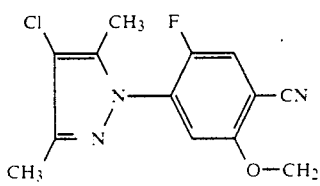

0.8 g (0.025 mol) of 80 per cent pure sodium hydride (in paraffin oil) is added to 2.7 (0.01 mol) of 4-(3,5-dimethyl-4-chloro-1-pyrazolyl)-2,5-difluorobenzonitrile in 50 ml of ethylene glycol monomethyl ether at 0° C., and the mixture is stirred for 4 hours at 0° C. and subsequently for 15 hours at room temperature. For working up, 200 ml of water are slowly added with cooling, the mixture is stirred at room temperature for one hour, and any solids which have precipitated are filtered off, washed with water and dried.

3.2 g (95% of theory) of 4-(3,5-dimethyl-4-chloro-1-pyrazolyl)-2-(2-ethoxyethoxy)-5-fluorobenzonitrile of melting point 86° C. are obtained.

Example 7

(Process g)

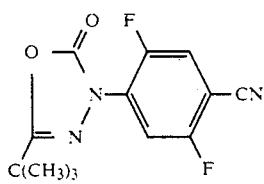

11.9 g (0.12 mol) of phosgene are passed into a solution of 20.24 g (0.08 mol) of 1-(4-cyano-2,5-difluorophenyl)-2-pivaloylhydrazine in 200 ml of toluene, 24.24 g (0.24 mol) of triethylamine in 20 ml of toluene are then added dropwise with stirring, and the mixture is heated at 100° C. for one hour. For working up, excess phosgene is removed, any triethylamine hydrochloride

Example 9

(Process h-α)

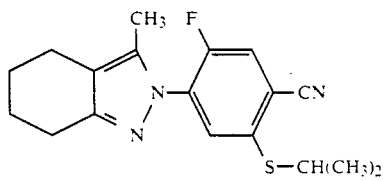

1.02 ml (0.011 mol) of isopropylmercaptan and 0.84 g (0.015 mol) of powdered potassium hydroxide are added in succession to 3 g (0.011 mol) of 4-(5-methyl-3,4-tetramethylene-1-pyrazolyl)-2,5-difluorobenzonitrile in 30 ml of absolute acetonitrile. The mixture is subsequently stirred at 40° C. until starting material is no longer detectable in the thin-layer chromatogram, dichloromethane is then added, and the mixture is filtered. The filtrate is evaporated in vacuo, the residue is chromatographed on silica gel (eluent: cyclohexane/ethyl acetate 3:1) and recrystallized from n-hexane.

1.7 g (47% of theory) of 4-(5-methyl-3,4-tetramethylene -1-pyrazolyl)-5-fluoro-2-isopropylthiobenzonitrile of melting point 105° C. are obtained.

Example 10

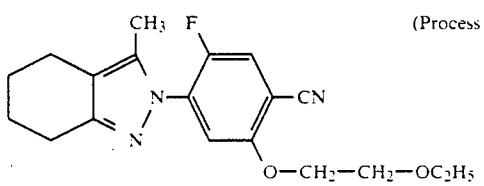

(Process h-α)

1.7 ml (0.017 mol) of 2-ethoxyethanol is added dropwise with stirring at room temperature to 0.51 g (0.017 mol) of sodium hydride in 30 ml of N-methylpyrrolidone, the mixture is stirred at room temperature for 15 more minutes, 4.1 g (0.015 mol) of 4-(5-methyl-3,4-tetramethylene-1-pyrazolyl)-2,5-difluorobenzonitrile are then added, and stirring is continued at 80° C. until starting material is no longer detectable in the thin-layer chromatogram. For working up, the cooled reaction mixture is stirred into 200 ml of ice-water, the mixture is extracted with toluene, and the extract is dried over sodium sulphate, concentrated in vacuo, chromatographed on silica gel (eluent: cyclohexane/ethyl acetate 2:1) and recrystallized from diethyl ether/n-hexane.

3.51 g (68% of theory) of 4-(5-methyl-3,4-tetramethylene -1-pyrazolyl)-2-(2-ethoxyethoxy)-5-fluorobenzonitrile of melting point 84° C. are obtained.

The following N-aryl-substituted nitrogen-containing heterocycles of the general formula (I) are obtained in a corresponding manner an in accordance with the general preparation instructions:

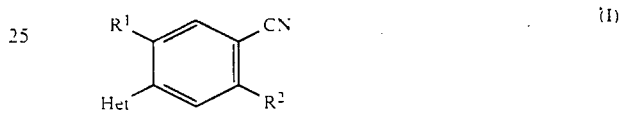

(I)

TABLE 1

| Example No | R¹ | R² | Het | Melting point/°C. |
|---|---|---|---|---|
| 11 | F | —O—CH₂—CH₂—OC₂H₅ | (5-methyl-pyrazolyl with CH₃) | 103 |
| 12 | H | —S—CH₂—COOC₂H₅ | (4,5,6,7-tetrahydro-3-chloroindazolyl) | 112–114 |
| 13 | H | —O—CH₂—CH₂—OCH₃ | (4,5,6,7-tetrahydro-3-chloroindazolyl) | 69–72 |
| 14 | H | —O—CH₂—CH₂—OC₂H₅ | (4,5,6,7-tetrahydro-3-chloroindazolyl) | 62–64 |
| 15 | H | —O—CH(CH₂F)₂ | (4,5,6,7-tetrahydro-3-chloroindazolyl) | |
| 16 | F | F | (4,5,6,7-tetrahydro-3-chloroindazolyl) | 112–113 |

TABLE 1-continued

| Example No | R¹ | R² | Het | Melting point/°C |
|---|---|---|---|---|
| 17 | F | —S—CH₂—COOC₂H₅ | 3-Cl-4,5,6,7-tetrahydro-2H-indazol-2-yl | 106–108 |
| 18 | F | —O—CH₂—CH₂—OC₂H₅ | 3-Cl-4,5,6,7-tetrahydro-2H-indazol-2-yl | 107–109 |
| 19 | F | F | 1,3,4,5-tetramethylpyrazol-1-yl | 146–149 |
| 20 | F | OCH₃ | 1,3,4,5-tetramethylpyrazol-1-yl | 179–181 |
| 21 | F | —S—CH₂—COOC₂H₅ | 1,3,4,5-tetramethylpyrazol-1-yl | 136–137 |
| 22 | F | —O—CH₂—CH₂—OCH₃ | 1,3,4,5-tetramethylpyrazol-1-yl | 127–128 |
| 23 | F | —O—CH(CH₂F)₂ | 1,3,4,5-tetramethylpyrazol-1-yl | 94–96 |
| 24 | H | —O—CH₂—CH=CH₂ | 3-Cl-4,5,6,7-tetrahydro-2H-indazol-2-yl | 123–125 |
| 25 | H | F | 5-methyl-3-oxo-2,3-dihydro-1,2,4-triazol-2-yl | 246–250 |
| 26 | H | F | 4-methyl-5-methyl-3-oxo-4,5-dihydro-1,2,4-triazol-2-yl | 181–186 |
| 27 | F | —O—CH₂—CH₂—O—CH₃ | 3-methyl-4-chloro-5-methylpyrazol-1-yl | 94 |

TABLE 1-continued

| Example No | R¹ | R² | Het | Melting point/°C |
|---|---|---|---|---|
| 28 | F | —O—CH₂—C≡CH | 3-methyl-4-chloro-5-methyl-pyrazolyl | 136 |
| 29 | F | —O—CH₂—CH=CH₂ | 3-methyl-4-chloro-5-methyl-pyrazolyl | 118 |
| 30 | F | —O—CH(CH₃)₂ | 3-methyl-4-chloro-5-methyl-pyrazolyl | 88 |
| 31 | F | —S—CH₂—COOC₂H₅ | 3-methyl-5-methyl-pyrazolyl | 110 |
| 32 | F | —O—CH(CH₂F)₂ | 3-methyl-5-methyl-pyrazolyl | 110 |
| 33 | F | —O—CH(CH₃)—COOC₂H₅ | 3-methyl-5-methyl-pyrazolyl | 86 |
| 34 | F | —O—CH(CH₂F)₂ | 3-methyl-4-chloro-5-methyl-pyrazolyl | 116 |
| 35 | F | —O—CH₂CH₂—O—C₂H₅ | 3-methyl-4-bromo-5-methyl-pyrazolyl | 97 |
| 36 | F | —S—CH₂—COOC₂H₅ | 3-methyl-4-chloro-5-methyl-pyrazolyl | 94 |
| 37 | F | —O—CH₂CH₂—O—CH₃ | 3-methyl-4-bromo-5-methyl-pyrazolyl | 104 |

TABLE 1-continued

| Example No | R¹ | R² | Het | Melting point/°C |
|---|---|---|---|---|
| 38 | F | —O—CH₂—CH=CH₂ | H₃C, Br / pyrazole / CH₃ (N-methyl) | 126 |
| 39 | F | —O—CH(CH₂F)₂ | H₃C, Br / pyrazole / CH₃ (N-methyl) | 122 |
| 40 | F | —S—CH₂—COOC₂H₅ | H₃C, Br / pyrazole / CH₃ (N-methyl) | 107 |
| 41 | F | —O—CH₂—C≡CH | H₃C, Br / pyrazole / CH₃ (N-methyl) | 104 |
| 42 | F | —O—CH(CH₃)₂ | H₃C, Br / pyrazole / CH₃ (N-methyl) | 108 |
| 43 | F | —S—CH₂—COOCH₃ | H₃C, / pyrazole / CH₃ (N-methyl) | 103 |
| 44 | F | —S—CH₂—COOCH₃ | H₃C, Cl / pyrazole / CH₃ (N-methyl) | 108 |
| 45 | F | —S—CH₂—COOCH(CH₃)₂ | H₃C, Cl / pyrazole / CH₃ (N-methyl) | 135 |
| 46 | F | —S—CH₂—COO-cyclopentyl | H₃C, Cl / pyrazole / CH₃ (N-methyl) | 120 |
| 47 | F | —O—CH₂CH₂OCH₃ | H₃C, / pyrazole / CH₃ (N-methyl) | 112 |

TABLE 1-continued

| Example No | R¹ | R² | Het | Melting point/°C. |
|---|---|---|---|---|
| 48 | F | —O—CH₂—C≡CH | 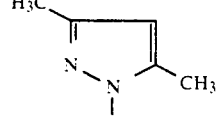 | 141 |
| 49 | F | —O—CH₂CH=CH₂ | 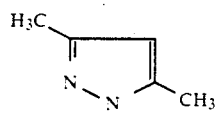 | 120 |
| 50 | F | —O—C₃H₇-iso | 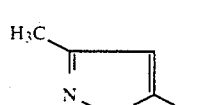 | 99 |

PREPARATION OF THE STARTING COMPOUNDS

Example II-1

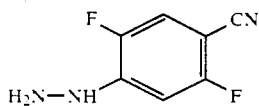

11 g (0.22 mol) of hydrazine hydrate are added to 30 g (0.19 mol) of 2,4,5-trifluorobenzonitrile (cf., for example, EP-A 191,181) in 120 ml of ethanol, the mixture is heated at reflux temperature for 2 hours, cooled to room temperature and concentrated in vacuo, the residue is stirred with 50 ml of water, and any product which has precipitated is filtered off with suction and dried.

24 g (75% of theory) of 4-cyano-2,5-difluorophenylhydrazine of melting point 158° C. are obtained.

Example II-2

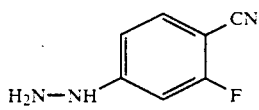

45 g (0.9 mol) of hydrazine hydrate are added dropwise with stirring to 90 g (0.65 mol) of 2,4-difluorobenzonitrile (cf., for example, EP-A 122,693) in 300 ml of methanol, the mixture is heated at reflux temperature for 3 hours and then concentrated in vacuo, and the residue is stirred with 300 ml of water, filtered off with suction and dried.

73 g (74% of theory) of 4-cyano-3-fluorophenylhydrazine of melting point 136° C. are obtained.

Example II-3

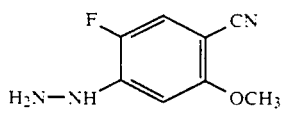

5 g (0.125 mol) of powdered sodium hydroxide are added to 13 g (0.076 mol) of 4-cyano-2,5-difluorophenylhyirazine in 100 ml of methanol, the mixture is then heated at reflux temperature for 6 hours and subsequently evaporated in vacuo, the residue is transferred to 50 ml of water, the mixture is rendered neutral by the dropwise addition of acetic acid, and any solids which have precipitated are filtered off with suction and recrystallized from toluene.

9 g (65% of theory) of 4-cyano-2-fluoro-5-methoxyphenylhydrazine of melting point 155°-156° C. are obtained.

Example IV-1

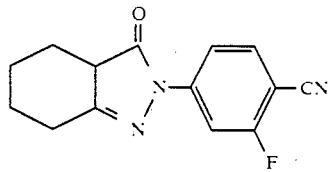

11.3 ml (0.096 mol) of 2-ethoxycarbonylcyclohexanone (cf., for example, J. chem. Soc. D 1970, 326-327) are added to 11 g (0.08 mol) of 4-cyano-3-fluorophenylhydrazine in 80 ml of ethanol, the mixture is heated at reflux temperature for 8 hours and then cooled to 60° C., 0.5 ml of sulphuric acid are added, the mixture is then stirred at 60° C. for 15 hours, 500 ml of water are then added, and any product which has precipitated is filtered off with suction, washed with water and dried.

17.7 g (99% of theory) of 1-(4-cyano-3-fluorophenyl)-3,4-tetramethylene-(1H,4H)-pyrazolin-5-one of melting point 218°-220° C. are obtained.

Example VIII-1

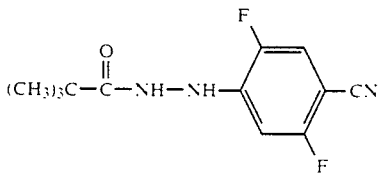

12.05 g (0.1 mol) of pivaloyl chloride are added dropwise at 0° C. with stirring and ice-cooling to 16.9 g (0.1 mol) of 4-cyano-2,5-difluorophenylhydrazine and 12.4 g (0.105 mol) of triethylamine in 50 ml of dichloromethane; when the addition is complete, the mixture is stirred at 20° C. for 10 hours and then evaporated in vacuo, the residue is distributed between dichloromethane and water, the organic phase is dried over sodium sulphate, and the solvent is removed in vacuo.

24.85 g (98% of theory) of 1-(4-cyano-2,5-difluorophenyl)-2-pivaloylhydrazine of melting point 167° C. are obtained.

Example X-1

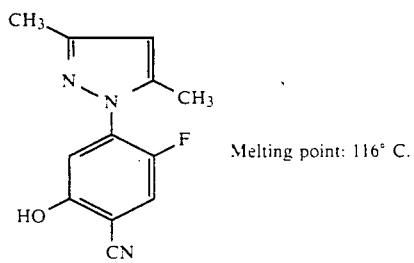

Melting point: 116° C.

Example X-2

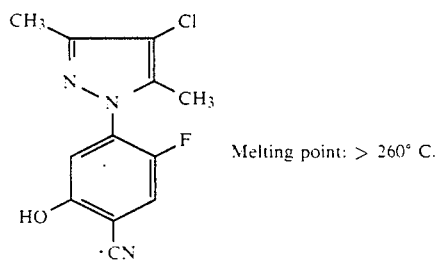

Melting point: > 260° C.

USE EXAMPLES

In the following Use Examples, the compound shown below was employed as comparison substance:

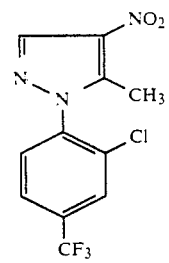

(A)

1-(2-Chloro-4-trifluoromethylphenyl)-5-methyl-4-nitropyrazole
(disclosed in EP-A 200,872/Example 19)

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:
0% = no action (like untreated control)
100% = total destruction In this test, for example the compounds of Preparation Examples 10, 14, 16, 17, 18 and 23 are clearly superior to the prior art, with respect to both effectiveness and crop plant selectivity.

EXAMPLE B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:
0% = no action (like untreated control)
100% = total destruction A clearly superior effectiveness as well as crop plant selectivity, compared with the prior art, is shown in this test for example by the compounds of the following Preparation Examples; 9: 10, 12, 14, 16, 17, 18, 23 and 44.

EXAMPLE C

Defoliation and desiccation of the leaves of cotton
Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Cotton plants are grown in a greenhouse until the 5th true leaf has unfolded completely. In this stage, the plants are sprayed with the preparations of active compound until dripping wet. After 1 week, the shedding of leaves and the desiccation of the leaves are rated, in comparison with the control plants.

The figures of merit have the following meanings:
0 denotes no desiccation of leaves, no shedding of leaves +denotes slight desiccation of the leaves, slight shedding of leaves ++denotes severe desiccation of the leaves, severe shedding of leaves +++denotes very severe desiccation of the leaves, very severe shedding of leaves.

A clear superiority compared with the untreated control is shown in this test for example by the compounds of the following Preparation Examples: 13 and 16.

It is understood that the specification and examples are illustrative but not limitative of the present invention and that other embodiments within the spirit and scope of th invention will suggest themselves to those skilled in the art.

We claim:

1. An N-Aryl-substituted nitrogen-containing heterocycle of the general formula (I)

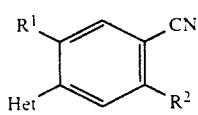 (I)

in which

Het represents a heterocycle of the formula

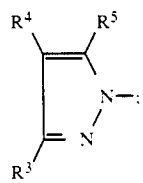

$R^1$ represents hydrogen or alkyl, and $R^2$ represents a radical —X—$R^9$, where $R^3$ represents hydrogen or alkyl, and $R^4$ represents halogen, $R^5$ represents hydrogen or alkyl $R^9$ represents an alkoxy-carbonylalkyl and X represents oxygen or sulphur.

2. An N-Aryl-substituted nitrogen-containing heterocycle of the formula (I) as claimed in claim 1, in which Het represents a heterocycle of the formula

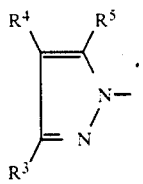

$R^1$ represents hydrogen, fluorine, chlorine or bromine and $R^2$ represents a radical —X—$R^9$, $R^3$ represents hydrogen, or represents straight-chain or branched alkyl having 1 to 6 carbon atoms and $R^4$ represents fluorine, chlorine, bromine, or iodine, $R^5$ represents hydrogen or represents straight-chain or branched alkyl having 1 to 6 carbon atoms, $R^9$ represents alkoxy-carbonylalkyl having 1 to 8 carbon atoms in the alkyl moiety and X represents oxygen or sulphur.

3. A compound according to claim 1 wherein such compound is

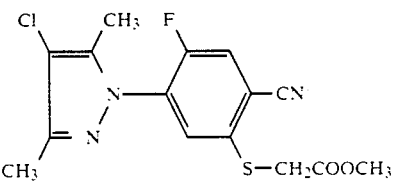

4. A herbicidal and plant growth-regulating composition comprising a herbicidally or plant growth regulating effective amount of a N-aryl-substituted nitrogen-containing heterocycle of the formula (I) according to claim 1 in admixture with a diluent.

5. A method of combating unwanted vegetation which comprises applying to such vegetation or to a locus from which it is desired to exclude such vegetation a herbicidally effective amount of a compound according to claim 1.

6. A method for regulating the growth of plants which comprises applying to such plants or to a locus in which such plants are grown or to be grown a plant growth regulating effective amount of a compound according to claim 1.

7. The method according to claim 5 wherein such compound is

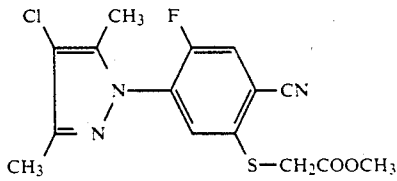

* * * * *

UNITED STATES PATENT AND TRADEMARK OFFICE
CERTIFICATE OF CORRECTION

PATENT NO. : 5,006,148
DATED      : April 9, 1991
INVENTOR(S): Fischer et al.

It is certified that error appears in the above-identified patent and that said Letters Patent is hereby corrected as shown below:

Col. 333, line 45   Delete " alkyl " and substitute -- halogen --

Col. 334, line 12   After " -X-$R^9$, " insert -- where --

Signed and Sealed this

Eighth Day of June, 1993

Attest:

MICHAEL K. KIRK

Attesting Officer    Acting Commissioner of Patents and Trademarks